US007115722B1

(12) United States Patent
Dan et al.

(10) Patent No.: US 7,115,722 B1
(45) Date of Patent: Oct. 3, 2006

(54) ANTIGEN BINDING FRAGMENTS THAT SPECIFICALLY DETECT CANCER CELLS, NUCLEOTIDES ENCODING THE FRAGMENTS, AND USE THEREOF FOR THE PROPHYLAXIS AND DETECTION OF CANCERS

(75) Inventors: Michael D. Dan, Scarsborough (CA); Howard A. Kaplan, Winnipeg (CA); Pradip K. Maiti, Winnipeg (CA)

(73) Assignee: Viventia Biotech, Inc., Toronto (CA)

( * ) Notice: Subject to any disclaimer, the term of this patent is extended or adjusted under 35 U.S.C. 154(b) by 0 days.

(21) Appl. No.: 09/194,164

(22) PCT Filed: May 22, 1997

(86) PCT No.: PCT/US97/08962

§ 371 (c)(1),
(2), (4) Date: Apr. 9, 1999

(87) PCT Pub. No.: WO97/44461

PCT Pub. Date: Nov. 27, 1997

(51) Int. Cl.
*C07H 21/02* (2006.01)
*C07K 1/00* (2006.01)

(52) U.S. Cl. .................................. 536/23.1; 530/387.1
(58) Field of Classification Search ................ 536/23.5, 536/23.53, 23.1; 530/387.1; 435/320.1, 435/325, 6
See application file for complete search history.

(56) References Cited

U.S. PATENT DOCUMENTS

| | | | |
|---|---|---|---|
| 3,817,837 A | 6/1974 | Rubenstein et al. |
| 3,850,752 A | 11/1974 | Schuur et al. |
| 3,939,350 A | 2/1976 | Kronick et al. |
| 3,996,345 A | 12/1976 | Ullman et al. |
| 4,275,149 A | 6/1981 | Litman et al. |
| 4,277,437 A | 7/1981 | Maggio |
| 4,366,241 A | 12/1982 | Tom et al. |
| 4,618,477 A | 10/1986 | Babu et al. |
| 4,683,195 A | 7/1987 | Mullis et al. |
| 4,683,202 A | 7/1987 | Mullis |
| 4,754,065 A | 6/1988 | Levenson et al. |
| 4,800,159 A | 1/1989 | Mullis et al. |
| 4,983,586 A | 1/1991 | Bodor |
| 5,002,935 A | 3/1991 | Bodor |
| 5,017,566 A | 5/1991 | Bodor |
| 5,153,179 A | 10/1992 | Eibl |
| 5,270,202 A | 12/1993 | Raychaudhuri |
| 5,474,755 A | 12/1995 | Hanna, Jr. et al. |
| 5,530,101 A | 6/1996 | Queen et al. |
| 5,585,089 A | 12/1996 | Queen et al. |

FOREIGN PATENT DOCUMENTS

| | | |
|---|---|---|
| EP | 0 329 400 | 8/1989 |
| EP | 0 699 755 | 3/1996 |
| WO | WO 91/04014 | 4/1991 |
| WO | WO 92/20799 | 11/1992 |
| WO | WO 93/07286 | 4/1993 |
| WO | WO 95/35374 | 12/1995 |

OTHER PUBLICATIONS

Reiger et al (Glossary of Genetics and Cytogenetics, Classical and Molecular, 4th Ed., Springer-Verlay, Berlin, 1976).*
Westwood et al (Epitope Mapping 2001;chapter 1 pp. 5-6).*
(Weiner L.M., Seminars Oncology, vol. 26, No. 4, Suppl 12, pp. 41-50, 1999).*
Gura (Science, v278, 1997, pp. 1041-1042).*
Marchant, "Contemporary management of breast cancer" *Obstetrics and Gynecology Clinics of North America* (1994) 21:555-560.
Colditz, "Epidemiology of breast cancer" *Cancer* (1993) 71:1480-1489.
Kohn et al., "Molecular insights into cancer invasion: Strategies for prevention and intervention" *Cancer Res.* (1995) 55:1856-1862.
Koda et al., "Three step radioimmunodiagnosis of colon cancers using murine and human monoclonal antibodies" *Am. J. Gastroenterol.* (1995) 90: Abstract No. 357.
Hall, "Monoclonal antibodies at age 20: Promise at last?" *Science* (1995) 270:915-916.
Schattner, "The origin of autoantibodies" *Immunol. Lett.* (1986/1987) 14:143-153.
Lutz et al., "Naturally occurring autoantibodies to skeletal proteins from human red blood cells" *J. Immunol.* (1982) 128:1695-1699.
Guilbert et al., "Naturally occurring antibodies against nine common antigens in human sera" J. Immunol. (1982) 128:2779-2787.
Glassy, "Immortalization of human lymphocytes from a tumor-involved lymph node" *Cancer Res.* (1987) 47:5181-5188.
Fischer et al., "Paucity of humoral response in patients to glioma-associated antigen(s): Antigen localization by immunofluorescence" *Immunobiol. of Proteins and Peptides VI* (1991) M. Atassi, ed., Plenum Press, NY, pp. 263-270.
Skerra, "Bacterial expression of immunoglobulin fragments" *Curr. Opin. Immunol.* .(1993) 5:256-262.
Fiedler et al., "High-level production and long-term storage of engineered antibodies in transgenic tobacco seeds" *Bio/Technology* (1995) 13:1090-1093.
Zhang et al., "A human monoclonal antimelanoma single-chain Fv antibody derived from tumor-infiltrating lymphocytes" *Cancer Res.* (1995) 55:3584-3591.

(Continued)

*Primary Examiner*—Christopher Yaen
(74) *Attorney, Agent, or Firm*—Morrison & Foerster LLP

(57) ABSTRACT

The present invention relates to monoclonal antibody H11 and antigen binding fragments that specifically bind to the antigen recognized by H11, the C-antigen. The C-antigen is found specifically on neoplastic cells and not on normal cells. Also disclosed are polynucleotide and polypeptide derivatives based on H11, including single chain V region molecules and fusion proteins, and various pharmaceutical compositions. When administered to an individual, the H11 antibody is effective in diagnosing, localizing, and/or treating neoplasias. The invention further provides methods for treating a neoplastic disease, particularly melanoma, neuroblastoma, glioma, soft tissue sarcoma, and small cell lung carcinoma. Patients who are in remission as a result of traditional modes of cancer therapy may be treated with a composition of this invention in hopes of reducing the risk of recurrence. Patients may also be treated concurrently with the antibodies and traditional anti-neoplastic agents.

49 Claims, 20 Drawing Sheets

OTHER PUBLICATIONS

Barbas, "Synthetic human antibodies" *Nature Med.* (1995) 1:837-839.

Yoshikawa et al., "A human monoclonal antibody recognizing a surface antigen on stomach cancer cells" Jpn. J. Cancer Res. (1989) 80:546-553.

Yamaguchi et al., "Cell-surface antigens of melanoma recognized by human monoclonal antibodies" *Proc. Natl. Acad. Sci. USA* (1987) 84:2416-2420.

Haspel et al., "Generation of tumor cell-reactive human monoclonal antibodies using peripheral blood lymphocytes from actively immunized colorectal carcinoma patients" *Cancer Res.* (1985) 45:3951-3961.

Cote et al., "Specificity analysis of human monoclonal antibodies reactive with cell surface and intracellular antigens" *Proc. Natl. Acad. Sci. USA* (1986) 83:2959-2963.

Glassy, "Immortalization of human lymphocytes from a tumor-involved lymph node" *Cancer Res.* (1987) 47:5181-5188.

Borup-Christensen et al., "Human-human hybridomas generated with lymphocytes from patients with colorectal cancer" *Cancer Detect. Prevent. Suppl.* (1987) 1:207-215.

Kan-Mitchell et al., "Tumor-reactive human immunoglobulin G monoclonal antibody from a melanoma patient" *Cancer Res.* (1989) 49:4536-4541.

Yoshikawa et al., "Human monoclonal antibody reactive to stomach cancer produced by mouse-human hybridoma technique" *Jpn. J. Cancer Res.* (1986) 77:1122-1133.

Olsson, "Human monoclonal antibodies in experimental cancer research" *J. Nat. Cancer Inst.* (1985) 75:397-403.

Larrick et al., "Prospects for the therapeutic use of human monoclonal antibodies" *J. Biol. Response Mod.* (1986) 5:379-393.

McCabe et al., "Preclinical studies on the pharmacokinetic properties of human monoclonal antibodies to colorectal cancer and their use for detection of tumors" *Cancer Res.* (1988) 48:4348-4353.

Cohen, "Cancer vaccines get a shot in the arm" *Science* (1993) 262:841-843.

Ditzel et al., "Immunoscintigraphy of colon cancers with the human monoclonal antibody COU-1" *Cancer* (1994) 73:858-863.

Alonso, "Human-human monoclonal antibody directed against tumor surface antigen in the treatment of human malignancy" *Am. J. Clin. Oncol.* (1991) 14:463-471.

Mack et al., "A small bispecific antibody construct expressed as a functional single-chain molecule with high tumor cell cytotoxicity" *Proc. Natl. Acad. Sci. USA* (1995) 92:7021-7025.

Cheresh et al., "Disialoganglioside GD3 on human melanoma serves as a relevant target antigen for monoclonal antibody-mediated tumor cytolysis" *Proc. Natl. Acad. Sci USA* (1985) 82:5155-5159.

Cheresh et al., "Biosynthesis and expression of the disialoganglioside $G_{D2}$, a relevant target antigent on small cell lung carcinoma for monoclonal antibody-mediated cytolysis" *Cancer Res.* (1986) 46:5112-5118.

Murakami et al., "Human-human hybridomas secreting antibodies specific to human lung carcinoma" *In Vitro Cell. & Dev. Biol.* (1985) 21:593-596.

Schadendorf et al., "A novel heteromorphic human cell surface alloantigen, gp60, defined by a human monoclonal antibody" *J. Immunol.* (1989) 142:1621-1625.

Pickering et al., "Human monoclonal antibodies to cytokeratins associated with squamous cell carcinoma" *Clin. Immunol. Immunopathol.* (1984) 32:253-260.

Hagiwara et al., "Human x human hybridoma producing monoclonal antibody against autologous cervical carcinoma" *Mol. Biol. Med.* (1983) 1:245-252.

Schlom et al., "Generation of human monoclonal antibodies reactive with human mammary carcinoma cells" *Proc. Natl. Acad. Sci. USA* (1980) 77:6841-6845.

Finn et al., "MUC-1 epithelial tumor mucin-based immunity and cancer vaccines" *Immunol. Rev.* (1995) 145:61-89.

Matsumoto et al., "Clinical phase I study of human monoclonal antibody, ACA 11 (CLN-IgG) against human malignant brain tumors" *The Clinical Report* (1994) 28:118-126.

Saleh et al., "Phase II trial of murine monoclonal antibody D612 combined with recombinant human monocyte colony-stimulating factor (rhM-CSF) in patients with metastatic gastrointestinal cancer" *Cancer Res.* (1995) 55:4339-4346.

Pastan et al., "Intrathecal administration of single-chain immunotoxin, LMB-7 [B3(Fv)-PE38], produces cures of carcinomatous meningitis in a rat model" *Proc. Natl. Acad. Sci. USA* (1995) 92:2765-2769.

Chaudhuri et al., "Human monoclonal antibody developed against ovarian cancer cell surface antigen" Cancer (1994) 73:1098-1104.

Thorpe et al., Monoclonal antibody-toxin conjugates: aiming the magic bullet *Monoclonal Antibodies in Clinical Medicine* (1982) Academic Press, pp. 168-201.

Vitetta et al., "Redesigning nature's poisons to create anti-tumor reagents" *Science* (1987) 238:1098-1104.

Winter et al., "Man-made antibodies" *Nature* (1991) 349:293-299.

Olsnes et al., "Chimeric toxins" *Pharmac. Ther.* (1982) 15:355-381.

Chatal et al., "Clinical prospective study with radioiodinated monoclonal antibodies directed against colorectal cancer" *Monoclonal Antibodies for Cancer Detection and Therapy* (1985) Baldwin et al., eds., Academic Press, Chapter 8, pp. 159-180.

Jansen et al., "Efficiency and tolerance of the treatment with immuno-A-chain-toxins in human bone marrow transplantations" Monoclonal Antibodies for Cancer Detection and Therapy (1985) Baldwin et al., eds., Academic Press, Chapter 11, pp. 223-267.

Miltenyi et al. "High gradient magnetic cell separation with MACS" Cytometry (1990) 11:231-238.

Glaser et al., "Dissection of the combining site in a humanized anti-Tac antibody" *J. Immunol.* (1992) 149:2607-2614.

Tempest et al., "Reshaping a human monoclonal antibody to inhibit human respiratory syncytial virus infection *in vivo*" *Biotechnology* (1991) 9:266-271.

Shalaby et al., "Development of humanized bispecific antibodies reactive with cytotoxic lymphocytes and tumor cells overexpressing the HER2 protooncogene" *J. Exp. Med.* (1992) 175:217-225.

Levitt, "Molecular dynamics of native protein" I. Computer simulation of trajectories J. Mol. Biol. (1983) 168:595-620.

Bird et al., "Single-chain antigen-binding proteins" *Science* (1988) 242:423-426.

Posnet et al., "A novel method for producing anti-peptide antibodies" *J. Biol. Chem.* (1988) 263:1719-1725.

Tam, "High-density multiple antigen-peptide system for preparation of antipeptide antibodies" *Meth. Enz.* (1989) 168:7-15.

Fiedler et al., High level production and long-term storage of engineered antibodies in transgenic tobacco seeds Biotechnology (1995) 13:1090-1093.

Brown et al., "Chimeric parvovirus B19 capsids for the presentation of foreign epitopes" *Virol.* (1994) 198:477-488.

Miyamura et al., "Parvovirus particles as platforms for protein presentation" *Proc. Natl. Acad. Sci. USA* (1994) 91:8507-8511.

Moss, "Vaccinia virus: A tool for research and vaccine development" *Science* (1991) 252:1662-1667.

Flexner et al. "Attenuation of live recombinant vaccinia virus vectors by expression of human interleukin-2" *Vaccines 88* (1988) Cold Spring Harbor Laboratory, pp. 179-184.

Cockett et al., "High level expression of tissue inhibitor of metalloproteinases in Chinese hamster ovary cells using glutamine synthetase gene amplification" *Bio/Technology* (1990) 8:662-667.

Douillard et al., "Monoclonal antibodies specific immunotherapy of gastrointestinal tumors" *Hybridoma* (1986) 5:*Supp. 1*:S139-S149.

Diener et al., "Specific immunosuppression by immunotoxins containing daunomycin" *Science* (1986) 231:148-150.

Greiner et al., "Recombinant interferon enhances monoclonal antibody-targeting of carcinoma lesions *in vivo*"*Science* (1987) 235:895-898.

Wolff et al., "The use of monoclonal anti-$Thy_I$ $IgG_I$ for the targeting of liposomes to AKR-A cells *in vitro* and *in vivo*" *Biochem. Biophys. Acta* (1984) 802:259-273.

Brown et al., "Chimeric parvovirus B19 capsids for the presentation of foreign epitopes" *Virology* (1994) 198:477-488.

Fletcher et al., "Recent advances in the understanding of the biochemistry and clinical pharmacology of interleukin-2" *Lymphokine Res.* (1987) 6:45-57.

Rabinowich et al., "Functional analysis of mononuclear cells infiltrating into tumors: Lysis of autologous human tumor cells by cultured infiltrating lymphocytes" *Cancer Res.* (1987) 47:173-177.

Rosenberg et al., "A New approach to the adoptive immunotherapy of cancer with tumor-infiltrating lymphocytes" *Science* (1986) 233:1318-1321.

Pizz et al., "Tumour regression after intralesional injection of interleukin 2 (IL-2) in bladder cancer. Preliminary report" *Int. J. Cancer* (1984) 34:359-367.

Neuwelt et al., "Modification of the blood-brain barrier in the chemotherapy of malignant brain tumors" *FASEB J.* (1984) 43:214-219.

Baba et al., "Intracarotid infusion of leukotriene $C_4$ selectively increases blood-brain barrier permeability after focal ischemia in rats" *J. Cerebral Blood Flow Metab.* (1991) 11:638-643.

Gennuso et al., "Effect of blood-brain barrier and blood-tumor barrier modification on central nervous system liposomal uptake" *Cancer Invest.* (1993) 11:118-128.

Levin, "Relationship of octanol/water partition coefficient and molecular weight to rat brain capillary permeability" *J. Med. Chem.* (1980) 23:682-684.

Kostis et al., "Central nervous system effects of HMG CoA reductase inhibitors: Lovastatin and pravastatin on sleep and cognitive performance in patients with hypercholesterolemia" *J. Clin. Pharmacol.* (1994) 34:989-996.

Bickel et al., "Pharmacologic effects *in vivo* in brain by vector-mediated peptide drug delivery" *Proc. Natl. Acad. Sci. USA* (1993) 90:2618-2622.

Buck et al., "Production of Human Monoclonal Antibodies" *Monoclonal Antibodies and Cell Lines,* 1984, Plenum Press, New York, Chapter 11, pp. 275-308.

Ma et al., "Generation and Assembly of Secretory Antibodies in Plants" *Science* (1995) 268:716-719.

Gacesa and Ramji, *Vectors,* John Wiley & Sons, 1994. Title page & table of contents are enclosed.

Pardridge, *Peptide Drug Delivery to the Brain,* 1991, Raven Press, New York. Title page and table of contents are enclosed.

Ballou et al., "Tumor labeling in vivo using cyanine-conjugated monoclonal antibodies" *Cancer Immunol. Immunother.* (1995) 41:257-263.

Boone, C. W. et al., (1969). "Isolation of Plasma Membrane Fragments From Hela Cells," *J. Cell. Biol.* 41:378-392.

Carter, W. G. et al., (1977). "Isolation and Partial Characterization of Galactoprotein a (LETS) and Galactoprotein b From Hamster Embryo Fibroblasts," *Biochem. Biophys. Res. Commun.* 76(2):299-308.

Dunn, S. D. (1986). "Effects of the Mofidication of Transfer Buffer Composition And The Renaturation of Proteins in Gels on the Recognition of Proteins on Western Blots by Monoclonal Antibodies," *Anal. Biochem.* 157:144-153.

Hakomori, S.-I. (1989). "Aberrant Glycolsylation in Tumors and Tumor-Associated Carbohydrate Antigens," *Adv. Cancer Res.* 52:257-331.

Iida, N. et al., (1989). "A Sulfated Glucosylceramide From Rat Kidney," *J. Biol. Chem.* 264(10):5974-5980.

International Search Report mailed on Mar. 17, 1998, for PCT Patent Application No. PCT/US97/08962 filed on May 22, 1997, 5 pages.

Kean, E. L. (1968). "Rapid, Sensitive Spectrophotometric Method for Quantitative Determination of Sulfatides," *J. Lipid. Res.* 9:319-327.

Laemmli, U. K. et al., (1973). "Maturation of the Head of Bacteriophage T4. I. DNA Packaging Events," *J. Mol. Biol.* 80:575-599.

Maiti, P. K. et al., (1995). "Development and Characterization of Pancarcinoma Specific Human Monoclonal Antibody H11 (NOVOMAb-G2)," *Biotechnol.International* pp. 85-93.

McKnight et al., (1990). "Human Monoclonal Antibodies to Nuclear Antigens," *Human Antibod. Hybridoma* 1(2):77-82.

McKnight, M. et al., (Mar. 1993). "Monopharm-C, A Human Anticancer MAb: Generation, Production and Immunological Properties," *Proceedings of the American Association of Cancer Research* vol. 34, p. A 1223, Abstract No. 1330.

Novapharm Biotech Inc., (Jan. 2000). Corporate Profile, 2 pages.

Padlan, E. A. (1994). "Anatomy of the Antibody Molecule," *Molecular Immunol.* 31(3):169-217.

Press Release, (May 26, 1999). "Novopharm Biotech Inc., Announces Evidence Of Anti-Cancer Activity Utilizing Fully Human Antibodies In Pre-Clinical Animal Studies," *Novapharm Biotech,* 3 pages.

Press Release, (Oct. 7, 1999). "Anti-Cancer Treatment Shows Potential to Significantly Reduce Spread of Breast Cancer." *Novapharm Biotech,* 2 pages.

Svennerholm, L. (1957). "Quantitative Estimation of Sialic Acids. II. A Colorimetric Resorcinol-Hydrocholoric Acid Method," *Biochem. Biophys. Acta* 24:604-611.

Tadano, K. et al. (1982). "Isolation and Characterization of the Sulfated Gangliotriaosylceramide From Rat Kidney," *J. Biol. Chem.* 257(3):1482-1490.

Yiu, S. C. K. et al., (1992). "Polyisobutylmethacrylate Modifies Glycolipid Binding Specificity of Verotoxin 1 in Thin-Layer Chromatogram Overlay Procedures," *Anal. Biochem.

A) CA-46

B) H9

C) RAMOS

D) CCRF-CEM

A

B

```
                         SEQUENCE LISTING (1) GENERAL INFORMATION:

(iii) NUMBER OF SEQUENCES: 30

(2) INFORMATION FOR SEQ ID NO: 1:

(i) SEQUENCE CHARACTERISTICS:
        (A) LENGTH: 543 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..543

(xi) SEQUENCE DESCRIPTION: SEQ ID NO: 1:

CAAGCTATTT AGGTGACACT ATAGAATACT CAAGCTATGC ATCCAACGCG TTGGGAGCTC      60

TCCCATATGG TCGACCTGCA GGCGGCCGCA CTAGTGATTT CAAGCTTCAT CACTGAACAC     120

AGAGGACTCA CCATGGAGTT TGGGCTGAGC TGGGTTTTCC TCGTTGCTCT TTTAAGAGGT     180

ATCCAGTGTC AGGTGCAGCT GGTGGAGTCT GGGGGAGGCG TGGTCCAGCC TGGGAGGTCC     240

CTGAGACTCT CCTGTGCAGC CTCTGGATTC CCCTTCAGAA GCTTTGCTAT GCACTGGGTC     300

CGCCAGGCTC TAGGCAAGGG GCTGGAGTGG GTGGCAGTTA TATCATATGA TGGAAGCACT     360

AAATACTACG CAGACTCCGT GAAGGGGCGA TTCACCATCT CCAGAGACAC TTCCAAGAAC     420

ACGGTGTATC TAAAAATGAA CAGGCTGAGA ACTGAGGACA CGGCTGTCTT TTACTTGTGC     480

GAAAGACAGA GCCTGCTGGG TGACTATGAC CACTACTACG GNTTGGACGC TTGGGGAAAG     540

GGA                                                                  543

(2) INFORMATION FOR SEQ ID NO: 2:

(i) SEQUENCE CHARACTERISTICS:
        (A) LENGTH: 179 amino acids
        (B) TYPE: amino acid
```

(C) STRANDEDNESS: single
        (D) TOPOLOGY: linear (xi) SEQUENCE DESCRIPTION: SEQ ID NO: 2:

Gln Ala Ile Val Thr Leu Asn Thr Gln Ala Met His Pro Thr Arg Trp
1               5                  10                  15

Glu Leu Ser His Met Val Asp Leu Gln Ala Ala Leu Val Ile Ser
            20                  25                  30

Ser Phe Ile Thr Glu His Arg Gly Leu Thr Met Glu Phe Gly Leu Ser
            35                  40                  45

Trp Val Phe Leu Val Ala Leu Leu Arg Gly Ile Gln Cys Gln Val Gln
    50                  55                  60

Leu Val Glu Ser Gly Gly Gly Val Val Gln Pro Gly Arg Ser Leu Arg
65                  70                  75                  80

Leu Ser Cys Ala Ala Ser Gly Phe Pro Phe Arg Ser Phe Ala Met His
                85                  90                  95

Trp Val Arg Gln Ala Leu Gly Lys Gly Leu Glu Trp Val Ala Val Ile
                100                 105                 110

Ser Tyr Asp Gly Ser Thr Lys Tyr Tyr Ala Asp Ser Val Lys Gly Arg
        115                 120                 125

Phe Thr Ile Ser Arg Asp Thr Ser Lys Asn Thr Val Tyr Leu Lys Met
        130                 135                 140

Asn Arg Leu Arg Thr Glu Asp Thr Ala Val Phe Tyr Leu Cys Glu Arg
145                 150                 155                 160

Gln Ser Leu Leu Gly Asp Tyr Asp His Tyr Tyr Gly Leu Asp Ala Trp
                165                 170                 175

Gly Lys Gly (2) INFORMATION FOR SEQ ID NO: 3:

(i) SEQUENCE CHARACTERISTICS:
        (A) LENGTH: 543 base pairs
        (B) TYPE: nucleic acid
        (C) STRANDEDNESS: double
        (D) TOPOLOGY: linear (xi) SEQUENCE DESCRIPTION: SEQ ID NO: 3:

TCCCTTTCCC CAAGCGTCCA ANCCGTAGTA GTGGTCATAG TCACCCAGCA GGCTCTGTCT      60

TTCGCACAAG TAAAAGACAG CCGTGTCCTC AGTTCTCAGC CTGTTCATTT TTAGATACAC    120

CGTGTTCTTG GAAGTGTCTC TGGAGATGGT GAATCGCCCC TTCACGGAGT CTGCGTAGTA    180

TTTAGTGCTT CCATCATATG ATATAACTGC CACCCACTCC AGCCCCTTGC CTAGAGCCTG    240

GCGGACCCAG TGCATAGCAA AGCTTCTGAA GGGGAATCCA GAGGCTGCAC AGGAGAGTCT    300

CAGGGACCTC CCAGGCTGGA CCACGCCTCC CCCAGACTCC ACCAGCTGCA CCTGACACTG    360

GATACCTCTT AAAAGAGCAA CGAGGAAAAC CCAGCTCAGC CCAAACTCCA TGGTGAGTCC    420

TCTGTGTTCA GTGATGAAGC TTGAAATCAC TAGTGCGGCC GCCTGCAGGT CGACCATATG    480

GGAGAGCTCC CAACGCGTTG GATGCATAGC TTGAGTATTC TATAGTGTCA CCTAAATAGC    540

TTG                                                                  543

(2) INFORMATION FOR SEQ ID NO: 4:

(i) SEQUENCE CHARACTERISTICS:
        (A) LENGTH: 450 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..450

(xi) SEQUENCE DESCRIPTION: SEQ ID NO: 4:

CTCGAGATGG ACATGGAGTT CCAGGCGCAG CTTCTCTTCC TCCTGCTACT CTGGCTCCCA      60

GATATCACCG GAGATATTGT GTTGACGCAG TCTCCAGGCA CCCTGTCTTT GTCTCCAGGG     120

GAAAGAGCCA CCCTCTCCTG CAGGGCCAGT CAGAGTGTTA GTAGCAGCTA CTTAGCCTGG     180

TACCAGCAGA AACCTGGCCA GGCTCCCAGG CTCCTCATCT ATGGTGCATC CACCAGGGCC     240

ACTGGCATGC CAGACAGGTC CAGTGGCAGT GGGTCCGGGA CAGACTTCAC TCTCACCATC     300

AGTAGACTGG AGCCTGAAGA TTTTGCAGTG TATTACTGTC AGCAGTATGG TAGCTCACCT     360

CAGACACCTC AGATCACTTT CGGCGGAGGG ACCAAGGTGG AGATCAAACG AACTGTGGCT     420

GCACCATCTG TCTTCATCTT CCCGCCATCT                                     450

(2) INFORMATION FOR SEQ ID NO: 5:

(i) SEQUENCE CHARACTERISTICS:
        (A) LENGTH: 150 amino acids
        (B) TYPE: amino acid
        (C) STRANDEDNESS: single
        (D) TOPOLOGY: linear (xi) SEQUENCE DESCRIPTION: SEQ ID NO: 5:

Leu Glu Met Asp Met Glu Phe Gln Ala Gln Leu Leu Phe Leu Leu Leu
1               5                   10                  15

Leu Trp Leu Pro Asp Ile Thr Gly Asp Ile Val Leu Thr Gln Ser Pro
            20                  25                  30

Gly Thr Leu Ser Leu Ser Pro Gly Glu Arg Ala Thr Leu Ser Cys Arg
        35                  40                  45

Ala Ser Gln Ser Val Ser Ser Tyr Leu Ala Trp Tyr Gln Gln Lys
    50                  55                  60

Pro Gly Gln Ala Pro Arg Leu Leu Ile Tyr Gly Ala Ser Thr Arg Ala
65                  70                  75                  80

Thr Gly Met Pro Asp Arg Phe Ser Gly Ser Gly Ser Gly Thr Asp Phe
                85                  90                  95

Thr Leu Thr Ile Ser Arg Leu Glu Pro Glu Asp Phe Ala Val Tyr Tyr
            100                 105                 110

Cys Gln Gln Tyr Gly Ser Ser Pro Gln Thr Pro Gln Ile Thr Phe Gly
        115                 120                 125

Gly Gly Thr Lys Val Glu Ile Lys Arg Thr Val Ala Ala Pro Ser Val
    130                 135                 140

Phe Ile Phe Pro Pro Ser
145                 150

(2) INFORMATION FOR SEQ ID NO: 6:

(i) SEQUENCE CHARACTERISTICS:
        (A) LENGTH: 450 base pairs
        (B) TYPE: nucleic acid
        (C) STRANDEDNESS: double
        (D) TOPOLOGY: linear (xi) SEQUENCE DESCRIPTION: SEQ ID NO: 6:

AGATGGCGGG AAGATGAAGA CAGATGGTGC AGCCACAGTT CGTTTGATCT CCACCTTGGT      60

CCCTCCGCCG AAAGTGATCT GAGGTGTCTG AGGTGAGCTA CCATACTGCT GACAGTAATA     120

-continued

```
CACTGCAAAA TCTTCAGGCT CCAGTCTACT GATGGTGAGA GTGAAGTCTG TCCCGGACCC      180

ACTGCCACTG AACCTGTCTG GCATGCCAGT GGCCCTGGTG GATGCACCAT AGATGAGGAG      240

CCTGGGAGCC TGGCCAGGTT TCTGCTGGTA CCAGGCTAAG TAGCTGCTAC TAACACTCTG      300

ACTGGCCCTG CAGGAGAGGG TGGCTCTTTC CCCTGGAGAC AAAGACAGGG TGCCTGGAGA      360

CTGCGTCAAC ACAATATCTC CGGTGATATC TGGGAGCCAG AGTAGCAGGA GGAAGAGAAG      420

CTGCGCCTGG AACTCCATGT CCATCTCGAG                                      450

(2) INFORMATION FOR SEQ ID NO: 7:

(i) SEQUENCE CHARACTERISTICS:
         (A) LENGTH: 34 base pairs
         (B) TYPE: nucleic acid
         (C) STRANDEDNESS: single
         (D) TOPOLOGY: linear (xi) SEQUENCE DESCRIPTION: SEQ ID NO: 7:

TATGAAGACA CCAGGCCGAT ATTGTGTTGA CGCA                                  34

(2) INFORMATION FOR SEQ ID NO: 8:

(i) SEQUENCE CHARACTERISTICS:
         (A) LENGTH: 26 base pairs
         (B) TYPE: nucleic acid
         (C) STRANDEDNESS: single
         (D) TOPOLOGY: linear (xi) SEQUENCE DESCRIPTION: SEQ ID NO: 8:

TATCCGGATG CAGCCACAGT TCGTTT                                           26

(2) INFORMATION FOR SEQ ID NO: 9:

(i) SEQUENCE CHARACTERISTICS:
         (A) LENGTH: 26 base pairs
         (B) TYPE: nucleic acid
         (C) STRANDEDNESS: single
         (D) TOPOLOGY: linear (xi) SEQUENCE DESCRIPTION: SEQ ID NO: 9:

TATTCGGACA GGTGCAGCTG GTGGAG                                           26

(2) INFORMATION FOR SEQ ID NO: 10:

(i) SEQUENCE CHARACTERISTICS:
         (A) LENGTH: 27 base pairs
         (B) TYPE: nucleic acid
         (C) STRANDEDNESS: single
         (D) TOPOLOGY: linear (xi) SEQUENCE DESCRIPTION: SEQ ID NO: 10:

TATGGATCCT GAGGAGACGG TGACCGT                                          27

(2) INFORMATION FOR SEQ ID NO: 11:

(i) SEQUENCE CHARACTERISTICS:
         (A) LENGTH: 60 base pairs
         (B) TYPE: nucleic acid
         (C) STRANDEDNESS: single
         (D) TOPOLOGY: linear (xi) SEQUENCE DESCRIPTION: SEQ ID NO: 11:

TATATATCCG GAGGTGGTGG ATCAGGTGGA GGTGGCTCCC AGGTGCAGCT GGTGGAGTCT      60

(2) INFORMATION FOR SEQ ID NO: 12:
```

(i) SEQUENCE CHARACTERISTICS:
    (A) LENGTH: 46 base pairs
    (B) TYPE: nucleic acid
    (C) STRANDEDNESS: single
    (D) TOPOLOGY: linear (xi) SEQUENCE DESCRIPTION: SEQ ID NO: 12:

ACCTCCGGAA CCGCCACCGC CAGAGACAGA TGGTGCAGCC ACATTC                46

(2) INFORMATION FOR SEQ ID NO: 13:

(i) SEQUENCE CHARACTERISTICS:
        (A) LENGTH: 918 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: join(1..906, 913..918)

(xi) SEQUENCE DESCRIPTION: SEQ ID NO: 13:

```
GAA TTC ATG AAA AAA ACC GCT ATC GCG ATC GCA GTT GCA CTG GCT GGT       48
Glu Phe Met Lys Lys Thr Ala Ile Ala Ile Ala Val Ala Leu Ala Gly
 1               5                  10                  15

TTC GCT ACC GTT GCG CAG GCC GAT ATT GTG TTG ACG CAG TCT CCA GGC       96
Phe Ala Thr Val Ala Gln Ala Asp Ile Val Leu Thr Gln Ser Pro Gly
             20                  25                  30

ACC CTG TCT TTG TCT CCA GGG GAA AGA GCC ACC CTC TCC TGC AGG GCC      144
Thr Leu Ser Leu Ser Pro Gly Glu Arg Ala Thr Leu Ser Cys Arg Ala
         35                  40                  45

AGT CAG AGT GTT AGT AGC AGC TAC TTA GCC TGG TAC CAG CAG AAA CCT      192
Ser Gln Ser Val Ser Ser Ser Tyr Leu Ala Trp Tyr Gln Gln Lys Pro
     50                  55                  60

GGC CAG GCT CCC AGG CTC CTC ATC TAT GGT GCA TCC ACC AGG GCC ACT      240
Gly Gln Ala Pro Arg Leu Leu Ile Tyr Gly Ala Ser Thr Arg Ala Thr
 65                  70                  75                  80

GGC ATG CCA GAC AGG TTC AGT GGC AGT GGG TCC GGG ACA GAC TTC ACT      288
Gly Met Pro Asp Arg Phe Ser Gly Ser Gly Ser Gly Thr Asp Phe Thr
                 85                  90                  95

CTC ACC ATC AGT AGA CTG GAG CCT GAA GAT TTT GCA GTG TAT TAC TGT      336
Leu Thr Ile Ser Arg Leu Glu Pro Glu Asp Phe Ala Val Tyr Tyr Cys
            100                 105                 110

CAG CAG TAT GGT AGC TCA CCT CAG ACA CCT CAG ATC ACT TTC GGC GGA      384
Gln Gln Tyr Gly Ser Ser Pro Gln Thr Pro Gln Ile Thr Phe Gly Gly
        115                 120                 125

GGG ACC AAG GTG GAG ATC AAA CGA ACT GTG GCT GCA CCA TCT GTC TCT      432
Gly Thr Lys Val Glu Ile Lys Arg Thr Val Ala Ala Pro Ser Val Ser
130                 135                 140

GGC GGT GGC GGT TCC GGA GGT GGT GGA TCA GGT GGA GGT GGC TCC CAG      480
Gly Gly Gly Gly Ser Gly Gly Gly Gly Ser Gly Gly Gly Gly Ser Gln
145                 150                 155                 160

GTG CAG CTG GTG GAG TCT GGG GGA GGC GTG GTC CAG CCT GGG AGG TCC      528
Val Gln Leu Val Glu Ser Gly Gly Gly Val Val Gln Pro Gly Arg Ser
                165                 170                 175

CTG AGA CTC TCC TGT GCA GCC TCT GGA TTC CCC TTC AGA AGC TTT GCT      576
Leu Arg Leu Ser Cys Ala Ala Ser Gly Phe Pro Phe Arg Ser Phe Ala
            180                 185                 190

ATG CAC TGG GTC CGC CAG GCT CTA GGC AAG GGG CTG GAG TGG GTG GCA      624
Met His Trp Val Arg Gln Ala Leu Gly Lys Gly Leu Glu Trp Val Ala
        195                 200                 205

GTT ATA TCA TAT GAT GGA AGC ACT AAA TAC TAC GCA GAC TCC GTG AAG      672
Val Ile Ser Tyr Asp Gly Ser Thr Lys Tyr Tyr Ala Asp Ser Val Lys
```

-continued

```
Val Ile Ser Tyr Asp Gly Ser Thr Lys Tyr Tyr Ala Asp Ser Val Lys
210                 215                 220

GGC CGA TTC ACC ATC TCC AGA GAC ACT TCC AAG AAC ACG GTG TAT CTA      720
Gly Arg Phe Thr Ile Ser Arg Asp Thr Ser Lys Asn Thr Val Tyr Leu
225                 230                 235                 240

AAA ATG AAC AGC CTG AGA ACT GAG GAC ACG GCT GTC TAT TAC TGT GCG      768
Lys Met Asn Ser Leu Arg Thr Glu Asp Thr Ala Val Tyr Tyr Cys Ala
                245                 250                 255

AGA GAT CAG AGC CTG TTG GGT GAC TAT GAC CAC TAC TAC GGT TTG GAC      816
Arg Asp Gln Ser Leu Leu Gly Asp Tyr Asp His Tyr Tyr Gly Leu Asp
            260                 265                 270

GTC TGG GGC AAA GGG ACC ACG GTC ACC GTC TCC TCA GGA TCC GAA CAA      864
Val Trp Gly Lys Gly Thr Thr Val Thr Val Ser Ser Gly Ser Glu Gln
        275                 280                 285

AAA CTG ATC AGC GAA GAA GAT CTG AAC CAT CAC CAT CAC CAT              906
Lys Leu Ile Ser Glu Glu Asp Leu Asn His His His His His
    290                 295                 300

TAGTGA AAG CTT                                                       918
       Lys Leu
```

(2) INFORMATION FOR SEQ ID NO: 14:

(i) SEQUENCE CHARACTERISTICS:
        (A) LENGTH: 304 amino acids
        (B) TYPE: amino acid
        (D) TOPOLOGY: linear (ii) MOLECULE TYPE: protein (xi) SEQUENCE DESCRIPTION: SEQ ID NO: 14:

```
Glu Phe Met Lys Lys Thr Ala Ile Ala Ile Ala Val Ala Leu Ala Gly
1               5                   10                  15

Phe Ala Thr Val Ala Gln Ala Asp Ile Val Leu Thr Gln Ser Pro Gly
                20                  25                  30

Thr Leu Ser Leu Ser Pro Gly Glu Arg Ala Thr Leu Ser Cys Arg Ala
            35                  40                  45

Ser Gln Ser Val Ser Ser Ser Tyr Leu Ala Trp Tyr Gln Gln Lys Pro
        50                  55                  60

Gly Gln Ala Pro Arg Leu Leu Ile Tyr Gly Ala Ser Thr Arg Ala Thr
65                  70                  75                  80

Gly Met Pro Asp Arg Phe Ser Gly Ser Gly Ser Gly Thr Asp Phe Thr
                85                  90                  95

Leu Thr Ile Ser Arg Leu Glu Pro Glu Asp Phe Ala Val Tyr Tyr Cys
                100                 105                 110

Gln Gln Tyr Gly Ser Ser Pro Gln Thr Pro Gln Ile Thr Phe Gly Gly
            115                 120                 125

Gly Thr Lys Val Glu Ile Lys Arg Thr Val Ala Ala Pro Ser Val Ser
130                 135                 140

Gly Gly Gly Gly Ser Gly Gly Gly Ser Gly Gly Gly Gly Ser Gln
145                 150                 155                 160

Val Gln Leu Val Glu Ser Gly Gly Val Val Gln Pro Gly Arg Ser
                165                 170                 175

Leu Arg Leu Ser Cys Ala Ala Ser Gly Phe Pro Phe Arg Ser Phe Ala
            180                 185                 190

Met His Trp Val Arg Gln Ala Leu Gly Lys Gly Leu Glu Trp Val Ala
        195                 200                 205

Val Ile Ser Tyr Asp Gly Ser Thr Lys Tyr Tyr Ala Asp Ser Val Lys
210                 215                 220
```

```
Gly Arg Phe Thr Ile Ser Arg Asp Thr Ser Lys Asn Thr Val Tyr Leu
225                 230                 235                 240

Lys Met Asn Ser Leu Arg Thr Glu Asp Thr Ala Val Tyr Tyr Cys Ala
                245                 250                 255

Arg Asp Gln Ser Leu Leu Gly Asp Tyr Asp His Tyr Tyr Gly Leu Asp
            260                 265                 270

Val Trp Gly Lys Gly Thr Thr Val Thr Val Ser Ser Gly Ser Glu Gln
        275                 280                 285

Lys Leu Ile Ser Glu Glu Asp Leu Asn His His His His His Lys Leu
    290                 295                 300
```

(2) INFORMATION FOR SEQ ID NO: 15:

(i) SEQUENCE CHARACTERISTICS:
        (A) LENGTH: 918 base pairs
        (B) TYPE: nucleic acid
        (C) STRANDEDNESS: single
        (D) TOPOLOGY: linear (xi) SEQUENCE DESCRIPTION: SEQ ID NO: 15:

```
AAGCTTTCAC TAATGGTGAT GGTGATGGTT CAGATCTTCT TCGCTGATCA GTTTTTGTTC    60
GGATCCTGAG GAGACGGTGA CCGTGGTCCC TTTGCCCCAG ACGTCCAAAC CGTAGTAGTG   120
GTCATAGTCA CCCAACAGGC TCTGATCTCT CGCACAGTAA TAGACAGCCG TGTCCTCAGT   180
TCTCAGGCTG TTCATTTTTA GATACACCGT GTTCTTGGAA GTGTCTCTGG AGATGGTGAA   240
TCGGCCCTTC ACGGAGTCTG CGTAGTATTT AGTGCTTCCA TCATATGATA TAACTGCCAC   300
CCACTCCAGC CCCTTGCCTA GAGCCTGGCG GACCCAGTGC ATAGCAAAGC TTCTGAAGGG   360
GAATCCAGAG GCTGCACAGG AGAGTCTCAG GGACCTCCCA GGCTGGACCA CGCCTCCCCC   420
AGACTCCACC AGCTGCACCT GGGAGCCACC TCCACCTGAT CCACCACCTC CGGAACCGCC   480
ACCGCCAGAG ACAGATGGTG CAGCCACAGT TCGTTTGATC TCCACCTTGG TCCCTCCGCC   540
GAAAGTGATC TGAGGTGTCT GAGGTGAGCT ACCATACTGC TGACAGTAAT ACACTGCAAA   600
ATCTTCAGGC TCCAGTCTAC TGATGGTGAG AGTGAAGTCT GTCCCGGACC CACTGCCACT   660
GAACCTGTCT GGCATGCCAG TGGCCCTGGT GGATGCACCA TAGATGAGGA GCCTGGGAGC   720
CTGGCCAGGT TTCTGCTGGT ACCAGGCTAA GTAGCTGCTA CTAACACTCT GACTGGCCCT   780
GCAGGAGAGG GTGCCTCTTT CCCCTGGAGA CAAAGACAGG GTGCCTGGAG ACTGCGTCAA   840
CACAATATCG GCCTGCGCAA CGGTAGCGAA ACCAGCCAGT GCAACTGCGA TCGCGATAGC   900
GGTTTTTTTC ATGAATTC                                                918
```

(2) INFORMATION FOR SEQ ID NO: 16:

(i) SEQUENCE CHARACTERISTICS:
        (A) LENGTH: 867 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: join(1..855, 862..867)

(xi) SEQUENCE DESCRIPTION: SEQ ID NO: 16:

```
GAA TTC ATG AAA AAA ACC GCT ATC GCG ATC GCA GTT GCA CTG GCT GGT    48
Glu Phe Met Lys Lys Thr Ala Ile Ala Ile Ala Val Ala Leu Ala Gly
 1               5                  10                  15

TTC GCT ACC GTT GCG CAG GCC GAT ATT GTG TTG ACG CAG TCT CCA GGC    96
```

```
            Phe Ala Thr Val Ala Gln Ala Asp Ile Val Leu Thr Gln Ser Pro Gly
                         20                  25                  30

ACC CTG TCT TTG TCT CCA GGG GAA AGA GCC ACC CTC TCC TGC AGG GCC                144
Thr Leu Ser Leu Ser Pro Gly Glu Arg Ala Thr Leu Ser Cys Arg Ala
             35                  40                  45

AGT CAG AGT GTT AGT AGC AGC TAC TTA GCC TGG TAC CAG CAG AAA CCT                192
Ser Gln Ser Val Ser Ser Ser Tyr Leu Ala Trp Tyr Gln Gln Lys Pro
 50                  55                  60

GGC CAG GCT CCC AGG CTC CTC ATC TAT GGT GCA TCC ACC AGG GCC ACT                240
Gly Gln Ala Pro Arg Leu Leu Ile Tyr Gly Ala Ser Thr Arg Ala Thr
 65                  70                  75                  80

GGC ATG CCA GAC AGG TTC AGT GGC AGT GGG TCC GGG ACA GAC TTC ACT                288
Gly Met Pro Asp Arg Phe Ser Gly Ser Gly Ser Gly Thr Asp Phe Thr
                 85                  90                  95

CTC ACC ATC AGT AGA CTG GAG CCT GAA GAT TTT GCA GTG TAT TAC TGT                336
Leu Thr Ile Ser Arg Leu Glu Pro Glu Asp Phe Ala Val Tyr Tyr Cys
             100                 105                 110

CAG CAG TAT GGT AGC TCA CCT CAG ACA CCT CAG ATC ACT TTC GGC GGA                384
Gln Gln Tyr Gly Ser Ser Pro Gln Thr Pro Gln Ile Thr Phe Gly Gly
         115                 120                 125

GGG ACC AAG GTG GAG ATC AAA CGA ACT GTG GCT GCA TCC GGA CAG GTG                432
Gly Thr Lys Val Glu Ile Lys Arg Thr Val Ala Ala Ser Gly Gln Val
 130                 135                 140

CAG CTG GTG GAG TCT GGG GGA GGC GTG GTC CAG CCT GGG AGG TCC CTG                480
Gln Leu Val Glu Ser Gly Gly Gly Val Val Gln Pro Gly Arg Ser Leu
145                 150                 155                 160

AGA CTC TCC TGT GCA GCC TCT GGA TTC CCC TTC AGA AGC TTT GCT ATG                528
Arg Leu Ser Cys Ala Ala Ser Gly Phe Pro Phe Arg Ser Phe Ala Met
                 165                 170                 175

CAC TGG GTC CGC CAG GCT CTA GGC AAG GGG CTG GAG TGG GTG GCA GTT                576
His Trp Val Arg Gln Ala Leu Gly Lys Gly Leu Glu Trp Val Ala Val
             180                 185                 190

ATA TCA TAT GAT GGA AGC ACT AAA TAC TAC GCA GAC TCC GTG AAG GGC                624
Ile Ser Tyr Asp Gly Ser Thr Lys Tyr Tyr Ala Asp Ser Val Lys Gly
         195                 200                 205

CGA TTC ACC ATC TCC AGA GAC ACT TCC AAG AAC ACG GTG TAT CTA AAA                672
Arg Phe Thr Ile Ser Arg Asp Thr Ser Lys Asn Thr Val Tyr Leu Lys
 210                 215                 220

ATG AAC AGC CTG AGA ACT GAG GAC ACG GCT GTC TAT TAC TGT GCG AGA                720
Met Asn Ser Leu Arg Thr Glu Asp Thr Ala Val Tyr Tyr Cys Ala Arg
225                 230                 235                 240

GAT CAG AGC CTG TTG GGT GAC TAT GAC CAC TAC TAC GGT TTG GAC GTC                768
Asp Gln Ser Leu Leu Gly Asp Tyr Asp His Tyr Tyr Gly Leu Asp Val
                 245                 250                 255

TGG GGC AAA GGG ACC ACG GTC ACC GTC TCC TCA GGA TCC GAA CAA AAA                816
Trp Gly Lys Gly Thr Thr Val Thr Val Ser Ser Gly Ser Glu Gln Lys
             260                 265                 270

CTG ATC AGC GAA GAA GAT CTG AAC CAT CAC CAT CAC CAT TAGTGA AAG                 864
Leu Ile Ser Glu Glu Asp Leu Asn His His His His His         Lys
         275                 280                 285

CTT                                                                            867
Leu (2) INFORMATION FOR SEQ ID NO: 17:

(i) SEQUENCE CHARACTERISTICS:
        (A) LENGTH: 287 amino acids
        (B) TYPE: amino acid
        (D) TOPOLOGY: linear (ii) MOLECULE TYPE: protein
```

-continued (xi) SEQUENCE DESCRIPTION: SEQ ID NO: 17:

```
Glu Phe Met Lys Lys Thr Ala Ile Ala Ile Ala Val Ala Leu Ala Gly
 1               5                  10                  15

Phe Ala Thr Val Ala Gln Ala Asp Ile Val Leu Thr Gln Ser Pro Gly
                20                  25                  30

Thr Leu Ser Leu Ser Pro Gly Glu Arg Ala Thr Leu Ser Cys Arg Ala
            35                  40                  45

Ser Gln Ser Val Ser Ser Ser Tyr Leu Ala Trp Tyr Gln Gln Lys Pro
        50                  55                  60

Gly Gln Ala Pro Arg Leu Leu Ile Tyr Gly Ala Ser Thr Arg Ala Thr
 65                 70                  75                  80

Gly Met Pro Asp Arg Phe Ser Gly Ser Gly Ser Gly Thr Asp Phe Thr
                85                  90                  95

Leu Thr Ile Ser Arg Leu Glu Pro Glu Asp Phe Ala Val Tyr Tyr Cys
            100                 105                 110

Gln Gln Tyr Gly Ser Ser Pro Gln Thr Pro Gln Ile Thr Phe Gly Gly
        115                 120                 125

Gly Thr Lys Val Glu Ile Lys Arg Thr Val Ala Ala Ser Gly Gln Val
130                 135                 140

Gln Leu Val Glu Ser Gly Gly Gly Val Val Gln Pro Gly Arg Ser Leu
145                 150                 155                 160

Arg Leu Ser Cys Ala Ala Ser Gly Phe Pro Phe Arg Ser Phe Ala Met
                165                 170                 175

His Trp Val Arg Gln Ala Leu Gly Lys Gly Leu Glu Trp Val Ala Val
            180                 185                 190

Ile Ser Tyr Asp Gly Ser Thr Lys Tyr Tyr Ala Asp Ser Val Lys Gly
        195                 200                 205

Arg Phe Thr Ile Ser Arg Asp Thr Ser Lys Asn Thr Val Tyr Leu Lys
210                 215                 220

Met Asn Ser Leu Arg Thr Glu Asp Thr Ala Val Tyr Tyr Cys Ala Arg
225                 230                 235                 240

Asp Gln Ser Leu Leu Gly Asp Tyr Asp His Tyr Tyr Gly Leu Asp Val
                245                 250                 255

Trp Gly Lys Gly Thr Thr Val Thr Val Ser Ser Gly Ser Glu Gln Lys
            260                 265                 270

Leu Ile Ser Glu Glu Asp Leu Asn His His His His His Lys Leu
        275                 280                 285
```

(2) INFORMATION FOR SEQ ID NO: 18:

(i) SEQUENCE CHARACTERISTICS:
        (A) LENGTH: 867 base pairs
        (B) TYPE: nucleic acid
        (C) STRANDEDNESS: single
        (D) TOPOLOGY: linear (xi) SEQUENCE DESCRIPTION: SEQ ID NO: 18:

```
AAGCTTTCAC TAATGGTGAT GGTGATGGTT CAGATCTTCT TCGCTGATCA GTTTTTGTTC     60

GGATCCTGAG GAGACGGTGA CCGTGGTCCC TTTGCCCCAG ACGACCAAAC CGTAGTAGTG    120

GTCATAGTCA CCCAACAGGC TCTGATCTCT CGCACAGTAA TAGACAGCCG TGTCCTCAGT    180

TCTCAGGCTG TTCATTTTTA GATACACCGT GTTCTTGGAA GTGTCTCTGG AGATGGTGAA    240

TCGGCCCTTC ACGGAGTCTG CGTAGTATTT AGTGCTTCCA TCATATGATA TAACTGCCAC    300

CCACTCCAGC CCCTTGCCTA GAGCCTGGCG GACCCAGTGC ATAGCAAAGC TTCTGAAGGG    360
```

```
GAATCCAGAG GCTGCACAGG AGAGTCTCAG GGACCTCCCA GGCTGGACCA CGCCTCCCCC    420

AGACTCCACC AGCTGCACCT GTCCGGATGC AGCCACAGTT CGTTTGATCT CCACCTTGGT    480

CCCTCCGCCG AAAGTGATCT GAGGTGTCTG AGGTGAGCTA CCATACTGCT GACAGTAATA    540

CACTGCAAAA TCTTCAGGCT CCAGTCTACT GATGGTGAGA GTGAAGTCTG TCCCGGACCC    600

ACTGCCACTG AACCTGTCTG GCATGCCAGT GGCCCTGGTG GATGCACCAT AGATGAGGAG    660

CCTGGGAGCC TGGCCAGGTT TCTGCTGGTA CCAGGCTAAG TAGCTGCTAC TAACACTCTG    720

ACTGGCCCTG CAGGAGAGGG TGGCTCTTTC CCCTGGAGAC AAAGACAGGG TGCCTGGAGA    780

CTGCGTCAAC ACAATATCGG CCTGCGCAAC GGTAGCGAAA CCAGCCAGTG CAACTGCGAT    840

CGCGATAGCG GTTTTTTTCA TGAATTC                                       867
```

(2) INFORMATION FOR SEQ ID NO: 19:

(i) SEQUENCE CHARACTERISTICS:
        (A) LENGTH: 5 amino acids
        (B) TYPE: amino acid
        (D) TOPOLOGY: linear (ii) MOLECULE TYPE: protein (ix) FEATURE:
        (A) NAME/KEY: Modified Base
        (B) LOCATION: 5
        (D) OTHER INFORMATION: May also be Thr.

(xi) SEQUENCE DESCRIPTION: SEQ ID NO: 19:

Phe His Arg Tyr Ser
            5

(2) INFORMATION FOR SEQ ID NO: 20:

(i) SEQUENCE CHARACTERISTICS:
        (A) LENGTH: 7 amino acids
        (B) TYPE: amino acid
        (D) TOPOLOGY: linear (ii) MOLECULE TYPE: protein (xi) SEQUENCE DESCRIPTION: SEQ ID NO: 20:

Phe His Arg Tyr Ser Leu Pro
            5

(2) INFORMATION FOR SEQ ID NO: 21:

(i) SEQUENCE CHARACTERISTICS:
        (A) LENGTH: 7 amino acids
        (B) TYPE: amino acid
        (D) TOPOLOGY: linear (ii) MOLECULE TYPE: protein (xi) SEQUENCE DESCRIPTION: SEQ ID NO: 21:

Phe His Arg Tyr Ser Asp Tyr
            5

(2) INFORMATION FOR SEQ ID NO: 22:

(i) SEQUENCE CHARACTERISTICS:
        (A) LENGTH: 7 amino acids
        (B) TYPE: amino acid
        (D) TOPOLOGY: linear (ii) MOLECULE TYPE: protein (xi) SEQUENCE DESCRIPTION: SEQ ID NO: 22:

Phe His Arg Tyr Ser Leu Pro
                5

(2) INFORMATION FOR SEQ ID NO: 23:

(i) SEQUENCE CHARACTERISTICS:
        (A) LENGTH: 7 amino acids
        (B) TYPE: amino acid
        (D) TOPOLOGY: linear (ii) MOLECULE TYPE: protein (xi) SEQUENCE DESCRIPTION: SEQ ID NO: 23:

Phe His Arg Tyr Ser Pro Thr
                5

(2) INFORMATION FOR SEQ ID NO: 24:

(i) SEQUENCE CHARACTERISTICS:
        (A) LENGTH: 7 amino acids
        (B) TYPE: amino acid
        (D) TOPOLOGY: linear (ii) MOLECULE TYPE: protein (xi) SEQUENCE DESCRIPTION: SEQ ID NO: 24:

Phe His Arg Tyr Thr Pro Gly
                5

(2) INFORMATION FOR SEQ ID NO: 25:

(i) SEQUENCE CHARACTERISTICS:
        (A) LENGTH: 7 amino acids
        (B) TYPE: amino acid
        (D) TOPOLOGY: linear (ii) MOLECULE TYPE: protein (xi) SEQUENCE DESCRIPTION: SEQ ID NO: 25:

Phe His Arg Tyr Ser Leu Pro
                5

(2) INFORMATION FOR SEQ ID NO: 26:

(i) SEQUENCE CHARACTERISTICS:
        (A) LENGTH: 7 amino acids
        (B) TYPE: amino acid
        (D) TOPOLOGY: linear (ii) MOLECULE TYPE: protein (xi) SEQUENCE DESCRIPTION: SEQ ID NO: 26:

Phe His Arg Tyr Ser Pro Thr
                5

(2) INFORMATION FOR SEQ ID NO: 27:

(i) SEQUENCE CHARACTERISTICS:
        (A) LENGTH: 7 amino acids
        (B) TYPE: amino acid
        (D) TOPOLOGY: linear (ii) MOLECULE TYPE: protein (xi) SEQUENCE DESCRIPTION: SEQ ID NO: 27:

Phe His Arg Tyr Ser Leu Pro
                5

(2) INFORMATION FOR SEQ ID NO: 28:

(i) SEQUENCE CHARACTERISTICS:
        (A) LENGTH: 7 amino acids
        (B) TYPE: amino acid
        (D) TOPOLOGY: linear (ii) MOLECULE TYPE: protein (xi) SEQUENCE DESCRIPTION: SEQ ID NO: 28:

Met His Arg Tyr Thr Pro Leu
                    5

(2) INFORMATION FOR SEQ ID NO: 29:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO: 29:

Phe His Lys Tyr Ser
                5

(2) INFORMATION FOR SEQ ID NO: 30:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO: 30:

Tyr His Lys Tyr Ser
                5

ANTIGEN BINDING FRAGMENTS THAT SPECIFICALLY DETECT CANCER CELLS, NUCLEOTIDES ENCODING THE FRAGMENTS, AND USE THEREOF FOR THE PROPHYLAXIS AND DETECTION OF CANCERS

CROSS-REFERENCE TO RELATED APPLICATIONS

This application is the U.S. National Phase of international application PCT/US97/08972, filed on 22 May 1997, which claims priority to U.S. application Ser. No. 08/657,449, which was filed 22 May 1996.

TECHNICAL FIELD

This invention relates to antibodies specific to an antigen detected on neoplastic cells but not on normal cells. This antigen is termed herein the "C-antigen." The C-antigen is recognized by the human monoclonal antibody (Mab) termed "H11." The invention encompasses a wide variety of antibodies, and functional derivatives thereof that retain the immunologic specificity of H11 and are termed herein "αC." The exemplary antibody, H11, compositions comprising the H11, and hybridomas producing H11 are included herein. The H11 V region polynucleotides and polypeptides encoded thereby and recombinant molecules containing these polynucleotides are also encompassed by the invention. Methods of use including therapeutic and diagnostic of the αC antibodies are also included in the invention.

BACKGROUND ART

In spite of numerous advances in medical research, cancer remains the second leading cause of death in the United States. In the industrialized nations, roughly one in five persons will die of cancer. Traditional modes of clinical care, such as surgical resection, radiotherapy and chemotherapy, have a significant failure rate, especially for solid tumors. Failure occurs either because the initial tumor is unresponsive, or because of recurrence due to regrowth at the original site and/or metastases. Even in cancers such as breast cancer where the mortality rate has decreased, successful intervention relies on early detection of the cancerous cells. The etiology, diagnosis and ablation of cancer remain a central focus for medical research and development.

Neoplasia resulting in benign tumors can usually be completely cured by removing the mass surgically. If a tumor becomes malignant, as manifested by invasion of surrounding tissue, it becomes much more difficult to eradicate. Once a malignant tumor metastasizes, it is much less likely to be eradicated.

The three major cancers, in terms of morbidity and mortality, are colon, breast and lung. New surgical procedures offer an increased survival rate for colon cancer. Improved screening methods increase the detection of breast cancer, allowing earlier, less aggressive therapy. Numerous studies have shown that early detection increases survival and treatment options. Lung cancer remains largely refractory to treatment.

Excluding basal cell carcinoma, there are over one million new cases of cancer per year in the United States alone, and cancer accounts for over one half million deaths per year in this country. In the world as a whole, the five most common cancers are those of lung, stomach, breast, colon/rectum, and uterine cervix, and the total number of new cases per year is over 6 million. Only about half the number of people who develop cancer die of it.

Melanoma is one of the human diseases for which there is an acute need of new therapeutic modalities. It is a particularly aggressive form of skin cancer, and occurs in increased frequency in individuals with regular unguarded sun exposure. In the early disease phases, melanoma is characterized by proliferation at the dermal-epidermal junction, which soon invades adjacent tissue and metastasizes widely. Once it has metastasized, it is often impossible to extirpate and is consequently fatal. Worldwide, 70,000 patients are diagnosed with melanoma and it is responsible for 25,000 reported deaths each year. The American Cancer Society projects that by the year 2000, 1 out of every 75 Americans will be diagnosed with melanoma.

Neuroblastoma is a highly malignant tumor occurring during infancy and early childhood. Except for Wilm's tumor, it is the most common retroperitoneal tumor in children. This tumor metastasizes early, with widespread involvement of lymph nodes, liver, bone, lung, and marrow. While the primary tumor is resolvable by resection, the recurrence rate is high.

An estimated 178,100 new cases of lung cancer will be diagnosed in 1997, accounting for 13% of cancer diagnoses. An estimated 160,400 deaths due to lung cancer will occur in 1997 accounting for 29% of all cancer deaths. The one year survival rates for lung cancer have increased from 32% in 1973 to 41% in 1993, largely due to improvements in surgical techniques. The 5 year survival rate for all stages combined is only 14%. The survival rate is 48% for cases detected when the disease is still localized, but only 15% of lung cancers are discovered that early.

Small cell lung cancer is the most malignant and fastest growing form of lung cancer and accounts for 20–25% of new cases of lung cancer. 60,000 cases will be diagnosed in the U.S. in 1996. The primary tumor is generally responsive to chemotherapy, but is followed by wide-spread metastasis. The median survival time at diagnosis is approximately 1 year, with a 5 year survival rate of 5–10%.

Breast cancer is one of the most common cancers and is the third leading cause of death from cancers in the United States with an annual incidence of about 180,200 new cases among women in the United States during 1997. About 1,400 new cases of breast cancer will be diagnosed in men in 1997. In industrialized nations, approximately one in eight women can expect to develop breast cancer. The overall mortality rate for breast cancer has remained unchanged since 1930. It has increased an average of 0.2% per year, but decreased in women under 65 years of age by an average of 0.3% per year. Preliminary data suggest that breast cancer mortality may be beginning to decrease, probably as a result of increased diagnoses of localized cancer and carcinoma in situ. See e.g., Marchant (1994) Contemporary Management of Breast Disease 11: Breast Cancer, in: *Obstetrics and Gynecology Clinics of North America* 21:555–560; and Colditz (1993) *Cancer Suppl.* 71:1480–1489. An estimated 44,190 deaths (43,900 women, 290 men) in 1997 will occur due to breast cancer. In women, it is the second major cause of cancer death after lung cancer. The five-year survival rate for localized breast cancer has increased from 72% in the 1940s to 97% today. If the cancer has spread regionally, however, the rate is 76%, and for women with distant metastases the rate is 20%. Survival after a diagnosis of breast cancer continues to decline beyond five years. Sixty-five percent of women diagnosed with breast cancer survive 10 years and 56% survive 15 years.

Non-Hodgkin's B cell lymphomas are cancers of the immune system that are expected to afflict approximately 225,000 patients in the United States in 1996. These cancers are diverse with respect to prognosis and treatment, and are generally classified into one of three grades. The median survival of the lowest grade is 6.6 years and the higher grade cancers have much lower life expectancy. Virtually all non-Hodgkin's B cell lymphomas are incurable. New diagnoses of non-Hodgkins lymphomas have increased approximately 7% annually over the past decade, with 52,700 new diagnoses estimated for 1996. The increase is due in part to the increasing prevalence of lymphomas in the AIDS patient population.

Colon and rectal cancer will account for an estimated 131,200 cases in 1997, including 94,100 of colon cancer and 37,100 of rectal cancer. Colorectal cancers account for about 9% of new cancer diagnoses. An estimated 54,900 deaths due to colorectal cancer will occur in 1997, accounting for about 10% of cancer deaths. Mortality rates for colorectal cancer have fallen 32% for women and 14% for men during the past 20 years, reflecting decreasing incidence rates and increasing survival rates. However, the mortality rate in African American men continues to rise. The 1 and 5 year relative survival rates for patients with colon and rectal cancer are 82% and 61%, respectively. When colorectal cancers are detected in an early, localized stage, the 5 year survival rate is 91%; however, only 37% of colorectal cancers are discovered at that stage. After the cancer has spread regionally to involve adjacent organs or lymph nodes, the rate drops to 63%. Survival rates for persons with distant metastases is 7%. Survival continues to decline beyond 5 years, and 50% survive 10 years.

In spite of the difficulties, effective cures using anticancer drugs (alone or in combination with other treatments) have been devised for some formerly highly lethal cancers. Most notable among these are Hodgkin's lymphoma, testicular cancer, choriocarcinoma, and some leukemias and other cancers of childhood. For several of the more common cancers, early diagnosis, appropriate surgery or local radiotherapy enables a large proportion of patients to recover.

Current methods of cancer treatment are relatively non-selective. Surgery removes the diseased tissue, radiotherapy shrinks solid tumors and chemotherapy kills rapidly dividing cells. Chemotherapy, in particular, results in numerous side effects, in some cases so severe to preclude the use of potentially effective drugs. Moreover, cancers often develop resistance to chemotherapeutic drugs.

Numerous efforts are being made to enhance the specificity of cancer therapy. For review, see Kohn and Liotta (1995) *Cancer Res.* 55:1856–1862. In particular, identification of cell surface antigens expressed exclusively or preferentially on certain tumors allows the formulation of more selective treatment strategies. Antibodies directed to these antigens have been used in immunotherapy of several types of cancer.

The basic immunoglobulin (Ig) structural unit in vertebrate systems is composed of two identical light ("L") polypeptide chains (approximately 23 kDa), and two identical heavy ("H") chains (approximately 53 to 70 kDa). The four chains are joined by disulfide bonds in a "Y" configuration. At the base of the Y, the two H chains are bound by covalent disulfide linkages.

FIG. 1 shows a schematic of an antibody structure. The L and H chains are each composed of a variable (V) region at the N-terminus, and a constant (C) region at the C-terminus. In the L chain, the V region (termed "$V_LJ_L$") is composed of a V ($V_L$) region connected through the joining ($J_L$) region to the C region ($C_L$). In the H chain, the V region ($V_HD_HJ_H$) is composed of a variable ($V_H$) region linked through a combination of the diversity ($D_H$) region and the joining ($J_H$) region to the C region ($C_H$). The $V_LJ_L$ and $V_HD_HJ_H$ regions of the L and H chains, respectively, are associated at the tips of the Y to form the antigen binding portion and determine antigen binding specificity.

The ($C_H$) region defines the isotype, i.e. the class or subclass of antibody. Antibodies of different isotypes differ significantly in their effector functions, such as the ability to activate complement, bind to specific receptors (e.g., Fc receptors) present on a wide variety of cell types, cross mucosal and placental barriers, and form polymers of the basic four-chain IgG molecule.

Antibodies are categorized into "classes" according to the $C_H$ type utilized in the immunoglobulin molecule (IgM, IgG, IgD, IgE, or IgA). There are at least five types of $C_H$ genes (Cμ, Cγ, Cδ, Cε, and Cα), and some species have multiple $C_H$ subtypes (e.g., $C\gamma_1$, $C\gamma_2$, $C\gamma_3$, and $C\gamma_4$, in humans). There are a total of nine $C_H$ genes in the haploid genome of humans, eight in mouse and rat, and several fewer in many other species. In contrast, there are normally only two types of L chain C regions ($C_L$), kappa (κ) and lambda (λ), and only one of these C regions is present in a single L chain protein (i.e., there is only one possible L chain C region for every $V_LJ_L$ produced). Each H chain class can be associated with either of the L chain classes (e.g., a $C_H\gamma$ region can be present in the same antibody as either a κ or λ L chain), although the C regions of the H and L chains within a particular class do not vary with antigen specificity (e.g., an IgG antibody always has a Cγ H chain C region regardless of the antigen specificity).

Each of the V, D, J, and C regions of the H and L chains are encoded by distinct genomic sequences. Antibody diversity is generated by recombination between the different $V_H$, $D_H$, and $J_H$, gene segments in the H chain, and $V_L$ and $J_L$ gene segments in the L chain. The recombination of the different $V_H$, $D_H$, and $J_H$ genes is accomplished by DNA recombination during B cell differentiation. Briefly, the H chain sequence recombines first to generate a $D_HJ_H$ complex, and then a second recombinatorial event produces a $V_HD_HJ_H$ complex. A functional H chain is produced upon transcription followed by splicing of the RNA transcript. Production of a functional H chain triggers recombination in the L chain sequences to produce a rearranged $V_LJ_L$ region which in turn forms a functional $V_LJ_LC_L$ region, i.e., the functional L chain.

The value and potential of antibodies as diagnostic and therapeutic reagents has been long-recognized in the art. Unfortunately, the field has been hampered by the slow, tedious processes required to produce large quantities of an antibody of a desired specificity. The classical cell fusion techniques allowed for efficient production of Mabs by fusing the B cell producing the antibody with an immortalized cell line. The resulting cell line is a hybridoma cell line.

Antibodies and functional derivatives thereof have been used in a variety of clinical settings. For instance, digoxin-specific Fab antibody fragments were used to treat life-threatening digitalis intoxication. Antibodies are becoming more routinely useful in diagnostic techniques such as radioimmune diagnosis of colon cancers. Koda et al. (1995) *Am. J. Gastroenterol.* 90:1644. A number of uses of Mabs, previously thought to be untenable, have recently been put into practice. For instance, see Hall (1995) *Science* 279: 915–916.

A number of autoantibodies (antibodies that recognize and bind to self antigens) are found in humans. Many of these are associated with particular diseases such as rheumatoid arthritis, systemic lupus erythematosus, myasthenia gravis, primary biliary cirrhosis, polymyositis, systemic vasculitis, idiopathic necrotizing and crescentic glomerulonephritis and amyotrophic lateral sclerosis. For review, see Shattner (1986/1987) *Immunol. Lett.* 14:143–153. Other autoantibodies are naturally-occurring. Lutz and Wipp (1982) *J. Immunol.* 128:1965; and Guilbert et al. (1982) *J. Immunol.* 128:2779–2787. Recently, human autoantibodies to specific cancer antigens have been detected and, in some cases, are being produced by hybridoma technology. These antibodies have also been produced by active immunization. U.S. Pat. No. 5,474,755. Originally, the human B cells were immortalized using Epstein-Barr Virus or mouse myelomas. For review, see Buck et al. (1984) "Monoclonal Antibodies" NY, Plenum Press. More recent techniques have allowed immortalization without the use of this potentially harmful virus. See, e.g., U.S. Pat. No. 4,618,477; and Glassy (1987) *Cancer Res.* 47:5181–5188. In most instances, the antibodies are specific for one, or in some instances, a few, cancer types. For instance, a Mab has been described that 1:5 specifically recognizes glioma cells but no other tumor or normal cells. These antibodies were used to image the glioma in the patient's brain. Fischer et al. (1991) *Immunobiol. Prot. Pep. VI* (M. Atassi, ed.) Plenum Press, NY. pp. 263–270. No antibody has been described that is capable of recognizing a wide range of tumors while failing to recognize, or only poorly recognize, normal, non-cancerous cells.

Recombinant genetic techniques have allowed cloning and expression of antibodies, functional fragments thereof and the antigens recognized. These engineered antibodies provide novel methods of production and treatment modalities. For instance, functional immunoglobulin fragments have been expressed in bacteria and transgenic tobacco seeds and plants. Skerra (1993) *Curr. Opin. Immunol.* 5:256–262; Fiedler and Conrad (1995) *Bio/Technology* 13:1090–1093; Zhang et al. (1993) *Cancer Res.* 55:3384–3591; Ma et al. (1995) *Science* 268:916; and, for a review of synthetic antibodies, see Barbas (1995) *Nature Med.* 1:836–839.

Several human Mabs against tumor associated antigens have been produced and characterized. The tumor associated antigens recognized by human Mabs include cell surface, cytoplasmic and nuclear antigens. Yoshikawa et al. (1989) *Jpn. J. Cancer Res.* (Gann) 80:546–553; Yamaguchi et al. (1987) *Proc. Natl. Acad. Sci. USA* 84:2416–2420; Haspel et al. (1985) *Cancer Res.* 45:3951–3961; Cote et al. (1986) *Proc. Natl. Acad. Sci. USA* 83:2959–2963; Glassy (1987) *Cancer Res.* 47:5181–5188; Borup-Christensen et al. (1987) *Cancer Detect. Prevent. Suppl.* 1:207–215; Haspel et al. (1985) *Cancer Res.* 45:3951–3961; Kan-Mitchell et al. (1989) *Cancer Res.* 49:45364541; Yoshikawa et al. (1986) *Jpn. J. Cancer Res.* 77:1122–1133; and McKnight et al. (1990) *Human Antibod. Hybridomas* 1: 125–129.

Human Mabs have been used in cancer imaging, diagnosis and therapy. Olsson (1985) *J. Nat. Cancer Inst.* 75:397–404; Larrick and Bourla (1986)*J. Biol. Resp. Mod.* 5:379–393; McCabe et al. (1988) *Cancer Res.* 48:4348–4353; Research News (1993) *Science* 262:841; Ditzel et al. (1994) *Cancer* 73:858–863; and Alonso (1991) *Am. J. Clin. Oncol.* 4:463–471. A recombinant single chain bispecific antibody has been reported that has high tumor cell toxicity. This molecule recognizes both the CD3 antigen of human T cells and EpCAM, which is associated with disseminated tumor cells in patients with minimal residual colorectal cancer. Mack et al. (1995) *Proc. Natl. Acad. Sci. USA* 92:7021–7025.

Several murine monoclonal anti-GD2 antibodies were reported to suppress the growth of tumors of neuroectodermal origin in athymic (nu/nu) mice or cause remission in patients with metastatic melanoma. A human-mouse chimeric anti-GD2 antibody caused remission in patients with metastatic neuroblastoma. The mechanism of action of the antibodies is thought to involve antibody dependent cellular cytotoxicity (ADCC) or complement-mediated cytotoxicity (CMC). Clinical responses have been obtained by treating melanoma with Mabs against GM2, GD2 and GD3. Cheresh et al. (1985) *Proc. Natl. Acad. Sci. USA* 82:5155–5159. Active immunization with a ganglioside vaccine comprising GM2 produced anti-GM2 antibodies in 50/58 patients, who survived longer on average than patients without detectable anti-GM2 antibody.

Mabs to GD2 have also been found to react specifically with small cell lung carcinoma. Cheresh et al. (1986) *Cancer Res.* 46:5112–5118. Human Mabs specific for other cancers including lung, melanoma, stomach, squamous cell carcinoma, cervical carcinoma, and mammary carcinoma have also been produced. Murakami (1985) *in Vitro Cell. Dev. Biol.* 21:593; Schadendorf (1989) *J. Immunol.* 142:1621–1625; Yoshikawa et al. (1986) *Jpn. J. Cancer Res.* 77:1122–1133; Pickering and Misra (1984) *Clin. Immunol. Immunopathol.* 32:253–260; Hagiwara and Sato (1983) *Mol. Biol. Med.* 1:245–252; and Schlom et al. (1980) *Proc. Natl. Acad. Sci. USA* 77:6841–6845. Human anti-cancer Mabs and the antigens they recognize have also been suggested for use in vaccines. See, e.g. Finn et al. (1995) *Immunol. Rev.* 145:61–89. A human Mab to malignant brain tumors was used in a phase I clinical trial without adverse side effects. Matsumoto et al. (1994) *The Clinical Report* 28:118–126. Phase II trial results have been reported on combined treatment with murine Mab and colony stimulating factor in metastatic gastrointestinal cancer. Saleh et al. (1995) *Cancer Res.* 55:4339–4346. A single chain immunotoxin has also been found to cure carcinomatous meningitis in a rat model. Pastan et al. (1995) *Proc. Natl. Acad. Sci. USA* 92:2765–2769. Human Mabs that specifically recognize ovarian cancer cells have been shown to effectively image this cancer. Chaudhuri et al. (1994) *Cancer* 73: 1098–1104.

If there were a simple and reliable strategy for providing immune reactivity against an antigen common to these cancers rather than cancer-specific immunity, the clinical prospects of cancers in general would improve. All references cited herein are hereby incorporated by reference in their entirety.

DISCLOSURE OF THE INVENTION

This invention encompasses compositions containing antigen binding fragments of an antibody where the antibody specifically recognizes the antigen recognized by an antibody comprising a H chain V region having the amino acid sequence of SEQ ID NO:2 and a L chain V region having the amino acid sequence of SEQ ID NO:4. Preferably, the antibody is H11. The invention further encompasses antibodies comprising the H and L chain V regions of H11 (SEQ ID NOS:2 and 4, respectively). H11 specifically recognizes cancer cells from a wide variety of cancers but does not recognize normal, non-cancerous cells. By "does not recognize" is meant that noncancer cells are either not specifically bound to by H11 or are only poorly recognized by the antibody. The antibodies are designated αC and include H11 and any antibody with the "immunologic specificity" of H11, that is, recognizing the antigen recognized by H11, and that is specific for at least one type of cancer cell but does not recognize normal cells. These antigen binding fragments include, but are not limited to, whole native antibodies, exemplified by H11; bispecific antibodies; chimeric antibodies; Fab, Fab', single chain V region fragments (scFv) and fusion polypeptides.

The invention further encompasses H11 antibody fusion molecules comprising a polypeptide region with an antigenic, therapeutic, toxic or labeling molecule attached to the H chain C region, a single-chain $V_H$-$V_L$ or $V_L$-$V_H$ V region, and polynucleotides encoding such polypeptides.

Also embodied in the invention are polypeptides having the immunologic specificity of H11, wherein the polypeptide comprises at least 5 consecutive amino acids from a V region of an αC antibody. The V region may be from a L chain or H chain. The 5 consecutive amino acids preferably play a role in immunologic specificity, and may be from a CDR (Complementarity Determining Region of an antibody). Intact H11, functionally active fragments of H11, fusion proteins, chimeric antibodies, multiple antigen proteins, and other polypeptide derivatives of αC antibodies are included. Of special interest are single-chain V regions and fusion proteins.

The compounds and compositions of this invention may be used inter alia for detecting or treating a cancer; including therapy of such cancer, and prophylactic care, particularly for decreasing the risk of recurrence.

The invention further embodies cells and cell lines producing the αC antigen binding fragments.

Another embodiment of this invention is a polynucleotide comprising a sequence encoding a polypeptide with the immunologic specificity of H11, wherein the encoded polypeptide comprises at least 5 consecutive amino acids from a V region of H11. The V region may be from either the H11 L chain or H chain. The 5 consecutive amino acids preferably play a role in H11 immunologic reactivity, and may be from a CDR. The V region of H11 has been found to have a small region of homology to an antibody designated A6. Peptides comprised solely of this region of homology and lacking other H11-specific amino acid residues are specifically excluded from the claimed invention. A6 is described in WO953574.

The invention also encompasses isolated polynucleotides of at least 20 consecutive nucleotides capable of forming a stable duplex with the H11 L or H chain encoding sequences, but not with sequences for other previously described immunoglobulin molecules. Any of these polynucleotides may be in the form of cloning vectors, expression vectors, or transfected into host cells.

A further embodiment of this invention comprises prophylactic treatment of a cancer patient with at least one αC antigen binding fragment. Preferably, αC is fused to a therapeutic molecule to effect delivery of the therapeutic molecule to the cancer cell. The individual may have a clinically detectable tumor, or the tumor may have been previously treated and rendered undetectable. The method may be for palliating the disease, or for reducing the risk of recurrence.

A further embodiment of the invention is a kit for detection or quantitation of the antigen recognized by αC (hereinafter, the "C-antigen") in a sample, comprising H11 or a polypeptide of this invention in suitable packaging. Also embodied by the invention are methods for detecting the C-antigen or cells expressing the C-antigen by employing a reagent or kit embodied in this invention.

BEST MODE FOR CARRYING OUT THE INVENTION

Figure 1:
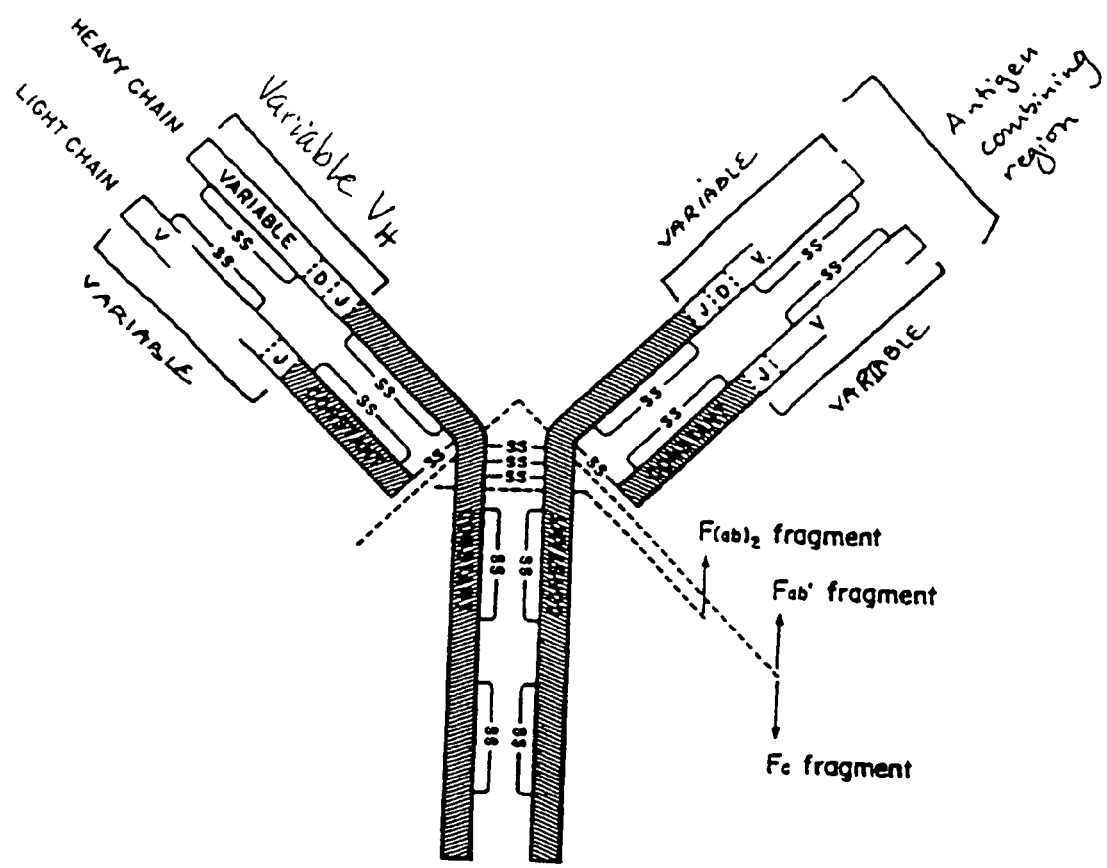
FIG. 1 depicts a schematic of the general antibody structure.

This invention encompasses antigen binding fragments exemplified by a newly identified human Mab that recognizes specifically cancerous cells. This specificity extends only to cancer cells, and the antibody does not recognize non-cancerous cells. The exemplary antibody is designated H11 and the variable regions are encoded by SEQ ID NOS: 1 and 4 (SEQ ID NOS:3 and 6 being the complementary strands of 1 and 4, respectively) and recognizes the antigen designated "C-antigen." The specificity of H11 includes, but is not limited to, glioblastoma, neuroblastoma, malignant melanoma, breast adenocarcinoma, lung adenocarcinoma, small cell lung carcinoma, colon adenocarcinoma and prostate adenocarcinoma.

As shown in the examples herein, H11 and H11-scFv do not recognize non-cancerous cells from all normal tissues tested. H11 and αC antigen binding fragments are therefore useful in palliating the clinical conditions related to a wide variety of cancers. The invention comprises antigen binding fragments recognizing the antigen H11 is specific for (designated C antigen). The invention further comprises polypeptide derivatives of H11 and methods for using these compositions in diagnosis, treatment, and manufacture of novel reagents. The invention further encompasses polynucleotides encoding αC, H 11 and derivatives thereof. Methods of use thereof are also encompassed by the invention.

The invention further encompasses αC derivatives with immunologic specificity for the C-antigen. These derivatives comprise regions of the polypeptide sequence comprising part of the H11 VDJ junction. Also encompassed are regions spanning at least one, preferably 2, and more preferably 3 or more of the H11 CDR amino acid sequences.

The full sequences of the H11 L and H chain C regions have not been determined, but are expected to be identical or nearly identical to those of other human immunoglobulin molecules. Further, knowledge of the V region amino acid sequences allows subcloning with any C region. Such subcloning techniques are well known in the art. The chimeric molecules produced by these cloning techniques are also encompassed by the invention.

Screening a commercial heptapeptide phage library with H11 IgM and scFv antibody clones has shown a very strong consensus sequence at the N-terminus having the following amino acid sequence: Phe-His-Arg-Tyr-Ser/Thr. The results are shown in Table 1.

TABLE 1

| IgM H11 pannings | M1 Phe-His-Arg-Tyr-Ser-Leu-Pro SEQ ID NO: 20 |
| --- | --- |
| | M2 Phe-His-Arg-Tyr-Ser-Asp-Tyr SEQ ID NO: 21 |
| | M3 Phe-His-Arg-Tyr-Ser-Leu-Pro SEQ ID NO: 22 |
| | M4 Phe-His-Arg-Tyr-Ser-Pro-Thr SEQ ID NO: 23 |
| | M7 Phe-His-Arg-Tyr-Thr-Pro-Gly SEQ ID NO: 24 |
| | M8 Phe-His-Arg-Tyr-Ser-Leu-Pro SEQ ID NO: 25 |
| | M10 Phe-His-Arg-Tyr-Ser-Pro-Thr SEQ ID NO: 26 |
| sfFv H11 pannings | S2 Phe-His-Arg-Tyr-Ser-Leu-Pro SEQ ID NO: 27 |
| | S5 Met-His-Arg-Tyr-Thr-Pro-Leu SEQ ID NO: 28 |

The DNA sequences use multiple codons, indicating quite different phage origins. For example, the Arg is coded by triplets CGx and AGx families. In addition, comparison of the H11 pentapeptide consensus with sequence databases showed homology to the S100 family of $Ca^{2+}$ binding proteins. The results are shown in Table 2.

TABLE 2

| H11 pentapeptide | Phe-His-Arg-Tyr-Ser/Thr SEQ ID NO: 19 |
| --- | --- |
| S. griseus protein | Phe-His-Arg-Tyr-Ser (amino acids 251–255) SEQ ID NO: 19 |
| Peanut stunt virus | Phe-His-Arg-Tyr-Ser (amino acids 540–544) SEQ ID NO: 19 |
| Human calcyclin | Phe-His-Lys-Tyr-Ser (amino acids 16–20) SEQ ID NO: 29 |
| Cystic Fibrosis Ag | Tyr-His-Lys-Tyr-Ser (amino acids 16–21) SEQ ID NO: 30 |

The consensus pentapeptide sequences described herein are encompassed by the present invention.

Certain compounds, compositions and methods described in this application relate generally to αC and derivatives thereof which are routinely generated by classical techniques of immunochemistry. This includes αC which has been coupled to another compound by chemical conjugation, or by mixing with an excipient or an adjuvant. The term antigen binding fragment includes any peptide that binds to the C antigen in a cancer cell-specific manner. Typically, these derivatives include such immunoglobulin fragments as Fab, $F(ab')_2$, Fab', scFv (both monomers and polymeric forms) and isolated H and L chains. An antigen binding fragment retains the specificity of H11, although avidity and/or affinity may be altered. Especially preferred is the H11-scFv described herein.

The antigen binding fragments (also termed "derivatives" herein) are typically generated by genetic engineering, although they may alternatively be obtained by other methods and combinations of methods. This classification includes, but is not limited to, engineered peptide fragments and fusion peptides. Preferred compounds include polypeptide fragments of the H11 CDRs, antibody fusion proteins comprising cytokine effector components, antibody fusion proteins comprising adjuvants or drugs, and single-chain V region proteins.

The invention further comprises polynucleotides encoding the H11 antibody V regions and derivatives thereof. These include isolated polynucleotide fragments, recombinant polynucleotides, and therapeutic plasmids and vectors, such as vaccinia vectors, comprising the polynucleotides. These polynucleotides are exemplified by SEQ ID NOS:1, 3, 4, 6, 13, 15, 16, and 18.

Pharmaceutical compositions and treatment modalities of this invention are suitable for eliciting an immune response against neoplasia. Human cancer patients, including, but not limited to, glioblastoma, melanoma, neuroblastoma, adenocarcinoma, glioma, soft tissue sarcoma, and various carcinomas (including small cell lung cancer) are especially appropriate subjects.

As H11 has been shown to recognize specifically a variety of carcinomas, it is particularly useful in diagnosis, imaging and treatment of carcinomas. Suitable carcinomas include any known in the field of oncology, including, but not limited to, astrocytoma, oligodendroglioma, ependymoma, medulloblastoma, primitive neural ectodermal tumor (PNET), pancreatic ductal adenocarcinoma, small and large cell lung adenocarcinomas, squamous cell carcinoma, bronchoalveolarcarcinoma, epithelial adenocarcinoma, and liver metastases thereof, hepatoma, cholangiocarcinoma, breast tumors such as ductal and lobular adenocarcinoma, squamous and adenocarcinomas of the uterine cervix, uterine and ovarian epithelial carcinomas, prostatic adenocarcinomas, transitional squamous cell carcinoma of the bladder, B and T cell lymphomas (nodular and diffuse) plasmacytoma, acute and chronic leukemias, malignant melanoma, soft tissue sarcomas and leiomyosarcomas.

The subjects may have an advanced form of disease, in which case the treatment objective may include mitigation or reversal of disease progression, and amelioration of side effects. The subjects may have had a history of the condition, for which they have already been treated, in which case the objective will typically include a decrease or delay in the risk of recurrence.

Additionally, the antigen binding fragments of this invention can be used as diagnostic and imaging reagents. These applications are described in more detail in the sections that follow.

"H11" is an antibody obtained from the fusion of peripheral blood lymphocytes of a 64 year old male with a low grade glioma and fused to a human myeloma cell line to produce a hybridoma designated NBGM 1/H11. The generation and characterization of H11 is described in Example 1. "αC" represents any antibody, or antigen binding fragment thereof, either monoclonal, polyclonal or derivative thereof that recognizes specifically the C antigen and distinguishes between cancer and noncancer cells. αC includes H11.

"Immunologic activity" of αC refers to the ability to specifically bind C antigen. Such binding may or may not elicit an immune response. A specific immune response may comprise antibody, B cells, T cells, and any combination thereof, and effector functions resulting therefrom. Included are the antibody-mediated functions ADCC and complement-mediated cytolysis (CDC). The T cell response includes T helper cell function, cytotoxic T cell function, inflammation/inducer T cell function, and T cell mediated suppression. A compound able to elicit a specific immune response according to any of these criteria is referred to as "immunogenic." αC "activity" or "function" refers to any of the immunologic activities of αC, or to any other biological activity ascribed to H11 in this disclosure, including the role of H11 in the detection, amelioration or palliation of cancer.

The "V region" of H11 refers to the V region of the $H_{11}$ L chain or the V region of the H11 H chain, either alone or in combination. These V regions are depicted in SEQ ID NOS: 2 and 5; the DNA encoding these regions is depicted in SEQ ID NOS: 1 and 4, respectively.

GM-CSF, IL-2, and other biologically active molecules referred to herein are meant to include fragments and derivatives based on the respective parent molecule that have the same biologic or physiologic function.

The terms "polypeptide", "peptide" and "protein" are used interchangeably herein to refer to polymers of amino acid residues of any length. The polymer may be linear or branched, it may comprise modified amino acids or amino acid analogs, and it may be interrupted by chemical moieties other than amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling or bioactive component. Unless stated or implied otherwise, the term αC or H11 includes any polypeptide monomer or polymer with H11 immunologic specificity, including the intact αC antibody, and smaller and larger functionally equivalent polypeptides.

A "fusion polypeptide" is a polypeptide comprising regions in a different position in the sequence than occurs in nature. The regions may normally exist in separate proteins and are brought together in the fusion polypeptide; they may normally exist in the same protein but are placed in a new arrangement in the fusion polypeptide; or they may be synthetically arranged. For instance, as described below, the invention encompasses recombinant proteins (and the polynucleotides encoding the proteins) that are comprised of a functional portion of αC and a toxin. Methods of making these fusion proteins are known in the art and are described for instance in WO93/07286.

A "functionally equivalent fragment" of a αC polypeptide varies from the native sequence by any combination of additions, deletions, or substitutions while preserving at least one functional property of the fragment relevant to the context in which it is being used. A functionally equivalent fragment of a αC polynucleotide either encodes a polypeptide that is functionally equivalent to H11 when produced by an expression system, or has similar hybridization specificity as a H11 polynucleotide when used in a hybridization assay. A functionally equivalent fragment of a αC polypeptide typically has one or more of the following properties: ability to bind C antigen; ability to bind at least one type of cancer cell in a specific manner; and an ability to elicit an immune response with a similar antigen specificity as that elicited by H11.

A "polynucleotide" is a polymeric form of nucleotides of any length, which contain deoxyribonucleotides, ribonucleotides, and analogs in any combination analogs. Polynucleotides may have any three-dimensional structure, and may perform any function, known or unknown. The term "polynucleotide" includes double-, single-stranded, and triple-helical molecules. Unless otherwise specified or required, any embodiment of the invention described herein that is a polynucleotide encompasses both the double-stranded form and each of two complementary single-stranded forms known or predicted to make up the double stranded form of either the DNA, RNA or hybrid molecules.

The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs, uracyl, other sugars and linking groups such as fluororibose and thioate, and nucleotide branches. The sequence of nucleotides may be interrupted by non-nucleotide components. A polynucleotide may be further modified after polymerization, such as by conjugation with a labeling component. Other types of modifications included in this definition are caps, substitution of one or more of the naturally occurring nucleotides with an analog, and introduction of means for attaching the polynucleotide to proteins, metal ions, labeling components, other polynucleotides, or a solid support.

The term "recombinant" polynucleotide means a polynucleotide of genomic, cDNA, semisynthetic, or synthetic origin which either does not occur in nature or is linked to another polynucleotide in a nonnatural arrangement.

A "vector" refers to a recombinant DNA or RNA plasmid or virus that comprises a heterologous polynucleotide to be delivered into a target cell, either in vitro or in vivo. The heterologous polynucleotide may comprise a sequence of interest for purposes of therapy, and may optionally be in the form of an expression cassette. As used herein, a vector need not be capable of replication in the ultimate target cell or subject. The term includes cloning vectors for the replication of a polynucleotide, and expression vectors for translation of a polynucleotide encoding sequence. Also included are viral vectors, which comprise a polynucleotide encapsidated or enveloped in a viral particle.

A "cell line" or "cell culture" denotes bacterial, plant, insect or higher eukaryotic cells grown or maintained in vitro. The descendants of a cell may not be completely identical (either morphologically, genotypically, or phenotypically) to the parent cell. A Mab may be produced by a hybridoma or other cell. Methods of making hybridomas, both murine and human, are known in the art. Particular methods of producing human hybridomas are described and referenced throughout the specification.

A "host cell" denotes a prokaryotic or eukaryotic cell that has been genetically altered, or is capable of being genetically altered by administration of an exogenous polynucleotide, such as a recombinant plasmid or vector. When referring to genetically altered cells, the term refers both to the originally altered cell, and to the progeny thereof.

"Heterologous" means derived from a genotypically distinct entity from the rest of the entity to which it is being compared. For example, a polynucleotide may be placed by genetic engineering techniques into a plasmid or vector derived from a different source, and is a heterologous polynucleotide. A promoter removed from its native coding sequence and operatively linked to a coding sequence other than the native sequence is a heterologous promoter.

A "signal peptide" or "leader sequence" is a short amino acid sequence that directs a newly synthesized protein through a cellular membrane, usually the endoplasmic reticulum in eukaryotic cells, and either the inner membrane or both inner and outer membranes of bacteria. Signal peptides are typically at the N-terminal portion of a polypeptide and are typically removed enzymatically between biosynthesis and secretion of the polypeptide from the cell. The signal peptide is not present in the secreted protein, only during protein production.

An "isolated" polynucleotide or polypeptide is one that is substantially free of the materials with which it is associated in its native environment. By substantially free is meant at least 50%, preferably at least 70%, more preferably at least 80%, and even more preferably at least 90% free of these materials.

A "stable duplex" of polynucleotides, or a "stable complex" formed between any two or more components in a biochemical reaction, refers to a duplex or complex that is sufficiently long-lasting to persist between the formation of the duplex or complex and subsequent detection, including any optional washing steps or other manipulation that may take place in the interim.

A "biological sample" encompasses a variety of sample types, including blood and other liquid samples of biological origin, solid tissue samples such as a biopsy specimens or tissue cultures, or cells derived therefrom and the progeny thereof. The definition also includes samples that have been manipulated in any way after their procurement, such as by treatment with reagents, solubilization, or enrichment for certain components, such as proteins or polynucleotides. The term encompasses various kinds of clinical samples obtained from any species, and also includes cells in culture, cell supernatants, and cell lysates. Particularly, for the purposes described herein, biological samples comprise tumor tissue or tissue thought to be tumorous and are obtained for instance by surgical resection, biopsy, aspiration or any method known in the art.

An "immunogen" refers to composition for human or animal use, which is administered with the intention of conferring to the recipient a degree of specific immunologic reactivity against a particular antigen. The immunologic reactivity may be carried out by antibodies or cells (particularly B cells, plasma cells, T helper cells, and cytotoxic T lymphocytes, and their precursors) that are immunologically reactive against the target, or any combination thereof. For purposes of this invention, the target is primarily tumor-associated C antigen or a tumor-specific portion thereof. The immunologic reactivity may be desired for experimental purposes for treatment of a particular condition, for the elimination of a particular substance, or for prophylaxis. An active immunogen is intended to elicit an immune response that persists in the absence of the vaccine components.

"Adjuvant" as used herein has several meanings, all of which will be clear depending on the context in which the term is used. In the context of a pharmaceutical preparation, an adjuvant is a chemical or biological agent given in combination with or recombinantly fused to an antigen to enhance immunogenicity of the antigen. In the context of cancer diagnosis or management, adjuvant refers to a class of cancer patients with no clinically detectable tumor mass, but who are suspected of being at risk of recurrence.

When referring to a type of cancer that normally manifests as a solid tumor, a "clinically detectable" tumor is one that is detectable on the basis of tumor mass; i.e., by such procedures as CAT scan, X-Ray, or palpation. Biochemical, histological or immunologic findings alone may be insufficient to meet this definition.

As used herein, "treatment" refers to clinical intervention in an attempt to alter the natural course of the individual or cell being treated, and may be performed either for prophylaxis or during the course of clinical pathology. Desirable effects of the treatment include preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis.

The "pathology" associated with a disease condition is any condition that compromises the well-being, normal physiology, or quality of life of the affected individual. This may involve, but is not limited to, destructive invasion of affected tissues into previously unaffected areas, growth at the expense of normal tissue function, irregular or suppressed biological activity, aggravation or suppression of an inflammatory or immunologic response, increased susceptibility to other pathogenic organisms or agents, and undesirable clinical symptoms such as pain, fever, nausea, fatigue, mood alterations, and such other features as may be determined by an attending physician.

An "effective amount" is an amount sufficient to effect a beneficial or desired clinical result. An effective amount can be administered in one or more doses. In terms of treatment, an effective amount is amount that is sufficient to palliate, ameliorate, stabilize, reverse or slow the progression of the disease, or otherwise reduce the pathological consequences of the disease. In terms of an adjuvant, an effective amount is one sufficient to enhance the immune response to the immunogen. The effective amount is generally determined by the physician on a case-by-case basis and is within the skill of one in the art. Several factors are typically taken into account when determining an appropriate dosage. These factors include age, sex and weight of the patient the condition being treated, the severity of the condition and the form of the antibody being administered. For instance, the concentration of scFv need not be as high as that of native antibodies in order to be therapeutically effective.

An "individual", "patient" or "subject" is a vertebrate, preferably a mammal, more preferably a human. Mammals include, but are not limited to, humans, farm animals, sport animals, and pets.

The practice of the present invention employs, unless otherwise indicated, conventional techniques of molecular biology (including recombinant techniques), microbiology, cell biology, biochemistry and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait, ed., 1984); "Animal Cell Culture" (R. I. Freshney, ed., 1987); "Methods in Enzymology" (Academic Press, Inc.); "Handbook of Experimental Immunology" (D. M. Wei & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al., eds., 1994); "Current Protocols in Immunology" (J. E. Coligan et. al., eds., 1991). These techniques are applicable to the production of the polynucleotides and polypeptides of the invention, and, as such, may be considered in making and practicing the invention. Particularly useful techniques for particular embodiments will be discussed in the sections that follow.

The invention also encompasses αC conjugated to a chemically functional moiety. Typically, the moiety is a label capable of producing a detectable signal. These conjugated αC are useful, for example, in detection systems such as quantitation of tumor burden, and imaging of metastatic foci and tumor imaging. Such labels are known in the art and include, but are not limited to, radioisotopes, enzymes, fluorescent compounds, chemiluminescent compounds, bioluminescent compounds substrate cofactors and inhibitors. See, for examples of patents teaching the use of such labels, U.S. Pat. Nos. 3,817,837; 3,850,752; 3,939,350; 3,996,345; 4,277,437; 4,275,149; and 4,366,241. The moieties may be covalently linked to αC, recombinantly linked, or conjugated to the αC through a secondary reagent, such as a second antibody, protein A, or a biotin-avidin complex.

Other functional moieties include signal peptides, agents that enhance immunologic reactivity, agents that facilitate coupling to a solid support, vaccine carriers, bioresponse modifiers, paramagnetic labels and drugs. Signal peptides are described above and include prokaryotic and eukaryotic forms. Agents that enhance immunologic reactivity include, but are not limited to, bacterial superantigens. Agents that facilitate coupling to a solid support include, but are not limited to, biotin or avidin. Immunogen carriers include, but are not limited to, any physiologically acceptable buffers. Bioresponse modifiers include cytokines, particularly tumor necrosis factor (TNF), interleukin-2, interleukin-4, granulocyte macrophage colony stimulating factor and γ interferons.

Suitable drug moieties include antineoplastic agents. These include, but are not limited to, radioisotopes, vinca alkaloids such as the vinblastine, vincristine and vindesine sulfates, adriamycin, bleomycin sulfate, carboplatin, cisplatin, cyclophosphamide, cytarabine, dacarbazine, dactinomycin, duanorubicin hydrochloride, doxorubicin hydrochloride, etoposide, fluorouracil, lomustine, mechlororethamine hydrochloride, melphalan, mercaptopurine, methotrexate, mitomycin, mitotane, pentostatin, pipobroman, procarbaze hydrochloride, streptozotocin, taxol, thioguanine, and uracil mustard.

Immunotoxins, including single chain molecules, can be produced by recombinant means. Production of various immunotoxins is well-known in the art, and methods can be found, for example, in "Monoclonal Antibody-toxin Conjugates: Aiming the Magic Bullet," Thorpe et al. (1982) *Monoclonal Antibodies in Clinical Medicine*, Academic Press, pp. 168–190; Vitatta (1987) Science 238:1098–1104; and Winter and Milstein (1991) *Nature* 349:293–299. Suitable toxins include, but are not limited to, ricin, radionuclides, pokeweed antiviral protein, *Pseudomonas* exotoxin A, diphtheria toxin, ricin A chain, fungal toxins such as restrictocin and phospholipase enzymes. See, generally, "Chimeric Toxins," Olsnes and Pihl, *Pharmac. Ther.* 15:355–381 (1981); and "Monoclonal Antibodies for Cancer Detection and Therapy," eds. Baldwin and Byers, pp. 159–179, 224–266, Academic Press (1985).

The chemically functional moieties can be made recombinantly for instance by creating a fusion gene encoding the antigen binding fragment and functional regions from other genes (e.g. enzymes). In the case of gene fusions, the two components are present within the same polypeptide gene. Alternatively, the αC antigen binding fragments can be chemically bonded to the moiety by any of a variety of well known chemical procedures. For example, when the moiety is a protein, the linkage may be by way of heterobifunctional cross linkers, e.g., SPDP, carbodiimide glutaraldehyde, or the like. The moieties may be covalently linked, or conjugated, through a secondary reagent, such as a second antibody, protein A, or a biotin-avidin complex. Paramagnetic moieties and the conjugation thereof to antibodies are well-known in the art. See, e.g., Miltenyi et al. (1990) *Cytometry* 11:231–238.

The αC antibody of this invention can be prepared in several ways. It is most conveniently obtained from cells engineered to express an antigen binding fragment containing SEQ ID NOS:1 and 5 or other polynucleotides encoding αC binding fragments. For example, the cells can be cultured in a suitable medium, and spent medium can be used as an antibody source. Optionally, matrix-coated channels or beads and cell co-cultures may be included to enhance growth of antibody-producing cells. For the production of large amounts of antibody, it is generally more convenient to obtain an ascites fluid. The method of raising ascites generally comprises injecting hybridoma cells into an immunologically naive histocompatible or immunotolerant mammal, especially a mouse. The mammal may be primed for ascites production by prior administration of a suitable composition; e.g., Pristane.

Alternatively, αC can be chemically synthesized using sequence data and other information provided in this disclosure, in conjunction with standard methods of protein synthesis. A suitable method is the solid-phase Merrifield technique. Automated peptide synthesizers are commercially available, such as those manufactured by Applied Biosystems, Inc. (Foster City, Calif.).

αC may also be obtained by employing routine recombinant methods such as described in Sambrook et al. (1989). For instance, using the amino acid and polynucleotide (SEQ ID NOS:1–6, and 13–18) sequences and information provided herein, a polynucleotide encoding either the αC H or L chain can be cloned into a suitable expression vector (which contains control sequences for transcription, such as a promoter). The expression vector is in turn introduced into a host cell. The host cell is grown under suitable conditions such that the polynucleotide is transcribed and translated into a protein. H and L chains of αC may be produced separately, and then combined by disulfide bond rearrangement. Alternatively, vectors with separate polynucleotides encoding each chain of αC, or a vector with a single polynucleotide encoding both chains as separate transcripts, may be transfected into a single host cell which may then produce and assemble the entire molecule. Preferably, the host cell is derived from a higher eukaryote that can provide the normal carbohydrate complement of the molecule. The αC thus produced can be purified using standard techniques in the art. Polynucleotides encoding αC for use in the production of αC can in turn be obtained from a hybridoma producing a αC antibody, or produced synthetically or recombinantly from the DNA sequences provided herein.

Another method of obtaining αC is to immunize suitable host animals with C antigen and to follow standard procedures for polyclonal or Mab production. Mabs thus produced can be "humanized" by methods known in the art. Examples of humanized antibodies are provided, for instance, in U.S. Pat. Nos. 5,530,101 and 5,585,089.

"Humanized" antibodies are antibodies in which at least part of the sequence has been altered from its initial form to render it more like human immunoglobulins. In one version, the H chain and L chain C regions are replaced with human sequence. This is a fusion polypeptide comprising a H11 V region and a heterologous immunoglobulin C region. In another version, the CDR regions comprise H11 amino acid sequences, while the V framework regions have also been converted human sequences. See, for example, EP 0329400. In a third version, V regions are humanized by designing consensus sequences of human and mouse V regions, and converting residues outside the CDRs that are different between the consensus sequences. The invention encompasses humanized Mabs.

In making humanized antibodies, the choice of framework residues can be critical in retaining high binding affinity. In principle, a framework sequence from any HuAb can serve as the template for CDR grafting; however, it has been demonstrated that straight CDR replacement into such a framework can lead to significant loss of binding affinity to the antigen. Glaser et al. (1992) *J. Immunol.* 149:2606; Tempest et al. (1992) *Biotechnology* 9:266; and Shalaby et al. (1992) *J. Exp. Med* 17:217. The more homologous a HuAb is to the original muAb, the less likely that the human framework will introduce distortions into the murine CDRs that could reduce affinity. Based on a sequence homology search against an antibody sequence database, the HuAb IC4 provides good framework homology to muM4TS.22, although other highly homologous HuAbs would be suitable as well, especially kappa L chains from human subgroup I or H chains from human subgroup III. Kabat et al. (1987). Various computer programs such as ENCAD (Levitt et al. (1983) *J. Mol. Biol.* 168:595) are available to predict the ideal sequence for the V region. The invention thus encompasses HuAbs with different V regions. It is within the skill of one in the art to determine suitable V region sequences and to optimize these sequences. Methods for obtaining antibodies with reduced immunogenicity are also described in U.S. Pat. No. 5,270,202 and EP 699,755.

Methods of antibody production and isolation are well known in the art. See, for example, Harlow and Lane (1988) *Antibodies: A Laboratory Manual*, Cold Spring Harbor Laboratory, New York. The H11 antibody is a human immunoglobulin of the IgM subclass, and may be isolated by any technique suitable for immunoglobulins of this isotype. Purification methods may include salt precipitation (for example, with ammonium sulfate), ion exchange chromatography (for example, on a cationic or anionic exchange column run at neutral pH and eluted with step gradients of increasing ionic strength), gel filtration chromatography (including gel filtration HPLC), and chromatography on affinity resins such as protein A, protein G, hydroxyapatite, and anti-immunoglobulin. H11 may also be purified on affinity columns comprising the C antigen; for example, in the form of a purified Ab1 or Ab3. Preferably, H11 is purified using Protein-A-CL-Sepharose™ 4B chromatography followed by chromatography on a DEAE-Sepharose™ 4B ion exchange column.

The invention also encompasses hybrid antibodies, in which one pair of H and L chains is obtained from a first antibody, while the other pair of H and L chains is obtained from a different second antibody. For purposes of this invention, one pair of L and H chains is from αC. In one example, each L-H chain pair binds different epitopes of the C antigen. Such hybrids may also be formed using humanized H or L chains.

Another αC contemplated by this invention is an antibody in which the H or L chain has been modified to provide additional properties. For instance, a change in amino acid sequence can result in reduced immunogenicity of the resultant polypeptide. The changes range from changing of one or more amino acids to the complete redesign of a region such as a C region domain. Typical changes include, but are not limited to, those related to complement fixation, interaction with membrane receptors, and other effector functions. A recombinant antibody may also be designed to aid the specific delivery of a substance (such as a cytokine) to a tumor cell. Also encompassed by the invention are peptides in which various immunoglobulin domains have been placed in an order other than that which occurs in nature.

If αC is to be administered to an individual, it is preferably at least 80% pure, more preferably it is at least 90% pure, even more preferably it is at least 95% pure and free of pyrogens and other contaminants. In this context, the percent purity is calculated as a weight percent of the total protein content of the preparation, and does not include constituents which are deliberately added to the composition after the αC is purified.

The αC antibodies may be used for a number of purposes. These include eliciting an antibody response to produce αC which can then be used to elicit a T cell response to αC or the C antigen and treating various types of cancer. These uses are elaborated more fully in a later section.

The invention encompasses polypeptide fragments of αC containing at least a portion of a V region of αC. Preferred fragments are those with the immunologic activity of H11. Also preferred are fragments which comprise amino acid sequences substantially different from other immunoglobulins, and fragments comprising a CDR. In one embodiment, the invention includes a polypeptide fragment of the αC H chain V region, comprising at least 25 consecutive amino acids, more preferably 30 consecutive amino acids of SEQ ID NO:2, or 5 consecutive amino acids of the CDR1 thereof, or at least 7 consecutive amino acids, preferably at least 9 consecutive amino acids of the CDR2 or CDR3 thereof. The invention also includes a polypeptide fragment of the αC L chain V region, comprising at least 25 consecutive amino acids, more preferably 30 consecutive amino acids of SEQ ID NO:5, or 7 consecutive amino acids of the CDR2 thereof, or at least 8 consecutive amino acids, preferably 10 consecutive amino acids of the CDR1 or CDR3 thereof.

The size of the αC polypeptides can be only the minimum size required to provide a desired function. The polypeptides can optionally comprise additional sequence, either native to αC, or from a heterologous source, as desired. αC peptides can contain only 5 consecutive amino acids from a H11 V region sequence that are not the same as the homologous region of A6. Polypeptides comprising 7 amino acids, more preferably about 10 amino acids, more preferably about 15 amino acids, more preferably about 25 amino acids, more preferably about 50 amino acids, more preferably about 75 amino acids from the αC L or H chain V region are also included. Even more preferred are polypeptides comprising the entire αC L or H chain V region. Preferably the polypeptides are derived from H11. Preferably, the polypeptides are the scFvs depicted in SEC ID NOS:14 and 17.

The invention includes modified αC polypeptides which are functionally equivalent to H11, or have altered but measurable H11 immunologic activity. Modified polypeptides with improved H11 immunologic activity are preferred. Examples of modified polypeptides include those with conservative substitutions of amino acid residues, and one or more deletions or additions of amino acids which do not significantly deleteriously alter the immunologic activity.

One example of this is H11 polypeptides comprising one or more amino acid substitution in comparison with the prototype H11 sequence. Substitutions can range from changing or modifying one or more amino acid residues to complete redesign of a region, such as the V region. Amino acid substitutions, if present, are preferably conservative substitutions that do not deleteriously affect folding or functional properties of the peptide. Groups of functionally related amino acids within which conservative substitutions can be made are glycine/alanine; valine/isoleucine/leucine; asparagine/glutamine; aspartic acid/glutamic acid, serine/threonine/methionine; lysine/arginine; and phenylalanine/tryosine/tryptophan. Polypeptides of this invention can be in glycosylated or unglycosylated form, can be modified post-translationally (e.g., acetylation, and phosphorylation) or can be modified synthetically (e.g., the attachment of a labeling group).

H11 polypeptide derivatives comprising both a H11 L chain and a H11 H chain can be formed as separate L and H chains and then assembled, or assembled in situ by an expression system for both chains. Such expression systems can be created by transfecting a suitable cell with a plasmid comprising separate transcribable regions for the L and H chain, or by co-transfecting the same cell with plasmids for each chain. In a third method, a suitable plasmid with a H chain encoding region is transfected into a H chain loss mutant.

H chain loss mutants can be obtained by treating approximately $2 \times 10^7$ H11 producing cells with fluorescein-labeled rabbit anti-mouse IgG (H chain specific, DAKO Corporation, Carpinteria, Calif.) according to the supplier's instruction. The stained and unstained cell populations are analyzed in a fluorescence-activated cell sorter. The unstained cells are collected in a sterilized tube and placed in 96-well plates with 1 cell/well by limiting dilution. The culture supernatants are then assayed by ELISA using goat anti-mouse IgG (H chain specific) and goat anti-mouse kappa. The clones with kappa-positive and IgG-negative phenotype are subcloned at least 3 times to obtain stable $H11^{(-H)}$ mutants. mRNA from putative H chain loss mutant $H11^{(-H)}$ clones can be isolated and the sequence of the L chain V region cDNA determined. Reverse PCR of the mRNA for the H11 $V_H$ is performed with 2 sets of 5'- and 3'- primers, used for cloning of $H_{11}^{(-H)}$ cDNA (Example 7). A H chain loss mutant yields no detectable DNA band. Transfection of the cells proceeds with a suitable H chain plasmid.

Another αC derivative encompassed by this invention is an antibody in which the αC H or L chain has been modified to provide additional properties. For instance, a change in amino acid sequence can result in greater immunogenicity of the resultant polypeptide. The changes range from changing of one or more amino acids to the complete redesign of a region such as a C region domain. Changes contemplated affect complement fixation, interaction with membrane receptors, and other effector functions. A recombinant H11 antibody can also be designed to aid the specific delivery of a substance (such as a lymphokine) to an effector cell. Also encompassed by the invention are proteins in which various immunoglobulin domains have been placed in an order other than that which occurs in nature.

The invention also encompasses single chain V region fragments ("scFv") of H11. Single chain V region fragments are made by linking L and/or H chain V regions by using a short linking peptide. Bird et al. (1988) *Science* 242:423–426. Any peptide having sufficient flexibility and length can be used as a linker in a scFv. Usually the linker is selected to have little to no immunogenicity. An example of a linking peptide is $(GGGGS)_3$, which bridges approximately 3.5 nm between the carboxy terminus of one V region and the amino terminus of another V region. Other linker sequences can also be used, and can provide additional functions, such as a means for attaching a drug or a solid support.

All or any portion of the H or L chain can be used in any combination. Typically, the entire V regions are included in the scFv. For instance, the L chain V region can be linked to the H chain V region. Alternatively, a portion of the L chain V region can be linked to the H chain V region, or a portion thereof. Also contemplated are scFvs in which the H chain V region is from H11, and the L chain V region is from another immunoglobulin. It is also possible to construct a biphasic, scFv in which one component is a H11 polypeptide and another component is a different polypeptide, such as a T cell epitope.

The scFvs can be assembled in any order, for example, $V_H$-(linker)-$V_L$ or $V_L$-(linker)-$V_H$. For example, SEQ ID NOS:13 and 16 show H11-scFv2 constructs having the form $V_L$-(linker)-$V_H$. However, the construct shown in SEQ ID NO:13 forms monomers, while the construct shown in SEQ ID NO:16 forms dimers. There may be a difference in the level of expression of these two configurations in particular expression systems, in which case one of these forms may be preferred. Tandem scFvs can also be made, such as (X)-(linker)-(X)-(linker)-(X), in which X are αC polypeptides, or combinations of αC polypeptides with other polypeptides. In another embodiment, single chain antibody polypeptides have no linker polypeptide, or just a short, inflexible linker. Exemplary configurations include $V_L$-$V_H$ and $V_H$-$V_L$. The linkage is too short to permit interaction between $V_L$ and $V_H$ within the chain, and the chains form homodimers with a $V_L/V_H$ antigen binding site at each end. Such molecules are referred to in the art as "diabodies".

ScFvs can be produced either recombinantly or synthetically. For synthetic production of scFv, an automated synthesizer can be used. For recombinant production of scFv, a suitable plasmid containing a polynucleotide that encodes the scFv can be introduced into a suitable host cell, either eukaryotic, such as yeast, plant, insect or mammalian cells, or prokaryotic, such as *Escherichia coli*, and the protein expressed by the polynucleotide can be isolated using standard protein purification techniques.

A particularly useful system for the production of scFvs is plasmid pET-22b(+) (Novagen, Madison, Wis.) in *E. coli*. pET-22b(+) contains a nickel ion binding domain consisting of 6 sequential histidine residues, which allows the expressed protein to be purified on a suitable affinity resin. Another example of a suitable vector is pcDNA3 (Invitrogen, San Diego, Calif.), described above.

Expression conditions should ensure that the scFv assumes functional and, preferably, optimal tertiary structure. Depending on the plasmid used (especially the activity of the promoter) and the host cell, it may be necessary to modulate the rate of production. For instance, use of a weaker promoter, or expression at lower temperatures, may be necessary to optimize production of properly folded scFv in prokaryotic systems; or, it may be preferably to express scFv in eukaryotic cells.

Preferred scFv comprise at least 10 consecutive amino acids of SEQ. ID NO:2 and at least 10 consecutive amino acids of SEQ. ID NO:5, especially wherein the amino acids of SEQ. ID NO:2 and the amino acids of SEQ. ID NO:5 are joined by a linker polypeptide of 5 to 20 amino acids, or comprising the L chain V region and the H chain V region of H11.

The invention also encompasses polymeric forms of αC polypeptides, containing a plurality of αC polypeptides. One embodiment is a linear polymer of αC polypeptides, optionally conjugated to carrier. These linear polymers can comprise multiple copies of a single αC polypeptide, or combinations of different αC polypeptides, and can have tandem αC polypeptides, or αC polypeptides separated by other amino acid sequences. Another embodiment is αC multiple antigen peptides (MAPs). MAPs have a small immunologically inert core having radially branching lysine dendrites, onto which a number of αC polypeptides are covalently attached. See for instance, Posnett et al. (1988) *J. Biol. Chem.* 263:1719–1725; and Tam (1989) *Meth. Enz.* 168: 7–15. The result is a large macromolecule having a high molar ratio of αC polypeptides to core. MAPs are efficient immunogens and useful antigens for immunoassays. The core for creating an αC MAP can be made by standard peptide synthesis techniques, or obtained commercially, e.g., from Quality Controlled Biochemicals, Inc., Hopkinton, Mass. A typical core matrix is made up of three levels of lysine and eight amino acids.

When using αC polypeptides as immunogens, preferably the polypeptides are delivered in conjunction with a carrier. Any carrier can be used which is not harmful to the host. Suitable carriers are typically large, slowly metabolized macromolecules such as proteins; polysaccharides (such as latex functionalized Sepharose, agarose, cellulose, cellulose beads and the like); polymeric amino acids (such as polyglutamic acid, polylysine, and the like); amino acid copolymers; and inactive virus particles or attenuated bacteria, such as *Salmonella*. Especially useful carrier proteins are serum albumins, keyhole limpet hemacyanin (KLH), certain Ig molecules, thyroglobulin, ovalbumin, and tetanus toxoid. KLH is especially preferred.

αC polypeptides of the invention can be identified in a number of ways. For example, the V regions of the L and H chains can be screened by preparing a series of short polypeptides that together span the entire V region amino acid sequence. Using a series of polypeptides of 20 or 50 amino acids in length, each αC V region can be surveyed for useful functional properties. It is also possible to carry out a computer analysis of a protein sequence to identify potentially interesting polypeptides, such as those that bear the shape of D2, or those involved in idiotype-anti-idiotype contact.

The invention further encompasses various adaptations of αC described in this section combined in various fashions to yield other αC polypeptides with desirable properties. For instance. αC polypeptides with modified amino acid residues can be comprised in a MAP. In another example, a αC scFv is fused to a cytokine, such as IL-2. All such combinations are contemplated in this invention.

The polypeptides of this invention can be made by any suitable procedure, including proteolysis of the αC antibody, by recombinant methods or by chemical synthesis. These methods are known in the art and need not be described in detail herein. Examples of proteolytic enzymes include, but are not limited to, trypsin, chymotrypsin, pepsin, papain, V8 protease, subtilisin, plasmin, and thrombin. Intact αC can be incubated with one or more proteinases simultaneously or sequentially. Alternatively, or in addition, intact antibody can be treated with disulfide reducing agents. Peptides can then be separated from each other by techniques known in the art including, but not limited to, gel filtration chromatography, gel electrophoresis, and reverse-phase HPLC.

αC polypeptides can also be made by expression from a polynucleotide encoding the peptide according to the information provided elsewhere in this application, in a suitable expression system. Typically, polynucleotides encoding a αC polypeptide are ligated into an expression vector under control of a suitable promoter and used to genetically alter the intended host cell. Both eukaryotic and prokaryotic host systems can be used. The polypeptide is then isolated from lysed cells or from the culture medium and purified to the extent needed for its intended use. Examples of prokaryotic host cells appropriate for use with this invention include *E. coli*. Examples of eukaryotic host cells include avian, insect, plant, and animal cells including, but not limited to, COS7, HeLa, and CHO cells.

In certain applications, such as when a H11 polypeptide is expressed in a suitable storage medium such as a plant seed, the H11 polypeptide can be used without purification. Fiedler et al. (1995) *Biotechnology* 13:1090–1093. For most applications, it is generally preferable that the polypeptide is at least partially purified from other cellular constituents. Preferably, the polypeptide is at least about 50% pure as a weight percent of total protein. More preferably, the protein is at least about 50–75% pure. For clinical use, the polypeptide is preferably at least about 80% pure.

The invention also encompasses methods of detecting C antigen in a biological sample. The methods include obtaining a biological sample, contacting the sample with αC under conditions that allow antibody antigen binding and detecting binding, if any, of the antibody to the antigen.

The invention also encompasses methods of detecting anti-H11 or anti-αC in a biological sample. Anti-αC is detectable whenever it cross-reacts with H11. Anti-αC with this activity can spontaneously arise during the course of a tumor-associated disease. Anti-αC with this activity is especially likely in individuals who have received a course of therapy with αC. These methods are applicable in a clinical setting, for example, for monitoring antibody levels in an individual, as well as an industrial setting, as in commercial production of anti-H11 or anti-αC.

The assay methods entail contacting any anti-H11 or anti-αC target antibody in the sample with a H11 antibody or polypeptide under conditions suitable to allow the formation of a stable complex between the target and H 1, and detecting any stable complex formed. The sample is suitably prepared before conducting the assay, optionally by enriching for antibody concentration. When using intact murine αC, it is generally preferable to deplete the sample of any anti-mouse immunoglobulin activity that may be present. Anti-mouse immunoglobulin antibody can be removed from a sample, for example, by precipitation with normal mouse IgG or adsorption with a mouse Ig adsorbent. Binding of anti-mouse immunoglobulin antibody, particularly that specific for the Fc region, can be minimized by judicious choice of the reagents of the assay. F(ab')$_2$ or Fab fragments of murine αC and other reagents such as humanized αC or H11, with fewer mouse determinants are appropriate.

After the sample is suitably prepared, it is mixed with a excess αC under conditions that permit formation of a complex between αC and any target antibody that may be present. The amount of complex is then determined, and compared with complexes formed with standard samples containing known amounts of target antibody in the range expected. Complex formation can be observed by any method known in the art such as immunoprecipitation or nephelometry, but it is generally more sensitive to employ a reagent labeled with such labels as radioisotopes such as $^{125}$I, enzymes such as peroxidase and β-galactosidase, or fluorochromes such as fluorescein.

The invention provides various polynucleotides encoding the antibody H11 or fragments of H11, based on the polynucleotide sequences provided herein (SEQ ID NOS:1 and 4). Various embodiments are described in this section, comprising a number of different combinations of the H11 H or L chain V region sequences. In general, a H11 polynucleotide of this invention encodes at least one feature that is unique to the H11 molecule (in comparison with other immunoglobulins and, in particular, the A6 antibody). Preferably, this feature is related in some way to an immunologic reactivity of H11.

The invention encompasses polynucleotides encoding a portion of the H11 L chain V region, comprising at least about 70 consecutive nucleotides, preferably at least about 80 consecutive nucleotides, more preferably at least about 100 consecutive nucleotides, even more preferably at least about 150 nucleotides of SEQ ID NO:4. The invention also encompasses a polynucleotide encoding a portion of the H11 L chain V region, comprising at least about 25 consecutive nucleotides, preferably at least about 30 consecutive nucleotides, and even more preferably at least about 35 consecutive nucleotides of the CDR1 encoding sequence thereof. The invention also encompasses a polynucleotide encoding a portion of the H11 L chain V region, comprising at least about 20 consecutive nucleotides, preferably at least about 25 consecutive nucleotides, and even more preferably at least about 35 consecutive nucleotides of the CDR2 or CDR3 encoding sequence thereof.

The invention also encompasses polynucleotides encoding a portion of the H11 H chain V region, comprising at least about 70 consecutive nucleotides, preferably at least about 80 consecutive nucleotides, more preferably at least about 100 consecutive nucleotides, even more preferably at least about 150 nucleotides of SEQ ID NO:1. The invention also encompasses a polynucleotide encoding a portion of the H11 L chain V region, comprising 15 consecutive nucleotides of the CDR1 encoding sequence thereof. The invention also encompasses a polynucleotide encoding a portion of the H11 L chain V region, comprising at least about 20 consecutive nucleotides, preferably at least about 25 consecutive nucleotides, and even more preferably at least about 35 consecutive nucleotides of the CDR2 or CDR3 coding sequence thereof.

The invention includes isolated H11 polynucleotides encoding a polypeptide having immunologic activity of H11, wherein the polypeptide encodes at least 5 amino acids of a V L chain of H11 as depicted in SEQ. ID NO:5. The invention also includes isolated H11 polynucleotides encoding a polypeptide having immunologic activity of H11, wherein the polynucleotide encodes at least 5 amino acids of a V H chain of H11 as depicted in SEQ. ID NO:2. The polynucleotide sequence can be similar to those depicted in SEQ. ID NO:1 or SEQ ID NO:4 with changes designed to optimize codon usage, stability, facilitate cloning, or any other purpose. It is within the skill of one in the art, given the amino acid sequence in SEQ ID NO:2 or SEQ ID NO:5, to design such polynucleotides. Preferred polynucleotides encode at least five amino acids of a H11 CDR.

The invention also encompasses polynucleotides encoding for functionally equivalent variants and derivatives of H11 and functionally equivalent fragments thereof which may enhance, decrease or not significantly affect properties of the polypeptides encoded thereby. These functionally equivalent variants, derivatives, and fragments display the ability to specifically recognize C antigen. For instance, changes in a DNA sequence that do not change the encoded amino acid sequence, as well as those that result in conservative substitutions of amino acid residues, one or a few amino acid deletions or additions, and substitution of amino acid residues by amino acid analogs are those which will not significantly affect properties of the encoded polypeptide. Conservative amino acid substitutions are glycine/alanine; valine/isoleucine/leucine; asparagine/glutamine; aspartic acid/glutamic acid; serine/threonine/methionine; lysine/arginine; and phenylalanine/tyrosine/tryptophan.

The polynucleotides of the invention may comprise additional sequences, such as additional encoding sequences within the same transcription unit, controlling elements such as promoters, ribosome binding sites, and polyadenylation sites, additional transcription units under control of the same or a different promoter, sequences that permit cloning, expression, and transformation of a host cell, and any such construct as may be desirable to provide embodiments of this invention.

The invention encompasses a polynucleotide of at least about 15 consecutive nucleotides, preferably at least about 20 nucleotides, more preferably at least about 25 consecutive nucleotides, more preferably at least about 35 consecutive nucleotides, more preferably at least about 50 consecutive nucleotides, even more preferably at least about 75 nucleotides, still more preferably at least about 100 nucleotides, still more preferably at least about 200 nucleotides, and even more preferably at least about 300 nucleotides that forms a stable hybrid with a polynucleotide encoding the L chain or H chain V region of H11, but not with other immunoglobulin encoding regions known at the time of filing of this application. Any set of conditions may be used for this test, as long as at least one set of conditions exist wherein the test polynucleotide demonstrates the required specificity. Preferably, the H11 encoding sequences to which the test polynucleotide binds are those shown in SEQ. ID NOS:1 and 4. Since the known immunoglobulin sequences fall into a hierarchy of similarity with that of H11, the test may be performed by comparing the hybridization of the test polynucleotide with the H11 sequence with the hybridization with the most closely related sequences. Preferred is a panel of about 10 of the most closely related sequences to SEQ. ID NO:1, 3, 4 or 5.

Hybridization reactions can be performed under conditions of different "stringency". Conditions that increase stringency of a hybridization reaction are well known. See, for example, Sambrook and Maniatis. Examples of relevant conditions include (in order of increasing stringency): incubation temperatures of 25° C., 37° C., 50° C. and 68° C.; buffer concentrations of 10× SSC, 6× SSC, 1× SSC, 0.1× SSC (where SSC is 0.15 M NaCl and 15 mM citrate buffer) and their equivalent using other buffer systems; formamide concentrations of 0%, 25%, 50%, and 75%; incubation times from 5 minutes to 24 hours; 1, 2, or more washing steps; wash incubation times of 1, 2, or 15 minutes; and wash solutions of 6× SSC, 1× SSC, 0.1× SSC, or deionized water.

Useful H11 polynucleotides encoding fragments of H11 may be identified by generating polynucleotide fragments (based on SEQ ID NO:1 or SEQ ID NO:4, for example) and testing the polypeptides encoded thereby for a function of interest. Alternatively, the polypeptide fragment encoded by a particular polynucleotide can be prepared and tested for a function of interest. Alternatively, given a αC polypeptide with desirable properties, polynucleotides can be designed that encode the polypeptide.

Included in all these embodiments are polynucleotides with encoding regions for H11 polymers, fusion proteins, humanized immunoglobulins, single-chain V regions, and other particular polypeptides of interest. These polypeptides are described above.

The invention also provides polynucleotides covalently linked with a detectable label. Such polynucleotides are useful, for example, as probes for detection of related nucleotide sequences.

The polynucleotides of this invention can be obtained using chemical synthesis, recombinant cloning methods, PCR, or any combination thereof. Methods of chemical polynucleotide synthesis are well known in the art and need not be described in detail herein. One of skill in the art can use the sequence data provided herein to obtain a desired polynucleotide by employing a DNA synthesizer or ordering from a commercial service.

Alternatively, αC polynucleotide sequences can be obtained from a αC antibody producing cell line. αC cloning vector, or αC expression vector. RNA or DNA encoding the desired sequence can be isolated, amplified, and processed by standard recombinant techniques. Such techniques include digestion with restriction nucleases, and amplification by polymerase chain reaction (PCR), or a suitable combination thereof. PCR technology is described in U.S. Pat. Nos. 4,683,195, 4,800,159, 4,754,065 and 4,683,202, as well as PCR: The Polymerase Chain Reaction, Mullis et al. eds., Birkauswer Press, Boston (1994).

Polynucleotides comprising a desired sequence can be inserted into a suitable vector, and the vector in turn can be introduced into a suitable host cell for replication and amplification. Polynucleotides can be introduced into host cells by any means known in the art. Cells are transformed by introducing an exogenous polynucleotide by direct uptake, endocytosis, transfection, f-mating or electroporation. Once introduced, the exogenous polynucleotide can be maintained within the cell as a non-integrated vector (such as a plasmid) or integrated into the host cell genome. Amplified DNA can be isolated from the host cell by standard methods. See, e.g., Sambrook et al. (1989). RNA can also be obtained from transformed host cell, or it can be obtained directly from the DNA by using a DNA-dependent RNA polymerase.

The present invention further encompasses a variety of vectors comprising a H11 polynucleotide. These vectors can be used for expression of recombinant polypeptides are also a source of H11 polynucleotides. Cloning vectors can be used to obtain replicate copies of the H11 polynucleotides they contain, or as a means of storing the polynucleotides in a depository for future recovery. Expression vectors (and host cells containing these expression vectors) can be used to obtain polypeptides produced from the polynucleotides they contain. They can also be used where it is desirable to express H11 in an individual and thus have intact cells capable of synthesizing the polypeptide, such as in gene therapy. Suitable cloning and expression vectors include any known in the art, e.g., those for use in bacterial, mammalian, yeast and insect expression systems. Specific vectors and suitable host cells are known in the art and are not described in detail herein. See e.g. Gacesa and Ramji, Vectors, John Wiley & Sons (1994).

Cloning and expression vectors typically contain a selectable marker (for example, a gene encoding a protein necessary for the survival or growth of a host cell transformed with the vector), although such a marker gene can be carried on another polynucleotide sequence co-introduced into the host cell. Only those host cells into which a selectable gene has been introduced will grow under selective conditions. Typical selection genes either: (a) confer resistance to antibiotics or other toxins, e.g., ampicillin, neomycin, methotrexate; (b) complement auxotrophic deficiencies; or (c) supply critical nutrients not available from complex media. The choice of the proper marker gene will depend on the host cell, and appropriate genes for different hosts are known in the art. Vectors also typically contain a replication system recognized by the host.

Suitable cloning vectors can be constructed according to standard techniques, or selected from a large number of cloning vectors available in the art. While the cloning vector selected may vary according to the host cell intended to be used, useful cloning vectors will generally have the ability to self-replicate, may possess a single target for a particular restriction endonuclease, or may carry marker genes. Suitable examples include plasmids and bacterial viruses, e.g., pUC18, mp18, mp19, pBR322, pMB9, ColE1, pCR1, RP4, phage DNAs, and shuttle vectors such as pSA3 and pAT28. These and other cloning vectors are available from commercial vendors such as BioRad, Stratagene, and Invitrogen.

Expression vectors generally are replicable polynucleotide constructs that contain a polynucleotide encoding a αC polypeptide of interest. The polynucleotide encoding αC polypeptide is operatively linked to suitable transcriptional controlling elements, such as promoters, enhancers and terminators. For expression (i.e., translation), one or more translational controlling elements are also usually required, such as ribosome binding sites, translation initiation sites, and stop codons. These controlling elements (transcriptional and translational) can be derived from the H11 gene, or heterologous (i.e., derived from other genes or other organisms). A polynucleotide sequence encoding a signal peptide can also be included to allow a αC polypeptide to cross or lodge in cell membranes or be secreted from the cell. A number of expression vectors suitable for expression in eukaryotic cells including yeast, avian, and mammalian cells are known in the art. One example of an expression vector is pcDNA3 (Invitrogen, San Diego, Calif.), in which transcription is driven by the cytomegalovirus (CMV) early promoter/enhancer. This vector also contains recognition sites for multiple restriction enzymes for insertion of an αC polynucleotide of interest. Another example of an expression vector (system) is the baculovirus/insect system.

Also encompassed by the invention are expression systems suitable for use in antibody-targeted gene therapy comprising a αC polynucleotide. Suitable systems are described for instance by Brown et al. (1994) *Virol.* 198: 477–488; and Miyamura et al. (1994) *Proc. Natl. Acad. Sci. USA* 91:8507–8511.

The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (where the vector is an infectious agent, such as vaccinia virus, which is discussed below). The choice of introducing vectors or αC polynucleotides will often depend on features of the host cell.

Once introduced into a suitable host cell, expression of a αC polypeptide can be determined using any assay known in the art. For example, presence of αC polypeptide can be detected by RIA or ELISA of the culture supernatant (if the H11 polypeptide is secreted) or cell lysates.

A particularly useful expression vector for H11 polynucleotides is a vaccinia virus comprised of a H11 polynucleotide sequence, which can also be used in vaccine preparations. Moss (1991) *Science* 252:1662–1667. To introduce polynucleotide sequences encoding H11 polypeptide, including H11 polypeptide fragments, into vaccinia, the polynucleotide sequence of interest is first inserted into a plasmid containing a vaccinia virus promoter with flanking sequences homologous to vaccinia DNA not required for replication. Plasmid-containing cells are then infected with vaccinia, which leads to a low level of homologous recombination between plasmid and virus, with resultant transfer of the vaccinia promoter and H11 polypeptide-encoding polynucleotide sequence into the vaccinia virus genome. Typically, the H11 polynucleotide is inserted into the viral TK (thymidine kinase) gene. Insertion into the TK site attenuates the virus more than 10,000 fold compared to wild type. Flexner et al. (1980) *Vaccine* 88 (Cold Spring Harbor Laboratory), pp. 179–184. Recombinant virus is identified by the $TK^-$ phenotype. Preferably, expression of the H11 polynucleotide is under the control of the vaccinia early/late promoter (7.5 K), whereby the resultant H11 polypeptides can be expressed in infected cells throughout the life cycle of the virus. However, other promoters known in the art can be used, such as pH6, or synthetic promoters. Expression of the H11 polypeptide occurs in cells infected with the recombinant vaccinia or individuals immunized with the live recombinant vaccinia virus. Any one of several strains of vaccinia can be used, including, but not limited to, WR, ALVAC, and NYVAC.

A vector of this invention can contain one or more polynucleotides encoding a αC polypeptide. It can also contain polynucleotide sequences encoding other polypeptides that enhance, facilitate, or modulate the desired result, such as lymphokines, including, but not limited to, IL-2, IL-4, GM-CSF, TNF-α, and IFN-γ. A preferred lymphokine is GM-CSF. Preferred GM-CSF constructs are those which have been deleted for the AU-rich elements from the 3' untranslated regions and sequences in the 5' untranslated region that are capable of forming a hairpin loop. Also embodied in this invention are vaccinia vectors encoding for recombinant αC variants, such as scFvs, chimeras, and polymers.

Other embodiments of this invention are host cells transformed with αC polynucleotides and vectors comprising αC polynucleotide sequences, as described above. Both prokaryotic and eukaryotic host cells may be used. Prokaryotic hosts include bacterial cells, for example *E. coli* and *Mycobacteria*. Among eukaryotic hosts are yeast, insect, avian, plant and mammalian cells. Host systems are known in the art and need not be described in detail herein. Examples of mammalian host cells include CHO and NSO, obtainable from the European Collection of Cell Cultures (England). Transfection of NSO cells with a plasmid, for example, which is driven by a CMV promoter, followed by amplification of this plasmid in using glutamine synthetase provides a useful system for protein production. Cockett et al. (1990) *Bio/Technology* 8:662–667.

The host cells of this invention can be used, inter alia, as repositories of αC polynucleotides, or as vehicles for production of αC polynucleotides and polypeptides. They may also be used as vehicles for in vivo expression of αC polypeptides. The H11 polynucleotides of this invention can be used in expression systems to produce H11 polypeptides, intact H11, or recombinant forms of H11, such as are described below.

The polynucleotides of this invention have several uses. They are useful, for example, in expression systems for the production of αC. They are also useful as hybridization probes to assay for the presence of αC polynucleotide or related sequences in a sample using methods well known to those in the art. Further, the polynucleotides are also useful as primers to effect amplification of desired polynucleotides. The polynucleotides of this invention are also useful in pharmaceutical compositions including vaccines and for gene therapy.

The polynucleotides can also be used as hybridization probes for detection of αC encoding sequences. Suitable samples include cells transformed ex vivo for use in gene therapy. In one illustration, DNA or RNA is extracted from a sample, and optionally run on a gel and/or digested with restriction endonucleases. The processed sample polynucleotide is typically transferred to a medium suitable for washing. The sample polynucleotide is then contacted with the H11 polynucleotide probe under conditions that permit a stable duplex to form if the sample contains a matching αC sequence. Any stable duplexes formed are detected by any suitable means. For example, the αC polynucleotide probe can be supplied in labeled form, and label remaining with the sample after washing will directly reflect the amount of stable duplex formed. In a second illustration, hybridization is performed in situ. A suitably prepared tissue sample is overlaid with a labeled probe to indicate the location αC encoding sequences.

A short αC polynucleotide can also be used as a primer for a PCR reaction, particularly to amplify a longer sequence comprising a region hybridizing with the primer. This can be conducted preparatively, in order to produce polynucleotide for further genetic manipulation. It can also be conducted analytically, to determine whether a αC encoding polynucleotide is present, for example, in a sample of diagnostic interest.

Another use of the polynucleotides is in vaccines and gene therapy. The general principle is to administer the polynucleotide so that it either promotes or attenuates the expression of the polypeptide encoded therein. Thus, the present invention includes methods of inducing an immune response and methods of treatment comprising administration of an effective amount αC polynucleotides to an individual. In these methods, a αC polynucleotide encoding a αC polypeptide is administered to an individual, either directly or via cells transfected with the αC polynucleotide. Preferably, the αC polynucleotide is in the form of a circular plasmid, preferably in a supercoiled configuration. Preferably, the αC polynucleotide is replicated inside a cell. Thus, the αC polynucleotide is operatively linked to a suitable promoter, such as a heterologous promoter that is intrinsically active in cells of the target tissue type. Preferably, once in cell nuclei, plasmids persist as circular non-replicating episomal molecules. In vitro mutation can be carried out with plasmid constructs to encode, for example, molecules with greater affinity and/or avidity.

To determine whether plasmids containing αC polynucleotides are capable of αC expression in eukaryotic cells, cells such as COS-7, CHO, or HeLa can be transfected with the plasmids. Expression of αC is then determined by immunoassay; for example, by Western blot. Smaller αC polypeptides can be detected, for example, by constructing the plasmid so that the resultant αC polypeptide is fused with a tag, such as a target epitope or enzyme label. Further characterization of the expressed αC polypeptide can be achieved by purifying the peptide and then conducting one of the functional assays described herein.

In one mode of gene therapy, the polynucleotides of this invention are used for genetically altering cells ex vivo. In this strategy, cells removed from a donor or obtained from a cell line are transfected or transduced with vectors encoding a αC polypeptide, and then administered to a recipient. Suitable cells for transfection include peripheral blood mononuclear cells.

In another mode of gene therapy, the polynucleotides of this invention are used for genetically altering cells in vivo. The purpose includes, but is not limited to, treating various types of cancer.

αC polypeptides can be characterized in several ways. For instance, a αC polypeptide may be tested for its ability to bind specifically to cancer cells, for its ability to specifically inhibit the binding between cancer cells and intact H11. A αC polypeptide can also react with anti-CDR3 polypeptides. αC polypeptides can also be tested for their ability to palliate or ameliorate neoplastic disease, such as carcinomas. It is understood that only one of these properties need be present in order for a polypeptide to come within the scope of this invention, although preferably more than one of these properties is present.

The ability of a αC polypeptide to bind cancer cells or antigenic fractions thereof can be tested by immunoassay. Any form of direct binding assay is suitable. In one such assay, the cancer cell or the putative αC polypeptide is labeled. Suitable labels include radioisotopes such as $^{125}I$, enzymes such as peroxidase, fluorescent labels such as fluorescein, and chemiluminescent labels. Typically, the other binding partner is insolubilized (for example, by coating onto a microtiter plate) to facilitate washing. After combining the labeled component with the insolubilized component, the solid phase is washed and the amount of bound label is determined. Another such assay is a sandwich assay, in which the putative αC polypeptide is captured by a first anti-immunoglobulin on a solid phase and developed with αC antibody. In either of these examples, the extent of binding of αC is directly related to the amount of label bound to the solid phase.

To conduct the inhibition assays, the putative αC polypeptide is titered for its ability to decrease the binding of H11 to cancer cells. Either of the binding pairs in the reaction to be inhibited is labeled, while the other is typically insolubilized in order to facilitate washing. The putative αC polypeptide is typically mixed with the labeled component, and then the mixture is combined with the solid phase. Polypeptides with the characteristics of H11 will proportionately decrease the amount of label attached to the solid phase, compared with control polypeptides. This test may be more sensitive than measuring direct binding, because lower affinity interaction between αC and C antigen may be too weak to form a stable bond, but adequate to interfere with the binding of another ligand-receptor pair when present at sufficient concentration.

The present invention encompasses pharmaceutical compositions and immunogenic compositions containing αC either alone or in combination. Such pharmaceutical compositions and vaccines are useful for eliciting an immune response and treating neoplastic diseases, either alone or in conjunction with other forms of therapy, such as chemotherapy or radiotherapy.

The preparation of pharmaceutical compositions that contain αC antibody, or a polynucleotide or a polypeptide derivative thereof as an active ingredient is conducted in accordance with generally accepted procedures for the preparation of pharmaceutical preparations. See, for example, *Remington's Pharmaceutical Sciences* 18*th Edition* (1990), E. W. Martin ed., Mack Publishing Co., PA. Depending on the intended use and mode of administration, it may be desirable to process the active ingredient further in the preparation of pharmaceutical compositions. Appropriate processing may include sterilizing, mixing with appropriate non-toxic and non-interfering components, dividing into dose units, and enclosing in a delivery device.

Liquid pharmaceutically acceptable compositions can, for example, be prepared by dissolving or dispersing a polypeptide embodied herein in a liquid excipient, such as water, saline, aqueous dextrose, glycerol, or ethanol. The composition can also contain other medicinal agents, pharmaceutical agents, adjuvants, carriers, and auxiliary substances such as wetting or emulsifying agents, and pH buffering agents.

Pharmaceutical compositions of the present invention are administered by a mode appropriate for the form of composition. Typical routes include subcutaneous, intramuscular, intraperitoneal, intradermal, oral, intranasal, and intrapulmonary (i.e., by aerosol). Pharmaceutical compositions of this invention for human use are typically administered by a parenteral route, most typically intracutaneous, subcutaneous, or intramuscular.

Pharmaceutical compositions for oral, intranasal, or topical administration can be supplied in solid, semi-solid or liquid forms, including tablets, capsules, powders, liquids, and suspensions. Compositions for injection can be supplied as liquid solutions or suspensions, as emulsions, or as solid forms suitable for dissolution or suspension in liquid prior to injection. For administration via the respiratory tract, a preferred composition is one that provides a solid, powder, or liquid aerosol when used with an appropriate aerosolizer device. Although not required, pharmaceutical compositions are preferably supplied in unit dosage form suitable for administration of a precise amount. Also contemplated by this invention are slow release or sustained release forms, whereby a relatively consistent level of the active compound are provided over an extended period.

Compositions embodied in this invention can be assessed for their ability to recognize specifically a neoplasia. Accordingly, test compounds are prepared as a suitable pharmaceutical composition and administered to test subjects. Initial studies are preferably done in small animals such as mice or rabbits, optionally next in non-human primates and then ultimately in humans. Immunogenicity is preferably tested in individuals without a previous antibody response. A test composition in an appropriate dose is administered on an appropriate treatment schedule. It may be appropriate to compare different doses and schedules within the predicted range. Such testing is within the skill of one in the art.

Compositions of this invention are particularly suitable for administration to humans with a neoplastic disease. Especially relevant are melanoma, neuroblastoma, glioma, sarcoma, lymphoma, and small cell lung cancer.

Also included in this invention are methods for treating cancer. The methods comprise administering an amount of a pharmaceutical composition containing αC effective to achieve the desired effect, be it palliation of an existing tumor mass or prevention of recurrence. For treatment of cancer, the amount of a pharmaceutical composition administered is an amount effective in producing the desired effect. An effective amount can be provided in one or a series of administrations.

The effective amount of αC antigen binding fragments to be administered will depend upon several factors, such as the route of administration, the condition of the individual, and the desired objective. The term "therapeutically effective" means that the amount of antigen binding fragment used is of sufficient quantity to ameliorate the cancer. "Ameliorate" denotes a lessening of the detrimental effect of the cancer on the individual. Typically, if administered directly, the amount per administration is about 10 μg to 20 mg, preferably 250 μg to 10 mg, more preferably 300 μg to 5 mg, even more preferably 500 μg to 2.5 mg. Administrations are typically conducted on a weekly or biweekly basis until a desired, measurable parameter is detected, such as diminution of disease symptoms. Administration can then be continued on a less frequent basis, such as biweekly or monthly, as appropriate.

The various compositions of this invention can be used alone, or in conjunction with other active agents that promote the desired objective, or provide a desirable adjunct therapy. Suitable active agents include the anti-neoplastic drugs and bioresponse modifiers described above and effector cells such as those described by Douillard et al. (1986) *Hybridomas* (Supp. 1:5139).

When used for immunotherapy, αC can be unlabeled or labeled with a therapeutic agent as described above. These agents can be coupled either directly or indirectly to the polypeptides of the invention. One example of indirect coupling is by use of a spacer moiety. These spacer moieties, in turn, can be either insoluble or soluble (Diener et al. (1986) *Science* 231:148) and can be selected to enable drug release from αC at the target site. Alternatively, an αC and a therapeutic agent can be translated, synthesized, ligated or otherwise produced as a single molecule which has both αC and therapeutic agent functions. Examples of therapeutic agents which can be coupled to αC for immunotherapy include, but are not limited to, bioresponse modifiers, drugs, radioisotopes, lectins, and toxins. Bioresponse modifiers include lymphokines which include, but are not limited to, tumor necrosis factor, interleukins 1, 2, and 3, lymphotoxin, macrophage activating factor, migration inhibition factor, colony stimulating factor, and interferon. Interferons with which αC can be labeled include α-interferon, β-interferon, and γ-interferon (IFN-γ) and their subtypes.

In using radioisotopically conjugated αC for immunotherapy, certain isotypes may be more preferable than others depending on such factors as leukocyte distribution as well as isotype stability and emission. If desired, the malignant cell distribution can be evaluated by the in vivo diagnostic techniques described below. Depending on the malignancy, some emitters may be preferable to others. In general, alpha and beta particle-emitting radioisotopes are preferred in immunotherapy. For example, if an animal has solid tumor foci, as in a carcinoma, a high energy beta emitter capable of penetrating several millimeters of tissue, such as $^{90}$Y, may be preferable. On the other hand, if the malignancy consists of simple target cells, as in the case of leukemia, a short range, high energy alpha emitter, such as $^{212}$Bi, may be preferable. Radioisotopes which can be bound to the antigen binding fragments of the invention for therapeutic purposes include, but are not limited to, $^{125}$I, $^{131}$I, $^{90}$Y, $^{67}$Cu, $^{212}$Bi, $^{211}$At, $^{212}$Pb, $^{47}$Sc, $^{109}$Pd, and $^{188}$Re.

Lectins are proteins, usually isolated from plant material, which bind to specific sugar moieties. Many lectins are also able to agglutinate cells and stimulate lymphocytes. However, ricin is a toxic lectin which has been used immunotherapeutically. This is preferably accomplished by binding the alpha-peptide chain of ricin, which is responsible for toxicity, to the antibody molecule to enable site specific delivery of the toxic effect.

Toxins are poisonous substances produced by plants, animals, or microorganisms that, in sufficient dose, are often lethal. Diphtheria toxin is a substance produced by *Corynebacterium diphtheria* which can be used therapeutically. This toxin consists of an alpha and beta subunit which under proper conditions can be separated. The toxic A chain component can be bound to an antibody and used for site specific delivery to a neoplastic cell.

Thus, for example, αC can be used in combination with alpha-interferon. This treatment modality enhances Mab targeting of melanomas by increasing the expression of Mab reactive antigen by the melanoma cells. Greiner et al. (1987) *Science* 235:895. Alternatively, αC could be used, for example, in combination with IFN-γ to thereby activate and increase the expression of Fc receptors by effector cells which, in turn, results in an enhanced binding of the antigen binding fragments to the effector cell and killing of target malignant cells. Those of skill in the art will be able to select from the various biological response modifiers to create a desired effector function which enhances the efficacy of αC.

When αC is used in combination with various therapeutic agents, such as those described herein, the administration of both usually occurs substantially contemporaneously. The term "substantially contemporaneously" means that they are administered reasonably close together with respect to time. Usually, it is preferred to administer the therapeutic agent before αC. For example, the therapeutic agent can be administered 1 to 6 days before αC. The administration of the therapeutic agent can be daily, or at any other suitable interval, depending upon such factors, for example, as the nature of the malignancy, the condition of the patient and half-life of the agent.

Using αC, it is possible to design combination therapies. It may be desirable to administer a therapeutic agent, or agents, prior to the administration of αC in combination with effector cells and the same, or different, therapeutic agent or agents. For example, patients can be treated by first administering IFN-γ and interleukin-2 (Il-2) daily for 3 to 5 days, and on day 5 administering αC in combination with effector cells, IFN-γ, and Il-2.

The present invention also encompasses the use of liposomes with membrane bound αC to specifically deliver the liposome to the area of the tumor or neoplastic cells expressing C antigen. These liposomes can be produced such that they contain, in addition to αC, such immunotherapeutic agents as those described above which would then be released at the site of malignancy. Wolff et al. (1984) *Biochem. Biophys. Acta* 802:259. Another such delivery system described by Brown et al. (1994) *Virology* 198:

477–488; and Miyamura et al. (1994) *Proc. Natl. Acad. Sci. USA* 91:8507–8511 utilizes chimeric parvovirus B19 capsids for presentation of the antigen binding fragments. Such chimeric systems are encompassed for use in the claimed methods.

The dosage ranges for the administration of αC are those large enough to produce the desired effect in which the symptoms of the malignant disease are ameliorated without causing undue side effects such as unwanted cross-reactions, anaphylactic reactions, and the like. Generally, the dosage will vary with the patient's age, condition, sex and extent of the disease and can be determined by one of skill in the art. The dosage can be adjusted by the individual physician in the event of any complication. Dosage can vary from about 0.1 mg/kg to about 2000 mg/kg, preferably about 0.1 mg/kg to about 500 mg/kg, in one or more dose administrations daily, for one or several days. Generally, when αC are administered conjugated with therapeutic agents, lower dosages, comparable to those used for in vivo immunodiagnostic imaging, can be used.

Therapeutic compositions of αC can be administered by injection or by gradual perfusion. The αC antigen binding fragments can be administered intravenously, intraperitoneally, intramuscularly, subcutaneously, intracavity, intrathecally or transdermally, alone or in combination with effector cells.

Another method of administration is intralesionally, for instance by direct injection directly into the tumor. Intralesional administration of various forms of immunotherapy to cancer patients does not cause the toxicity seen with systemic administration of immunologic agents. Fletcher et al. (1987) *Lymphokine Res.* 6:45; Rabinowich et al. (1987) *Cancer Res.* 47:173; Rosenberg et al. (1989) *Science* 233: 1318; and Pizz et al. (1984) *Int. J. Cancer* 34:359.

αC is particularly suitable for use in treating and imaging brain cancer. When the site of delivery is the brain, the therapeutic agent must be capable of being delivered to the brain. The blood-brain barrier limits the uptake of many therapeutic agents into the brain and spinal cord from the general circulation. Molecules which cross the blood-brain barrier use two main mechanisms: free diffusion; and facilitated transport. Because of the presence of the blood-brain barrier, attaining beneficial concentrations of a given therapeutic agent in the CNS may require the use of specific drug delivery strategies. Delivery of therapeutic agents to the CNS can be achieved by several methods.

One method relies on neurosurgical techniques. In the case of gravely ill patients, surgical intervention is warranted despite its attendant risks. For instance, therapeutic agents can be delivered by direct physical introduction into the CNS, such as intraventricular, intralesional, or intrathecal injection. Intraventricular injection can be facilitated by an intraventricular catheter, for example, attached to a reservoir, such as an Ommaya reservoir. Methods of introduction are also provided by rechargeable or biodegradable devices. Another approach is the disruption of the blood-brain barrier by substances which increase the permeability of the blood-brain barrier. Examples include intra-arterial infusion of poorly diffusible agents such as mannitol, pharmaceuticals which increase cerebrovascular permeability such as etoposide, or vasoactive agents such as leukotrienes. Neuwelt and Rappoport (1984) *Fed Proc.* 43:214–219; Baba et al. (1991) *J. Cereb. Blood Flow Metab.* 11:638–643; and Gennuso et al. (1993) *Cancer Invest.* 11:638–643.

Further, it may be desirable to administer the compositions locally to the area in need of treatment; this can be achieved by, for example, local infusion during surgery, by injection, by means of a catheter, or by means of an implant, said implant being of a porous, non-porous, or gelatinous material, including membranes, such as silastic membranes, or fibers. A suitable such membrane is Gliadel® provided by Guilford Pharmaceuticals Inc.

Another method involves pharmacological techniques such as modification or selection of the αC to provide an analog which will cross the blood-brain barrier. Examples include increasing the hydrophobicity of the molecule, decreasing net charge or molecular weight of the molecule, or modifying the molecule, such as to resemble one normally transported across the blood-brain barrier. Levin (1980) *J. Med. Chem.* 23:682–684; Pardridge (1991) in: *Peptide Drug Delivery to the Brain*; and Kostis et al. (1994) *J. Clin. Pharmacol.* 34:989–996.

Encapsulation of αC in a hydrophobic environment such as liposomes is also effective in delivering drugs to the CNS. For example, WO 91/04014 describes a liposomal delivery system in which the drug is encapsulated within liposomes to which molecules have been added that are normally transported across the blood-brain barrier.

Another method of formulating αC to pass through the blood-brain barrier is encapsulation in cyclodextrin. Any suitable cyclodextrin which passes through the blood-brain barrier can be employed, including, but not limited to, β-cyclodextrin, γ-cyclodextrin and derivatives thereof. See generally, U.S. Pat. Nos. 5,017,566, 5,002,935 and 4,983, 586. Such compositions can also include a glycerol derivative as described by U.S. Pat. No. 5,153,179.

Yet another method takes advantage of physiological techniques such as conjugation of αC to a transportable agent to yield a new chimeric transportable αC. For example, vasoactive intestinal peptide analog (VIPa) exerts its vasoactive effects only after conjugation to a Mab to the specific carrier molecule transferrin receptor, which facilitates the uptake of the VIPa-Mab conjugate through the blood-brain barrier. Pardridge (1991); and Bickel et al. (1993) *Proc. Natl. Acad. Sci. USA* 90:2618–2622. Several other specific transport systems have been identified, these include, but are not limited to, those for transferring insulin, or insulin-like growth factors I and II. Other suitable, non-specific carriers include, but are not limited to, pyridinium, fatty acids, inositol, cholesterol, and glucose derivatives. Certain prodrugs have been described whereby, upon entering the central nervous system, the drug is cleaved from the carrier to release the active drug. U.S. Pat. No. 5,017, 566.

Suitable subjects include those who are suspected of being at risk of a pathological effect of any neoplasia, particularly carcinoma, are suitable for treatment with the pharmaceutical compositions of this invention. Those with a history of cancer are especially suitable. Suitable human subjects for therapy comprise two groups, which can be distinguished by clinical criteria. Patients with "advanced disease" or "high tumor burden" are those who bear a clinically measurable tumor. A clinically measurable tumor is one that can be detected on the basis of tumor mass (e.g., by palpation, CAT scan, or X-Ray; positive biochemical or histopathological markers on their own may be insufficient to identify this population). A pharmaceutical composition embodied in this invention is administered to these patients to elicit an anti-tumor response, with the objective of palliating their condition. Ideally, reduction in tumor mass occurs as a result, but any clinical improvement constitutes a benefit. Clinical improvement includes decreased risk or rate of progression or reduction in pathological consequences of the tumor.

A second group of suitable subjects is known in the art as the "adjuvant group". These are individuals who have had a history of cancer, but have been responsive to another mode of therapy. The prior therapy may have included, but is not restricted to, surgical resection, radiotherapy, and traditional chemotherapy. As a result, these individuals have no clinically measurable tumor. However, they are suspected of being at risk for progression of the disease, either near the original tumor site, or by metastases.

This group can be further subdivided into high-risk and low-risk individuals. The subdivision is made on the basis of features observed before or after the initial treatment. These features are known in the clinical arts, and are suitably defined for each different cancer. Features typical of high risk subgroups are those in which the tumor has invaded neighboring tissues, or who show involvement of lymph nodes.

Another suitable group of subjects is those with a genetic predisposition to cancer but who have not yet evidenced clinical signs of cancer. For instance, women testing positive for a genetic mutation associated with breast cancer, but still of childbearing age, may wish to receive αC treatment prophylactically to prevent the occurrence of cancer until it is suitable to perform preventive surgery.

A pharmaceutical composition embodied in this invention is administered to patients in the adjuvant group, or in either of these subgroups, in order to elicit an anti-cancer response. Ideally, the composition delays recurrence of the cancer, or even better, reduces the risk of recurrence (i.e., improves the cure rate). Such parameters may be determined in comparison with other patient populations and other modes of therapy.

Of course, crossovers between these two patient groups occur, and the pharmaceutical compositions of this invention can be administered at any time that is appropriate. For example, αC therapy can be conducted before or during traditional therapy of a patient with high tumor burden, and continued after the tumor becomes clinically undetectable. αC therapy can be continued in a patient who initially fell in the adjuvant group, but is showing signs of recurrence. The attending physician has the discretion to determine how or when the compositions of this invention are to be used.

Various compounds and compositions of this invention have other clinical indications, of which the following section provides only a survey.

One indication is the treatment of cells ex vivo. This may be desirable for experimental purposes, or for treatment of an individual with a neoplastic disease. In one example, αC is administered to a culture of cells, such as peripheral blood cells obtained from a donor, or a suitable cell line. About 0.5 to 2 μg/mL of H11 is an effective dose for this purpose. In a second example, donor cells are genetically altered with an expression vector of this invention, to provide for ongoing secretion of αC after administration of the cells to the recipient.

The present invention further encompasses methods for in vivo detection of cancer cells. A diagnostically effective amount of detectably labeled αC is given to the subject in need of tumor imaging. The term "diagnostically effective" means that the amount of detectably labeled αC is administered in sufficient quantity to enable detection of the neoplasia.

The concentration of detectably labeled αC which is administered should be sufficient such that the binding to those cells having C antigen is detectable compared to the background. Further, it is desirable that the detectably labeled αC be rapidly cleared from the circulatory system in order to give the best target-to-background signal ratio.

As a rule, the dosage of detectably labeled αC for in vivo diagnosis is somewhat patient-specific and depends on such factors as age, sex, and extent of disease. The dosage of αC can vary from about 0.01 mg/m$^2$ to about 500 mg/m$^2$, preferably 0.1 mg/m$^2$ to about 200 mg/m$^2$, most preferably about 0.1 mg/m$^2$ to about 10 mg/m$^2$. Such dosages may vary, for example, depending on number of injections given, tumor burden, and other factors known to those of skill in the art. For instance, tumors have been labeled in vivo using cyanine-conjugated Mabs. Ballou et al. (1995) *Cancer Immunol. Immunother.* 41:257–263.

For in vivo diagnostic imaging, the type of detection instrument available is a major factor in selecting a given radioisotope. The radioisotope chosen must have a type of decay which is detectable for a given type of instrument. Still another important factor in selecting a radioisotope for in vivo diagnosis is that the half-life of the radioisotope be long enough so that it is still detectable at the time of maximum uptake by the target, but short enough so that deleterious radiation with respect to the individual is minimized. Ideally, a radioisotope used for in vivo imaging lacks a particle emission, but produces a large number of photons in the 140–250 keV range, to be readily detected by conventional gamma cameras. For imaging, doses of $^{111}$In-H11-scFv (for instance, 2 mg of scFv labeled with 5 mCi of $^{111}$Indium) the range administered is about 0.01 mg to 20 mg, more preferably about 0.1–10 mg and even more preferably about 1–5 mg per patient.

For in vivo diagnosis, radioisotopes can be bound to αC either directly or indirectly by using an intermediate functional group. Intermediate functional groups which are often used to bind metallic ion radioisotopes to immunoglobulins are the bifunctional chelating agents such as diethylene triaminepentacetic acid (DTPA) and ethylenediaminetetraacetic acid (EDTA) and similar molecules. Typical examples of metallic ions which can be bound to αC are $^{111}$In, $^{97}$Ru, $^{67}$Ga, $^{68}$Ga, $^{72}$As, $^{89}$Zr, $^{90}$Y, and $^{201}$T.

αC can also be labeled with a paramagnetic isotope for purposes of in vivo diagnosis, as in magnetic resonance imaging (MRI) or electron spin resonance (ESR). In general, any conventional method for visualizing diagnostic imaging can be utilized. Usually, gamma and positron emitting radioisotopes are used for camera imaging and paramagnetic isotopes for MRI. Elements which are particularly useful in such techniques include $^{157}$Gd, $^{55}$Mn, $^{162}$DY, $^{52}$Cr, and $^{56}$Fe. αC can also be labeled with a fluorescent dye for the purpose of in vivo diagnosis.

αC can also be used to detect neoplasias using in vitro assays. Samples are taken from the patient and subject to any suitable immunoassay with αC to detect the presence of C antigen. This is particularly useful in detecting lymphomas and leukemias where the tumor cells bearing C antigen are circulating in the patient's bloodstream.

αC can also be used to monitor the course of amelioration of malignancy in an individual. Thus, by measuring the increase or decrease in the number of cells expressing C antigen or changes in the concentration of C antigen present in various body fluids, it is possible to determine whether a particular therapeutic regimen aimed at ameliorating the malignancy is effective.

The present invention encompasses kits containing αC. Diagnostic procedures using αC can be performed by diagnostic laboratories, experimental laboratories, practitioners, or private individuals. The clinical sample is optionally pre-treated for enrichment of the target being tested for. The user then applies a reagent contained in the kit in order to detect the changed level or alteration in the diagnostic component.

Each kit comprises αC used for detecting C antigen in the sample. Optionally, the reagent may be conjugated with a label to permit detection of any complex formed with the target in the sample. In another option, a second reagent is provided that is capable of combining with the first reagent after it has found its target and thereby supplying the detectable label. For example, labeled anti-mouse IgG may be provided as a secondary reagent for use with intact αC. Labeled avidin may be provided as a secondary reagent when the primary reagent has been conjugated with biotin.

The kits can be employed to test a variety of biological samples, including both liquid samples, cell suspensions and tissue samples. Suitable assays using αC that can be supplied in kit form include those described herein. Each reagent is supplied in a solid form or dissolved/suspended in a liquid buffer suitable for inventory storage, and later for exchange or addition into the reaction medium when the test is performed. Suitable packaging is provided. The kit can optionally provide additional components that are useful in the procedure. These optional components include, but are not limited to, buffers, capture reagents, developing reagents, labels, reacting surfaces, means for detection, control samples, instructions, and interpretive information.

The foregoing description provides, inter alia, detailed methods for preparing H11, along with H11 encoding polynucleotides, H11 polypeptide fragments, and other derivatives. A practitioner of ordinary skill in the art can practice embodiments of this invention by referring to the sequence data for H11, which is provided herein. The following examples are provided to illustrate but not limit the claimed invention.

EXAMPLE 1

Method of Obtaining Mab H11

Mab NBGM1/H11 ("H11"), is a human monoclonal IgM antibody reactive against the following human tumor tissues and corresponding tumor cell lines: glioma, malignant melanoma, colon adenocarcinoma and breast adenocarcinoma. In vitro characterization of Mab NBGM1/H11 is shown in Example 2.

Fusion of H11 was accomplished by fusing $8 \times 10^6$ peripheral blood lymphocytes obtained from a 64 year old male with a low grade glioma with the TM-H2-SP2 human myeloma cell line. The TM-H2-SP2 cell line is the immunoglobulin nonsecreting subline of the IgG(κ) parental cell line TM-H2, a hypoxanthine guanine phosphoribosyltransferase (EC 2.4.2.8)-deficient derivative of an unknown human myeloma-like line selected in 0.8% methylcellulose for its resistance to 6-thioguanine (6 μg/mL) and failure to grow in hypoxanthine-aminopterin-thymidine medium. The karyotype of TM-H2-SP2 is 46±2, XX.

The resultant viable hybridoma cells were split among 40 microwells at a density of $2 \times 10^5$ cells/mL and 0.2 mL/well. The frequency of outgrowth from fusion H11 was 12 of 40 (30%) potential hybridoma-containing wells. Outgrowth resulting from sustained growth is defined as prolonged growth with culture expansion for periods longer than 3 months; instances of hybridoma growth failure occurring later than 3 months post-fusion were not observed.

Screening of hybridoma clones was performed by antigen-capture enzyme-linked immunosorbent assay (ELISA) in microtiter plates using polyclonal anti-human IgM or IgG as coating antigen. A hybridoma culture supernatant was positive if the measured optical density (O.D.) value exceeded the mean background level of a control culture supernatant by greater than two standard deviations.

Selection of hybridoma clone NBGM1/H11 was performed by cell-fixed ELISA. Culture supernatants from 6 microtiter wells, which tested high for IgM or IgG secretion, were screened against previously attached and fixed human tumor cell lines: Glioblastoma (SKMG-1 and D-54MG); melanoma (A-375); and colon adenocarcinoma (SK-CO-1). A hybridoma supernatant was considered to be positive if the measured O.D. value exceeded the mean background level of control culture supernatants by greater than two standard deviations. Mab produced by hybridoma NBGM1/H11 continues to be reactive against these tumor cell lines. The "H11" antibodies are $IgM_{(k)}$.

Characterization of the hybridoma NBGM1/H11 seed bank was performed by Microbiological Associates (Rockville, Md.). The cells tested negative for (1) bacterial and fungal contamination, (2) mycoplasma contamination, (3) HIV-1 and HIV-2 antigens and (4) HTLV-1 and HTLV-2 antigens.

The methods used for the characterization of Mab NBGM1/H11 include: antigen-capture ELISA, antigen ELISA, cell-fixed ELISA, flow cytometry, immunoperoxidase staining of human tumor cell lines and immunohistochemistry of human tumor and normal tissues (see following examples).

Binding characteristics of this human Mab to human tumor cell lines as determined by flow cytometry, immunoperoxidase staining, cell-fixed ELISA and antigen ELISA (i.e., tumor cell freeze-thaw extracts) are presented below.

EXAMPLE 2

Binding of Mab H11 to Human Glioblastoma (SKMG-1) and Melanoma (A375) Cell Lines by Flow Cytometric Analysis In order to determine the binding of Mab H11 to tumor cells, tumor cells growing in T-flasks were detached by incubation with PBS-EDTA. Cells were collected by low speed centrifugation, washed with ice-cold PBS-1% FBS, centrifuged and the supernatant aspirated. The cell pellet was resuspended in culture medium spiked with one of the following: a control human melanoma IgM; hybridoma NBGM1/H11 culture supernatant; or PBS containing purified Mab H11; and incubated on ice for 30 minutes. After incubation, the cells were collected by centrifugation, washed by resuspension in PBS-FBS and centrifuged. The cell pellet was then incubated for 30 min. with FITC-conjugated goat anti-human IgM. After incubation, the cells were washed with PBS-FBS. Finally, the cells were resuspended in PBS-FBS propidium iodide (PI) was added and the cells washed. PI-positive and FITC-positive cells were analyzed by flow cytometry.

Figure 2:
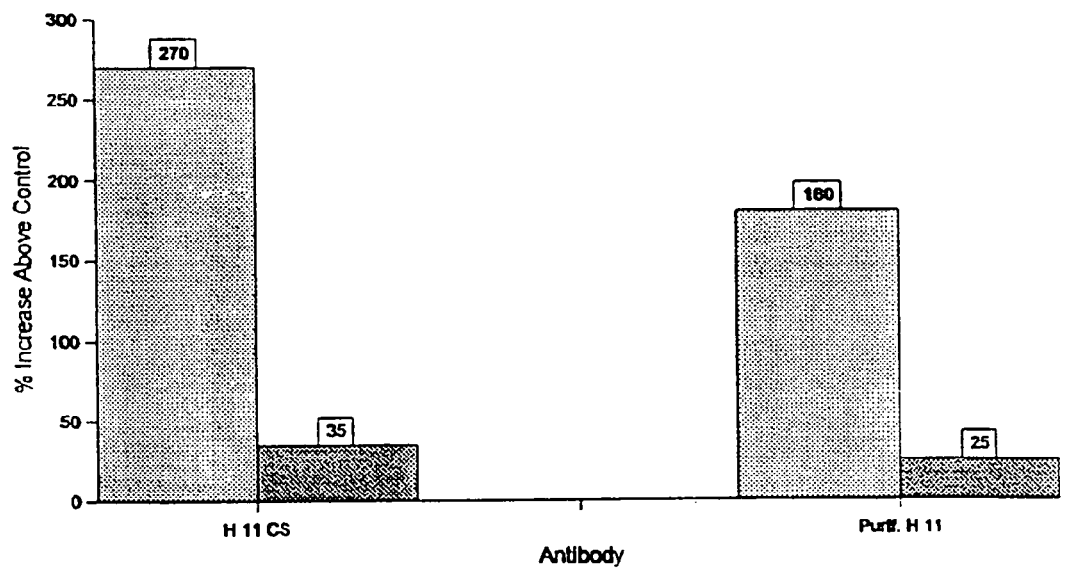
FIG. 2 depicts flow cytometric analysis of cells recognized by H11.
Figure 3:
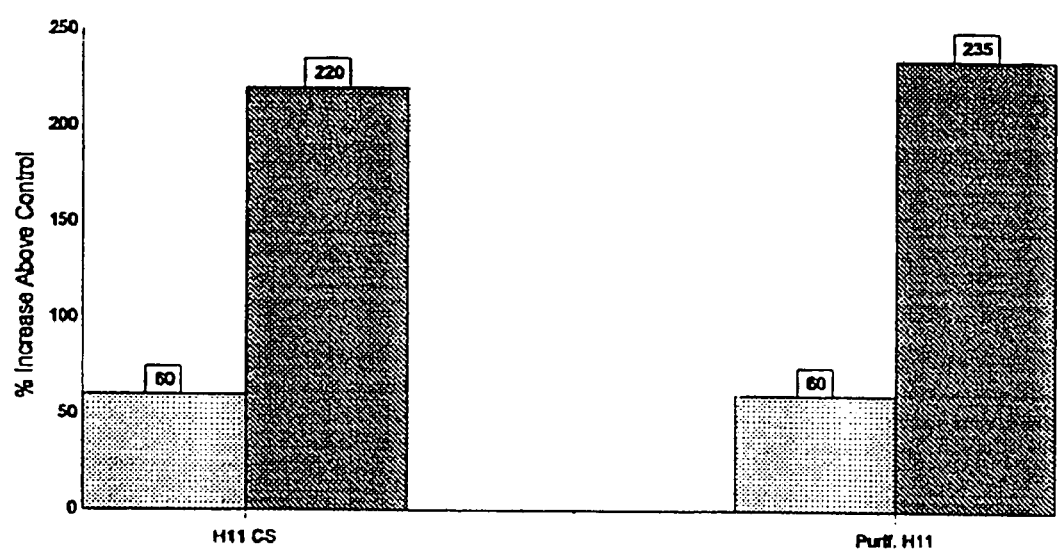
FIG. 3 depicts flow cytometric analysis of cells recognized by H11.
Figure 4:
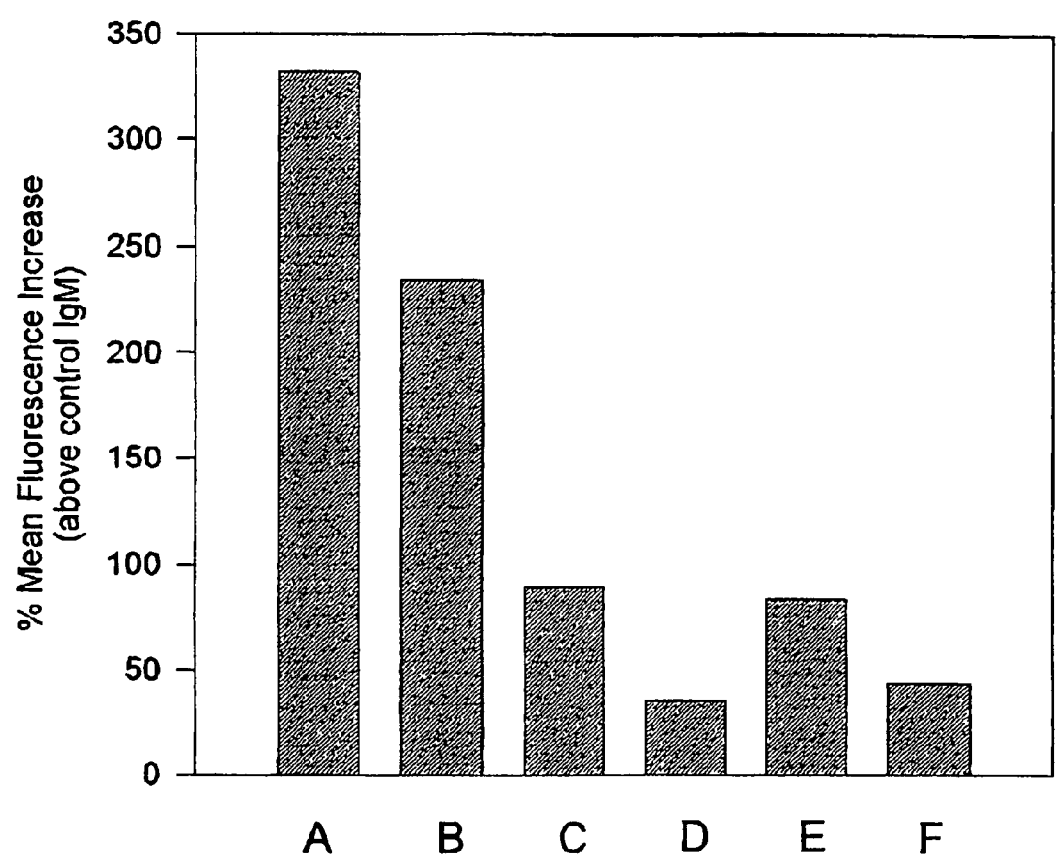
FIG. 4 depicts flow cytometric analysis of cells recognized by H11. A is A-375 (melanoma), B is SKMG-1 (glioma), C is SK-BR-3 (breast adenocarcinoma), D is HT-29 (colon adenocarcinoma), E is MB-468 (breast carcinoma), and F is T47D (breast carcinoma).

The results of the flow cytometric analyses are shown in FIGS. 2, 3 and 4. These results indicate that crude and purified forms of Mab H11 bind to a cell surface-associated antigen(s) expressed on live human tumor cell lines, including glioblastoma, melanoma, breast adenocarcinoma and colon adenocarcinoma.

EXAMPLE 3

Binding of Mab H11 to Freeze-Thaw Extracts of Human Tumor Cell Lines by ELISA Analysis In order to determine the ability of H11 to bind specifically to human tumor antigen(s), ELISA plates were coated with human tumor cell extracts prepared by repeated freezing and thawing of glioblastoma (SKMG-1), breast adenocarcinoma (BT-20, MB-468 and MB-453), colon adenocarcinoma (SK-CO-1 and HT-29) cells.

The coated ELISA plates were incubated for 16–18 hours at 2–8° C. The plates were blocked with PBS-3% BSA for 1 hr at room temperature. Then the plates were incubated with either Mab H11 in PBS or control IgM in PBS or culture medium for 2 hrs at room temperature. The plates were washed and incubated with biotinylated anti-human IgM followed by incubation with biotinylated anti-human IgM followed by incubation with streptavidin-conjugated alkaline phosphatase for 1 hr. After washing, p-nitrophenyl phosphate substrate was added to each plate and, after incubation, the plates were read at 405 nm in an ELISA plate reader.

Figure 5:
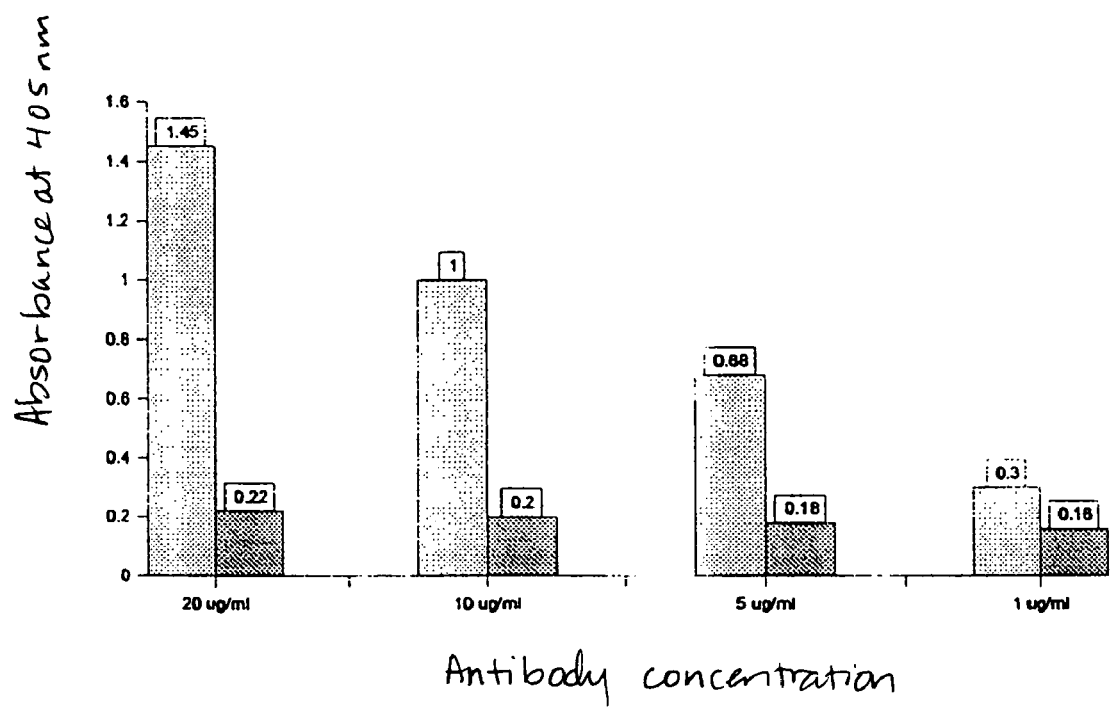
FIG. 5 depicts binding of H11 to tumor cell extracts. The light bars represent H11 and the dark bars represent control antibody.
Figure 6:
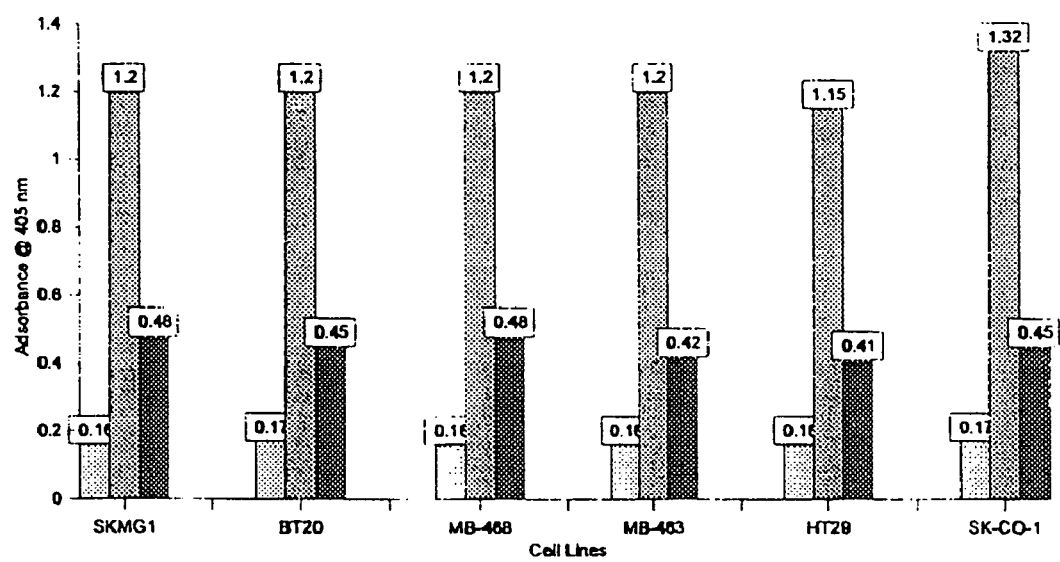
FIG. 6 depicts binding of H11 to tumor cell extracts.

The binding of Mab H11 to the tumor cell extracts is shown in FIGS. 5 and 6. These results indicate that Mab H11 binds to tumor cell extracts prepared from glioblastoma, breast adenocarcinoma and colon adenocarcinoma cells in a dose-dependent manner.

EXAMPLE 4

Binding of Mab H11 to Human Tumor Cells Determined by Immunoperoxidase Staining In order to determine immunoreactivity of H11, the following experiment was performed. Tumor cells were grown in 24-well plates on coverslips for 48–96 hrs. The cells were washed with PBS, fixed with formaldehyde and incubated with 5% normal goat serum on PBS for 30 min. After washing, the cells were incubated for 2 hrs with either hybridoma NBGM1/H11 culture supernatants or purified Mab H11 (10 μg/mL) in PBS or culture medium spiked with control human myeloma IgM (10 μg/mL) for 2 hrs. The cells were then washed and incubated with anti-human IgM conjugated to HRP. Finally, the cells were washed, incubated with DAB substrate to visualize Mab H11 binding, counterstained with hematoxylin and mounted in GVA.

The results of the immunoreactivity of Mab H11 are shown in Table 3 where reactivity is indicated as negative (−−), weak positive (+), positive (++), strong positive (+++). These results indicate that, as determined by immunoperoxidase staining, the epitope recognized by Mab H11 is expressed by a number of different types of human tumor cells and cell lines.

TABLE 3

| | REACTIVITY | |
|---|---|---|
| CELL LINES/TYPE OF TUMOR | Control IgM | Mab H11 |
| HUMAN GLIOBLASTOMA | | |
| SKMG 1 | −− | +++ |
| U-118 MG | −− | ++ |
| U-87 MG | −− | ++ |

TABLE 3-continued

| | REACTIVITY | |
|---|---|---|
| CELL LINES/TYPE OF TUMOR | Control IgM | Mab H11 |
| HUMAN MALIGNANT MELANOMA | | |
| A-375 | −− | +++ |
| SK-MEL-5 | −− | ++ |
| HUMAN COLON ADENOCARCINOMA | | |
| SK-CO-1 | −− | ++ |
| HUMAN BREAST ADENOCARCINOMA | | |
| MG-468 | −− | ++ |
| MB-453 | −− | + |
| BT-20 | −− | ++ |
| BT-474 | −− | ++ |
| HUMAN KIDNEY ADENOCARCINOMA | | |
| SW-839 | −− | ++ |
| HUMAN OSTEOGENIC SARCOMA | | |
| SAOS-2 | −− | ++ |
| HUMAN OVARY ADENOCARCINOMA | | |
| SK-OV-3 | −− | ++ |

EXAMPLE 5

Binding of Mab H11 to Human Tumor Cell Lines Determined by Cell-Fixed ELISA

The binding of H11 to human tumor cells and cell lines was also determined by cell-fixed ELISA. Growing tumor cells were detached from the T-flask surface by incubating with EDTA-PBS. Cells were collected by centrifugation, washed with PBS, resuspended in culture medium, counted, and 50 μl of cell suspension containing 5,000–10,000 cells placed in each well of 96-well ELISA plates. After allowing the cells to attach to the plates, the culture supernatants were removed and the plates were blocked with PBS-BSA. The cells were then incubated with different concentrations (1–20 μg/mL) of either Mab H11 or control human myeloma IgM for 2 hrs. After incubation, the plates were washed, incubated with biotin-conjugated goat anti-human IgM, washed again and incubated with streptavidin-conjugated alkaline phosphatase. Finally, the plates were washed, incubated with p-nitrophenyl phosphate substrate and read at 405 nm in an ELISA plate reader.

Figure 7:
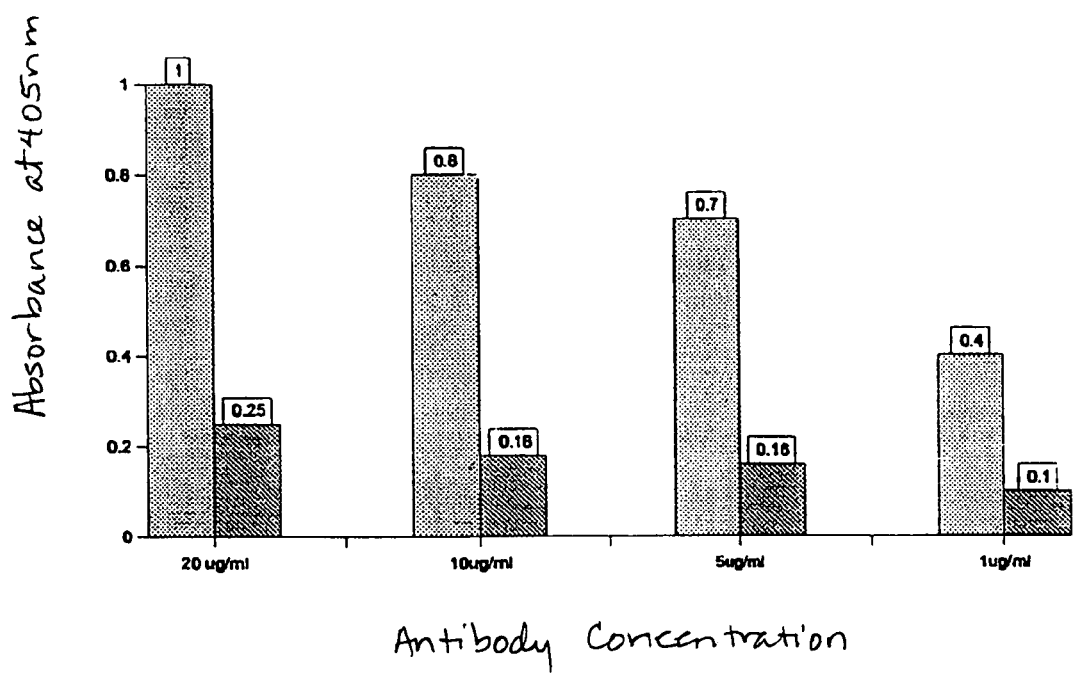
FIG. 7 depicts binding of H11 to human tumor cell lines by cell-fixed ELISA. The light bars are H11 IgM and the dark bars are control IgM.

Results of the reactivity of Mab H11 to human tumor cell lines by cell-fixed ELISA are shown in Table 4 and FIG. 7. In Table 4, Control IgM 10 μg/mL and H11 10 μg/mL were used for testing the reactivity, and values are given as absorbance at 405 nm±standard deviation. These results indicate that: 1) Mab H11 reacts strongly with glioblastoma cells (SKMG-1), even at a low concentration of 1 μg/mL, whereas control IgM at 20 μg/mL does not react with SKMG-1 cells; and 2) Mab H11 recognizes the tumor antigen(s) present on numerous tumor cell lines (breast adenocarcinoma, colon adenocarcinoma, malignant melanoma, neuroblastoma, glioblastoma, lung adenocarcinoma, small cell lung carcinoma and prostate adenocarcinoma). The degree for Mab reactivity varies both with the type of cancer and the tumor cell lines. The reactivity of Mab H11 for cancer and tumor cells was between three and ten times greater than that of the control IgM.

TABLE 4

| Cell lines/Tumor Type | Reactivity (O.D. at 405 nm) | |
|---|---|---|
| | Control IgM | Mab H11 |
| Human Glioblastoma | | |
| SKMG-1 | 0.21 ± 0.01 | 0.95 ± 0.06 |
| D-54-MG | 0.13 ± 0.02 | 0.43 ± 0.07 |
| U-87MG | 0.13 ± 0.02 | 0.60 ± 0.01 |
| Neuroblastoma | | |
| SK-N-SH | 0.14 ± 0.02 | 0.96 ± 0.06 |
| SK-N-MC | 0.17 ± 0.03 | 1.00 ± 0.05 |
| Malignant Melanoma | | |
| SK-MEL-5 | 0.18 ± 0.03 | 1.42 ± 0.04 |
| SK-MEL-28 | 0.19 ± 0.03 | 1.79 ± 0.05 |
| Breast adenocarcinoma | | |
| MB-453 | 0.68 ± 0.18 | 2.85 ± 0.14 |
| MB-468 | 0.60 ± 0.03 | 2.39 ± 0.10 |
| SK-BR-3 | 0.60 ± 0.03 | 2.14 ± 0.13 |
| T47D | 0.58 ± 0.01 | 2.13 ± 0.04 |
| BT-20 | 0.57 ± 0.02 | 2.07 ± 0.13 |
| BT-474 | 0.61 ± 0.03 | 2.20 ± 0.17 |
| Lung adenocarcinoma | | |
| SW-900 | 0.20 ± 0.02 | 0.68 ± 0.10 |
| SK-LU-1 | 0.19 ± 0.02 | 0.57 ± 0.07 |
| A-427 | 0.22 ± 0.01 | 0.88 ± 0.07 |
| Small cell lung carcinoma | | |
| NCI-H69 | 0.25 ± 0.04 | 1.42 ± 0.20 |
| NCI-H82 | 0.20 ± 0.09 | 1.16 ± 0.13 |
| Colon adenocarcinoma | | |
| SK-Co-1 | 0.27 ± 0.03 | 0.98 ± 0.11 |
| HT-29 | 0.37 ± 0.02 | 1.78 ± 0.20 |
| Prostate adenocarcinoma | | |
| PC-3 | 0.17 ± 0.01 | 0.60 ± 0.01 |
| DU-145 | 0.15 ± 0.01 | 0.52 ± 0.01 |
| Kidney adenocarcinoma | | |
| SW-839 | 0.2 ± 0.01 | 1.43 ± 0.01 |
| Osteogenic sarcoma | | |
| SAOS-2 | 0.24 ± 0.02 | 1.22 ± 0.07 |
| U-2 OS | 0.13 ± 0.04 | 1.93 ± 0.05 |
| Bladder cell carcinoma | | |
| T-24 | 0.13 ± 0.01 | 1.25 ± 0.03 |
| Ovarian adenocarcinoma | | |
| SK0OV-3 | 0.12 ± 0.01 | 1.14 ± 0.02 |
| Larynx carcinoma | | |
| HEP-2 | 0.25 ± 0.01 | 1.25 ± 0.01 |
| Normal human fibroblast | | |
| GM-8333 | 0.13 ± 0.01 | 0.39 ± 0.01 |

EXAMPLE 6

Immunoanatomic Distribution and Immunopathologic Analysis of H11

Immunohistochemistry was used to determine H11 specificity for micro-anatomical detail and heterogeneity in tissues and tumors. Limitations of this technique include possible false negative results due to low levels of expression of the molecule under study, as well as false positive results (cross-reactivity) due to antibody-binding to similar epitopes or epitopes shared by other antigens. To address these limitations, this study was carried out at the highest concentration of antibody that did not show non-specific binding. This allowed for detection of all levels of cross-reactivity in different tissues. Also, fixation analysis established the best combination of antigenic staining intensity and morphological preservation. The present example presents results obtained from IMPATH Inc., New York, retained to study the cellular specificity and antigen expression of H11, on a selected panel of cryostat-cut frozen sections of normal and tumor tissues. The study used an indirect immunoperoxidase technique.

Histologically normal human tissues were obtained from surgical and autopsy specimens. These fresh tissues were embedded in OCT (Miles Laboratories, Inc., Naperville, Ill.) in cryomolds, snap-frozen in isopentane, cooled by liquid nitrogen. The tissues from IMPATH's frozen tissue bank were cut at 5 microns, placed on poly-L-lysine coated slides, air-dried, and stored at −70° C.

H11, received on wet ice and stored at 2–8° C., was supplied non-biotinylated at a concentration of 200 µg/mL, total volume of 3.0 mL. A human myeloma IgM (Pierce Cat. #31146), also supplied by Novopharm, was used as the negative control. Both antibodies were diluted in phosphate buffered saline to the same working concentrations dictated by titration analysis of antibody H11. The peroxidase-labeled secondary antibody was a goat anti-human IgM (American Qualex, San Clemente, Calif., lot #AI 12PN) diluted in PBS to 1:500.

Immunoperoxidase Techniques: Immunohistochemical studies were performed using an indirect immunoperoxidase method. The cryostat cut sections were removed from the −70° C. freezer, air-dried and fixed according to the fixation protocol (fixation details, provided below). Tissue sections were blocked for 10 minutes with 5% normal goat serum diluted in PBS, then incubated with the primary antibody overnight at 4° C. Slides were washed in PBS, followed by a wash with 0.5% Tween/PBS solution, then PBS again. Endogenous peroxidase activity was blocked with a 30 minute 3% hydrogen peroxide/methanol incubation, followed by 3 washes of PBS. The sections were then incubated with goat anti-human IgM (peroxidase-labeled) secondary antibody for 15 minutes, at room temperature, and washed in PBS as described above.

The peroxidase reaction was visualized by incubating tissue sections for 2–5 minutes with 3,3-diaminobenzidine-tetrahydrochloride (DAB) (Sigma Chemical Co., St. Louis, Mo.). Tissue sections were thoroughly washed, counterstained with a modified Harris hematoxylin (Fisher Scientific, Fairlawn, N.J.) dehydrated through graded alcohols, cleared in xylene, and coverslipped. Tissues that demonstrated high levels of background staining with the negative control antibody were repeated with more extensive washing. Human breast carcinoma (F95-036), supplied by IMPATH, was the positive control for H11. Negative controls substituted the primary test antibody with purified human myeloma IgM.

The purpose of the fixation analysis was to establish the conditions which provide the optimal combination of antigenic staining intensity and morphological preservation. The positive control tissue was tested with five fixation protocols, including no fixation. The fixation protocols tested were 10% neutral buffered formalin (23–25° C.), acetone (2–8° C.), methyl/acetone (1:1 V/V, 2–8° C.) and 95% ethanol (23–25° C.). For this study, 10% neutral buffered formalin (NBF) gave optimal results for H11.

Using 10% NBF as the fixative, serial antibody dilutions (20.0 µg/mL to 0.1 µg/mL) were tested on the positive control, human breast carcinoma. A concentration of 10.0

µg/mL of antibody H11 gave optimal results—maximum staining intensity without significant background staining of the negative control.

The results obtained are depicted in Tables 5 and 6. Table 5 depicts H11 reactivity on normal tissues and Table 6 depicts H11 reactivity on human tumors.

TABLE 5

| Tissue | Tested Positive/Total | Range of Reactivity (0–3+) |
| --- | --- | --- |
| Adrenal | 0/3 | 0 |
| Bladder | 0/3 | 0 |
| Bone Marrow | 1/3 | 1+ |
| Brain | 0/3 | 0 |
| Breast | 0/3 | 0 |
| Cervix | 0/3 | 0 |
| Esophagus | 0/3 | 0 |
| Eye | 0/3 | 0 |
| Heart | 0/3 | 0 |
| Kidney | 0/3 | 0 |
| Large Intestine | 0/3 | 0 |
| Liver | 0/3 | 0 |
| Lung | 0/3 | 0 |
| Lymph Node | 0/3 | 0 |
| Muscle | 0/3 | 0 |
| Ovary | 0/2 | 0 |
| Pancreas | 0/3 | 0 |
| Parotid | 0/3 | 0 |
| Pituitary | 0/1 | 0 |
| Prostate | 0/3 | 0 |
| Skin | 0/3 | 0 |
| Small intestine | 0/3 | 0 |
| Spinal cord | 0/3 | 0 |
| Spleen | 0/3 | 0 |
| Stomach | 0/3 | 0 |
| Testis | 0/3 | 0 |
| Thymus | 0/3 | 0 |
| Thyroid | 0/3 | 0 |
| Tonsil | 1/3 | 1+ |
| Uterus | 0/3 | 0 |
| WBC | 0/3 | 0 |

TABLE 6

| Tumor | Tested Positive/Total | % of Tumor Cells Staining | Range of Reactivity (0–3+) |
| --- | --- | --- | --- |
| Breast carcinoma | 2/3 | 30–90 | 1–3+ |
| Colon carcinoma | 3/3 | 40–70 | 1–2+ |
| Glioma | 4/6 | 30–90 | 1–2+ |
| Gastric carcinoma | 3/3 | 30–50 | 1–2+ |
| Lung adenocarcinoma | 3/4 | 10–70 | 1–2+ |
| Lung squamous carcinoma | 3/3 | 10–95 | 1–3+ |
| Lung small cell carcinoma | 1/2 | 30 | 1+ |
| Lymphoma | 8/8 | 10–95 | 1–3+ |
| Melanoma | 3/3 | 20–95 | 1–2+ |
| Ovarian carcinoma | 3/3 | 20–30 | 1–3+ |
| Prostate carcinoma | 3/3 | 20–95 | 1–2+ |
| Sarcoma | 0/3 | 0 | 0 |

The results obtained indicate that weak (1+) to strong (3+) reactivity was observed in over 70% of the positive control sample. The antigen recognized by H11 has a restricted pattern of distribution. H11 was largely unreactive with normal human tissues tested in the IMPATH system. All simple epithelial cells, as well as the stratified epithelia and squamous epithelia of different organs were found to be unreactive. Reactivity was also not seen in neuroectodermal cells, including those in the brain, spinal cord and peripheral nerves. Mesenchymal elements such as skeletal and smooth muscle cells, fibroblasts, and endothelial cells were negative. Tissues of lymphoid origin including bone marrow, lymph node, spleen, and thymus were largely unreactive with antibody H11. Weak (1+) reactivity was observed in rare cells in one specimen of bone marrow and in the germinal centers of one of three specimens of tonsil tested.

Positive immunoreactivity was observed in almost all specimens of tumor tested including breast, colon, glioma, gastric, lung (adeno, squamous, and small cell), lymphoma, melanoma, ovarian, and prostate. Reactivity was seen in 10% to greater than 95% of the tumor cells present in these specimens; staining intensity ranged from weak (1+) to strong (3+). Antibody H11 was, however, unreactive with all three specimens of sarcoma tested. Some but not all normal counterparts of the tumor cells, when present in the specimens, were reactive with H11. A few normal cells present in breast, gastric and prostate carcinoma were reactive with antibody H11. The large granular cells that were reactive with antibody H11 are believed to be inflammatory cells of the eosinophile-mast cell lineage.

In summary, antibody H11 is largely unreactive with normal human tissues with the exception of some normal tissues present in tumors. The H11 antibody detects an antigen that is expressed in almost all of the tumors tested.

EXAMPLE 7

H11 Cloning, Expression and Immunologic Reactivity

In order to determine the ability of H11-scFv antibody fragments to bind specifically to cancer cells, the following experiments were performed.

The single chain antibody constructs were made by the following procedure. Primers specific to the 5' and 3' ends of the H11 kappa and mu V regions were synthesized on an Applied Biosystems DNA synthesizer. All the primers contained a restriction endonuclease site for cloning. Primers 5 and 6 also contained additional nucleotides that encode a (SGGGG)$_3$ linker. The primers used are listed in Table 7 where the restriction endonuclease site introduced is underlined.

TABLE 7

| Primer | Sequence (5'→3') | Site Introduced |
| --- | --- | --- |
| 1. | TATGAAGACACCAGGCCGATATTGTGTTGACGCAG (SEQ ID NO:7) | Bbs1 |
| 2. | TATCCGGATGCAGCCACAGTTCGTTT (SEQ ID NO:8) | BspE1 |
| 3. | TATTCGGACAGGTGCAGCTGGTGGAG (SEQ ID NO:9) | BspE1 |
| 4. | TATGGATCCTGAGGAGACGGTGACCGT (SEQ ID NO:10) | BamH1 |
| 5. | TATATATCCGGAGGTGGTGGATCAGGTGGAGGTGGCTCCCAGGTGCAGCTGGTGGAGTCT (SEQ ID NO:11) | BspE1 |

TABLE 7-continued

| Primer | Sequence (5'→3') | Site Introduced |
|---|---|---|
| 6. | ACCT<u>CCGGA</u>ACCGCCACCGCCAGAGACAGATGGTGCAGCCACATTC (SEQ ID NO:12) | BspE1 |

PCR reactions were carried out using primers 1 and 2 for the kappa dimer, primers 3 and 4 for the mu dimer, primers 1 and 6 for the kappa monomer and primers 4 and 5 for the mu monomer. The PCR fragments were then purified and digested with their respective restriction endonucleases. The coding nucleotides are depicted in SEQ ID NOS:13 and 16 and the complementary nucleotides are depicted in SEQ ID NOS:15 and 18, respectively.

Figure 8:
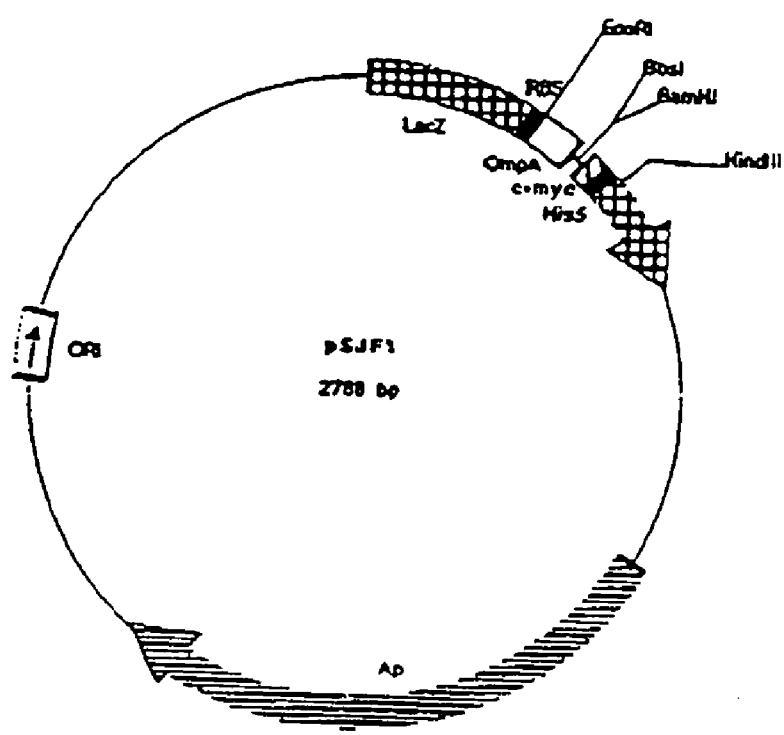
FIG. 8 depicts a schematic of the expression vector pSJF1.

The expression vector pSJF1 containing a ribosome binding site, OmpA signal peptide sequence, c-myc (9E10) detection tag and histidine tail (See FIG. 8) was prepared by cutting with Bbs1 and BamH1. The monomer and dimer constructs were assembled by ligating the respective kappa and mu fragments into pSJF1 and transforming them into competent TG1 E. coli. Resulting colonies were screened by colony PCR and restriction endonuclease digests to confirm the correct size inserts and the sequences were verified by dideoxy fluorescent sequencing.

Transformed TG1 containing either the H11 monomer or dimer expression plasmid were shaken at 26° C. for 24 hours followed by the addition IPTG to a final concentration of 0.1 µM. The cells were incubated for a further 16 hours and then harvested by centrifugation. The periplasmic proteins containing the H11 antibody were released by treatment with sucrose buffer (25% sucrose, 1 mM EDTA, 10 mM Tris pH 8.0) followed by ice cold shock buffer (10 mM Tris 8.0, 0.5 mM MgCl$_2$). Expression was verified by polyacrylamide gel electrophoresis and Western Blotting. The antibody was purified using a nickel-charged column (Pharmacia HiTrap chelating column) and the bound antibody was eluted with an increasing gradient of imidazole. The purified antibody was dialyzed against PBS/0.02% sodium azide and concentrated to 0.5 mg/mL.

Figure 9:
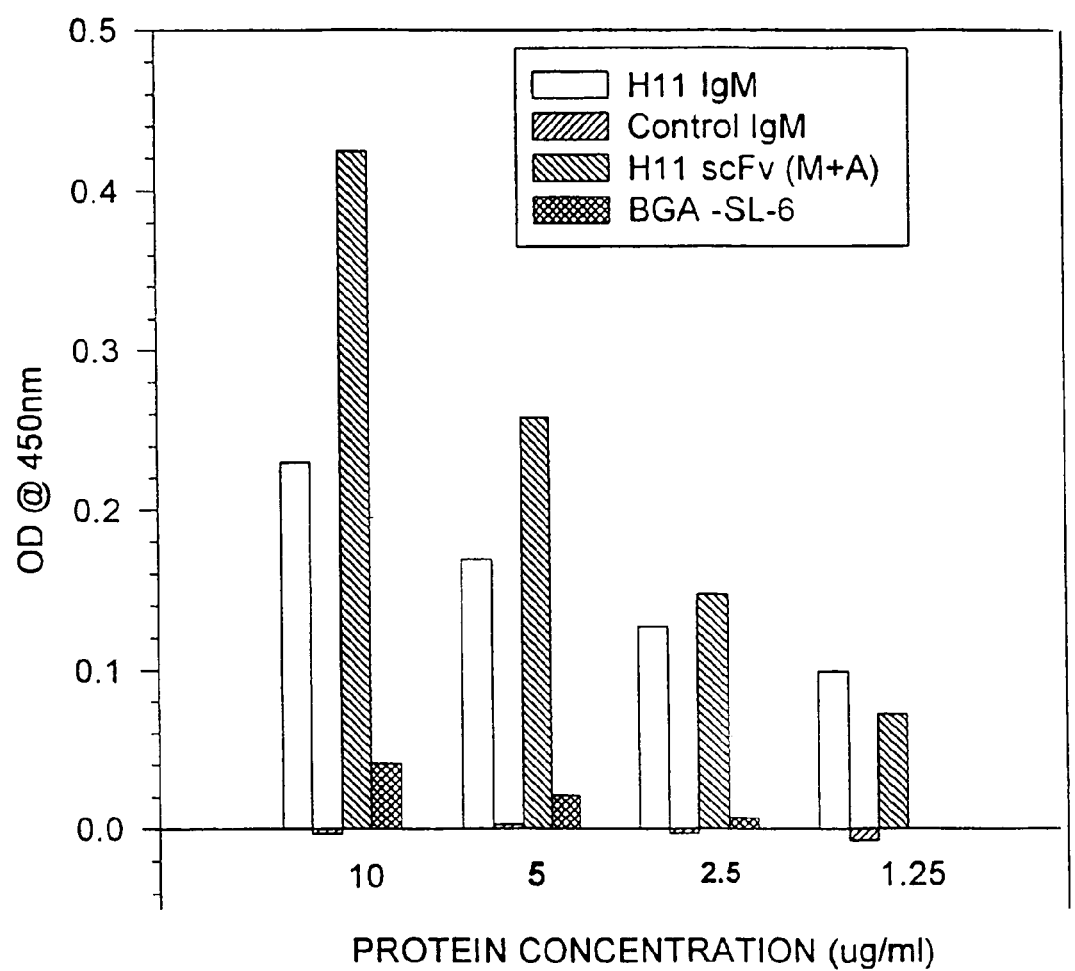
FIG. 9 depicts the determination of the antigenic similarities between Mab H11 and H11-scFv by cell fixed ELISA. Reactivity was determined by rabbit antibody to H11 scFv.

The antigenic similarities between Mab H11 and H11-scFv were also determined by cell fixed ELISA. ELISA plates coated with A375 cells were incubated with Mab H11, control IgM, H11-scFv or control BGA-scFv followed by incubation with rabbit anti-human IgM antibody or rabbit anti-scFv antibody as appropriate. The detection was by goat anti-rabbit IgG-horse radish peroxidase followed by substrate. The results, shown in FIG. 9, demonstrate a high affinity of both H11 IgM and H11-scFv, and a low affinity of both the control IgM and BGA-SL-6.

In order to determine the specificity of biotinylated H11-scFv relative to a biotinylated control scFv, the following experiment was performed. Human tumor cells were fixed to ELISA plates and incubated with either biotinylated H11-scFv or biotinylated BGA scFv (control) as described above.

Figure 10:
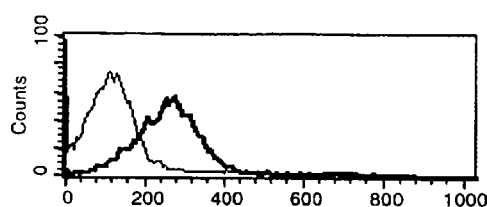
FIG. 10 depicts the relative fluorescence intensity of biotinylated H11-scFv (thick line) and BGA scFv (thin line) to lymphoma cells.
Figure 10:
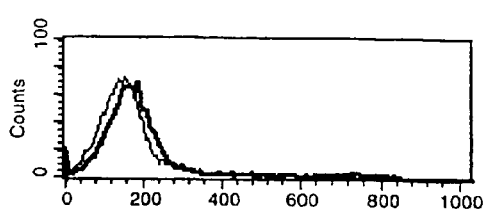
Figure 10:
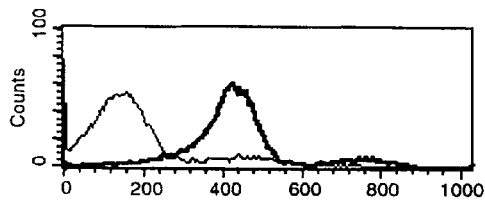
Figure 10:
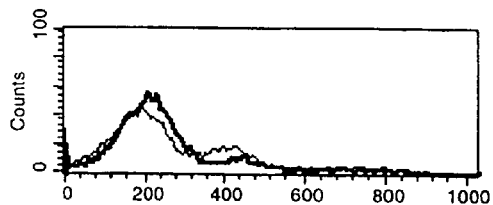

Biotinylated H11-scFv also demonstrated a much greater affinity (between 8- and 50-fold) for tumor cell lines than the control in cell fixed ELISA. Data corresponding to a concentration of 2.5 µg/mL of H11-scFv or BGA scFv is shown in Table 8 and FIG. 10.

Figure 11:
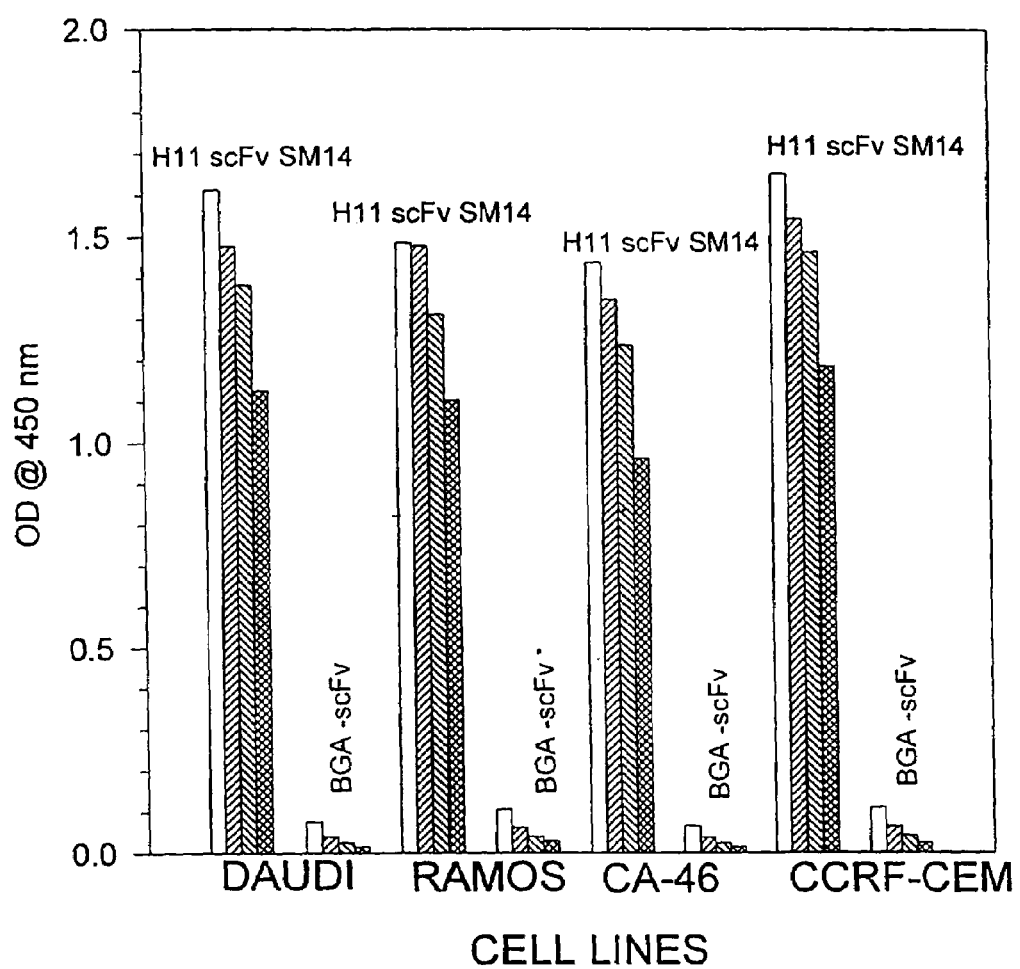
FIG. 11 depicts the titration of the reactivity of biotinylated H11-scFv for the binding to lymphoma cells, RAMOS, Daudi. CA-46 and CCRF-CEM cells as determined by cell fixed ELISA. The antibody concentrations decrease from an initial 10 µg/mL (open bar) to 5 µg/mL, then 2.5 µg/mL and finally, 1.25 µg/mL (doubly cross-hatched line).

FIG. 11 illustrates the portion of Table 8 related to the titration of reactivity of biotinylated H11-scFv for the binding to lymphoma cells Daudi, Ramos, CA-46 and CCRF-CEM cells. At every concentration tested (1.25 to 10 µg/mL), H11-scFv demonstrated a high affinity for lymphoma cells, but BGA scFv did not.

TABLE 8

| | Reactivity (O.D. at 450 nm ± SD) | |
|---|---|---|
| | Biotinylated BGA scFv | Biotin-H11-scFv |
| Tumor Cell Lines | | |
| Human Glioblastoma | | |
| SKMG-1 | 0.01 ± 0.01 | 0.56 ± 0.04 |
| U-118MG | 0.01 ± 0.02 | 0.47 ± 0.03 |
| D-54MG | 0.01 ± 0.00 | 0.50 ± 0.02 |
| Neuroblastoma | | |
| SK-N-MC | 0.01 ± 0.00 | 0.50 ± 0.02 |
| Malignant Melanoma | | |
| SK-MEL-5 | 0.02 ± 0.01 | 0.61 ± 0.04 |
| A-375 | 0.12 ± 0.03 | 0.97 ± 0.03 |
| SK-MEL-28 | 0.02 ± 0.00 | 0.71 ± 0.04 |
| Breast adenocarcinoma | | |
| T47D | 0.02 ± 0.00 | 0.64 ± 0.03 |
| MB-468 | 0.01 ± 0.00 | 0.65 ± 0.01 |
| SK-BR-3 | 0.01 ± 0.00 | 0.58 ± 0.02 |
| BT-20 | 0.01 ± 0.00 | 0.54 ± 0.06 |
| BT-474 | 0.01 ± 0.00 | 0.60 ± 0.01 |
| Lung adenocarcinoma | | |
| SW-9000 | 0.01 ± 0.00 | 0.41 ± 0.02 |
| SK-LU-1 | 0.01 ± 0.00 | 0.45 ± 0.03 |
| A-427 | 0.01 ± 0.00 | 0.40 ± 0.05 |
| Colon adenocarcinoma | | |
| SK-Co-1 | 0.01 ± 0.00 | 0.56 ± 0.01 |
| HT-29 | 0.01 ± 0.00 | 0.53 ± 0.06 |
| LS17T | 0.01 ± 0.00 | 0.57 ± 0.02 |
| Osteogenic sarcoma | | |
| SAOS-2 | 0.02 ± 0.00 | 0.88 ± 0.06 |
| U-2 OS | 0.02 ± 0.00 | 0.93 ± 0.01 |
| Bladder cell carcinoma | | |
| T-24 | 0.02 ± 0.01 | 0.97 ± 0.05 |
| Ovarian adenocarcinoma | | |
| SK-OV-3 | 0.01 ± 0.00 | 0.77 ± 0.02 |
| Larynx carcinoma | | |
| HEP-2 | 0.02 ± 0.00 | 0.08 ± 0.04 |
| Prostate carcinoma | | |
| DU-145 | 0.01 ± 0.00 | 0.42 ± 0.02 |
| PC-3 | 0.01 ± 0.00 | 0.36 ± 0.01 |
| Small cell lung carcinoma | | |
| NCI-H82 | 0.01 ± 0.00 | 0.44 ± 0.02 |
| NCI-69 | 0.01 ± 0.00 | 0.44 ± 0.01 |

TABLE 8-continued

| | Reactivity (O.D. at 450 nm ± SD) | |
|---|---|---|
| | Biotinylated BGA scFv | Biotin-H11-scFv |
| Lymphoma cell lines | | |
| Chronic myelogenous leukemia | | |
| K-562 | 0.02 ± 0.00 | 0.65 ± 0.00 |
| Acute lymphoblastic leukemia | | |
| CEM | 0.04 ± 0.00 | 1.4 ± 0.03 |
| Burkitt Lymphoma | | |
| CA-46 | 0.02 ± 0.00 | 1.2 ± 0.02 |
| RAMOS | 0.04 ± 0.00 | 1.3 ± 0.02 |
| DAUDI | 0.02 ± 0.00 | 1.38 ± 0.01 |

In order to verify the specificity of biotinylated H11-scFv for cancerous cells, the following experiment was performed. Malignant and normal tissue specimens were prepared and incubated with biotinylated H11-scFv as described above.

The H11-scFv was used to stain sections of tumor and normal tissues. The results are depicted in Table 8 for normal tissues and Table 9 for tumor tissues.

Figure 12:
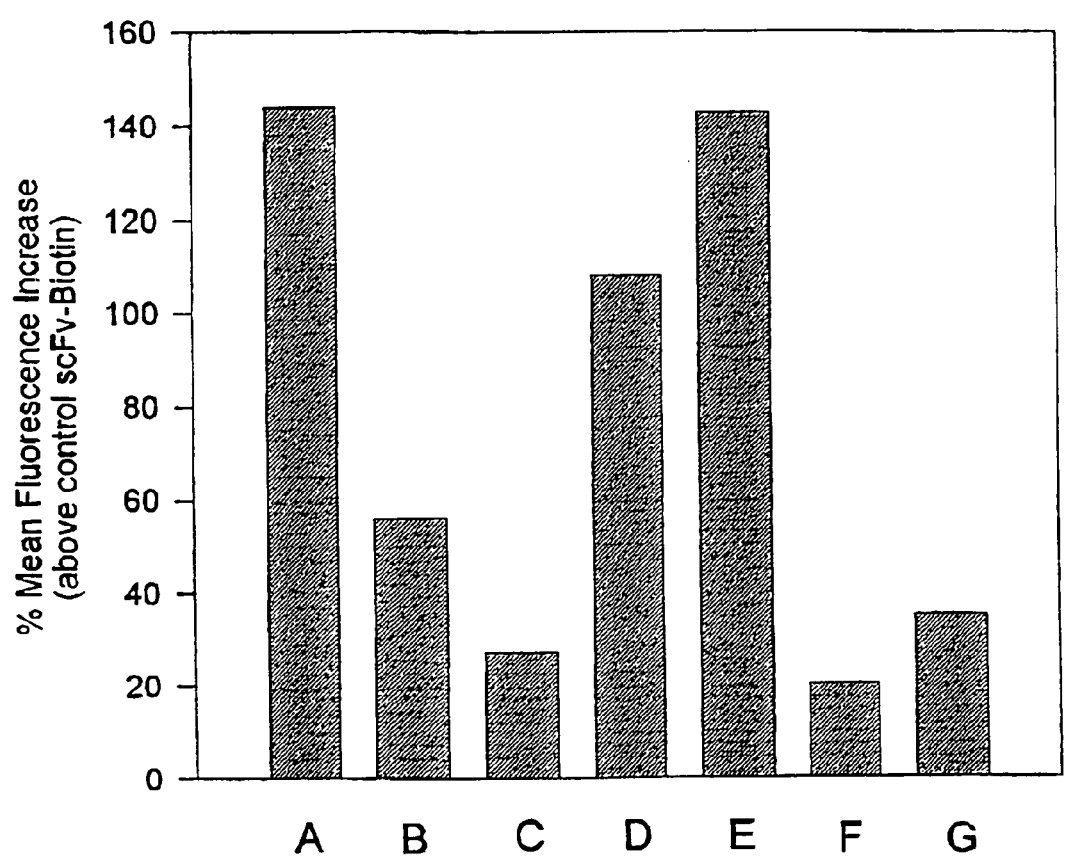
FIG. 12 depicts the relative fluorescence intensity of H11-scFv and control scFv binding to tumor cell lines. A is A-375 (melanoma), B is SK-BR-3 (breast adenocarcinoma), C is HT-29 (colon adenocarcinoma), D is CA-46 (Burkitt's lymphoma), E is RAMOS (Burkitt's lymphoma), F is H9 (T cell lymphoma), and G is CCRF-CEM (acute lymphoblastoid lymphoma).

FIG. 12 depicts the relative fluorescence intensity of H11-scFv and control scFv to tumor cell lines.

The data in Table 9 demonstrate that biotinylated H11-scFv genera lly does not react to normal tissues. Almost all of the norm al tissues tested demonstrated no measurable reactivity, with only a weakly positive signal generated by normal pancreas and peripheral nerve tissues. In Table 9, -ve indicates no measurable activity and indicates weakly positive activity.

TABLE 9

| Normal Tissues | Reactivity of Biotinylated H11-scFv (50 µg/mL) |
|---|---|
| Cortex | -ve |
| Breast | -ve |
| Colon | -ve |
| Heart | -ve |
| Liver | -ve |
| Lymph node | -ve |
| Prostate | -ve |
| Thyroid | -ve |
| Adrenal | -ve |
| Cerebellum | -ve |
| Lung | -ve |
| Pancreas | +/- |
| Peripheral Nerve | +/- |
| Skin | -ve |
| Spleen | -ve |
| Smooth muscle | -ve |
| Stomach | -ve |
| Thymus | -ve |

TABLE 10

| Tissue Type | Number of positives/Total samples tested | Percentage of Tumor Cells staining | Range of Reactivity (0–+3) |
|---|---|---|---|
| Breast carcinoma | 27/31 | 40/60 | 1–3+ |
| Colon carcinoma | 23/26 | 80/100 | 1–3+ |
| Melanoma | 13/14 | 50/70 | 1–3+ |
| Prostate carcinoma | 17/20 | 20/70 | 1–2+ |

TABLE 10-continued

| Tissue Type | Number of positives/Total samples tested | Percentage of Tumor Cells staining | Range of Reactivity (0–+3) |
|---|---|---|---|
| Cervix squamous cell carcinoma | 22/24 | nd | 1–2+ |
| Cervix adenocarcinoma | 9/9 | nd | 1–2+ |
| Kaposi Sarcoma | 7/8 | nd | 1–2+ |
| Benign Colon | 0/2 | 0 | 0 | nd: not determined

The results presented in Table 10 indicate that positive staining was found in most breast (27/31) and colon (23/26) and prostate (17/20) carcinoma samples tested. Positive staining was found at 25 µg/mL concentration of H11-scFv. Although the staining was predominantly detected in tumor cells, various degrees of reactivity were also found on stroma and adjacent tissue. The H11-scFv was also tested for its specificity for normal tissue. The results obtained are presented in Table 11 which summarizes the immunohistochemistry staining of H11-scFv with normal human tissue sections.

TABLE 11

| Tissue | H11-scFv (25 µg/mL) | 3B1 scFv (25 µg/mL) |
|---|---|---|
| Adrenal | ± | –~± |
| Cerebellum | – | – |
| Cortex | – | – |
| Colon | ± | – |
| Breast | –~± | – |
| Kidney | ± | –~± |
| Aorta | –~± | – |
| Heart | ± | –~± |
| Liver | ±~+ | ± |
| Lung | – | – |
| Lymph node | – | – |
| Pancreas | –~± | – |
| Pituitary | ±~+ | – |
| Prostate | –(focal ±) | –(focal ±) |
| Peripheral nerve | –~± | – |
| Skin | –(sweat gland ±) | –(sweat gland ±) |
| Spleen | –~± | – |
| Small intestine | –~± | – |
| Stomach | –~± | – |
| St. muscle | –~± | –~± |
| Thymus | –~± | – |
| Thyroid | –~± | – |
| S94-7474-2 (Colon Car. control) | ++ | – |

EXAMPLE 8

Reactivity of H11-scFv to Live Tumor Cells as Determined by Flow Cytometry

In order to test the reactivity of H11-scFv to live tumor cells, cells from tumor cell lines were prepared for flow cytometry as described above in Example 2. Tumor cells were incubated with either biotinylated H11-scFv or control biotinylated scFv as described above at a protein concentration of 100 µg/mL or 200 µg/mL. The reactivity was determined as the mean fluorescence and % positive cells. A biotinylated H11-scFv was prepared as described above and at a protein concentration of either 100 µg/mL or 200 µg/mL. The mean fluorescence and % positive cells are shown in Table 12 where # is biotinylated 3B1 as control scFv; * is biotinylated BGA SL-6 as control scFv;  is PBS 5% FCS as control; and * is Biotin-5B1 as control scFv.

TABLE 12

| Cell Line | Protein conc'n (µg/mL) | Mean Fluorescence | | % Positive Cells | |
|---|---|---|---|---|---|
| | | Biotinylated 3B1 scFv # | Biotinylated H11-scFv | Biotinylated 3B1 scFv # | Biotinylated H11-scFv |
| SK-BR-3 (Breast adenocarcinoma) | 200 | 149 | 233 | 11 | 36 |
| MB-468 (Breast adenocarcinoma) | 200 | 144 | 156 | 9 | 11 |
| A-375 (Melanoma) | 200 | 111 | 207 | 10 | 80 |
| A-375 (Melanoma) | 200 | 161* | 235 | 28 | 76 |
| LS-174T (Colon adenocarcinoma) | 200 | 182 | 233 | 24 | 37 |
| HT-29 (Colon adenocarcinoma) | 200 | 141 | 179 | 12 | 18 |
| SKMG-1 (Glioma) | 100 | 148** | 206 | 9 | 31 |
| | 100 | 189** | 224 | 14 | 27 |
| H9 (T cell Lymphoma) | 100 | 185*** | 145 | 20 | 13 |
| WI-38 (Human diploid lung cells) | 100 | 293*** | 255 | 26 | 15 |

Figure 13:
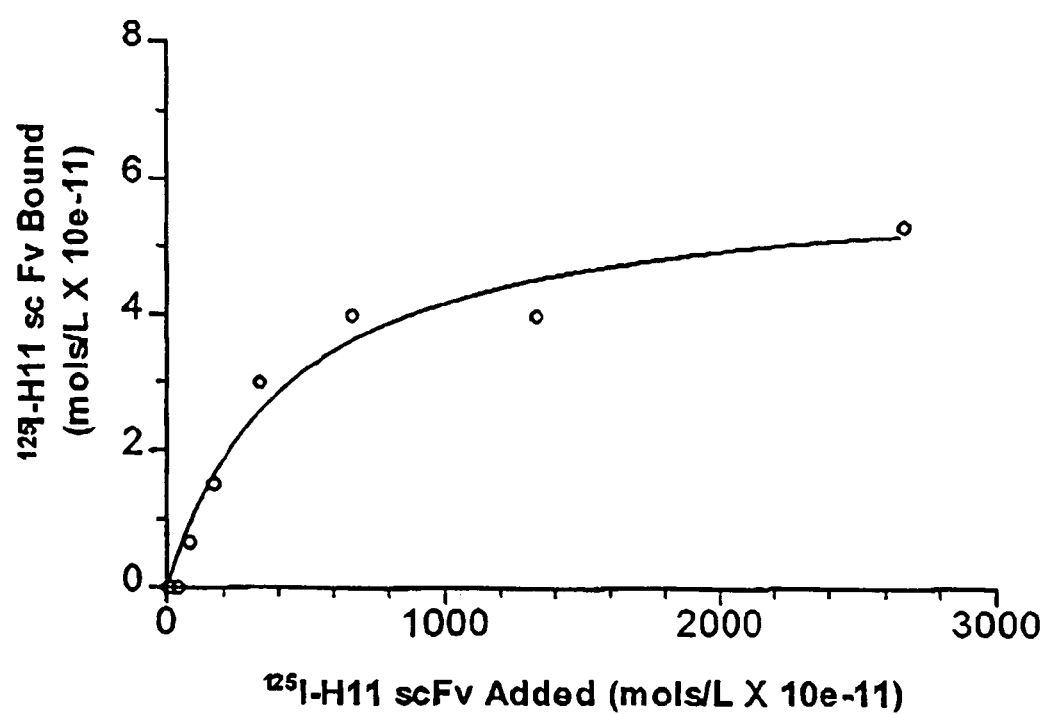
FIG. 13 depicts the binding of $^{125}$I-H11-scFv to LS174T cells.
Figure 14:
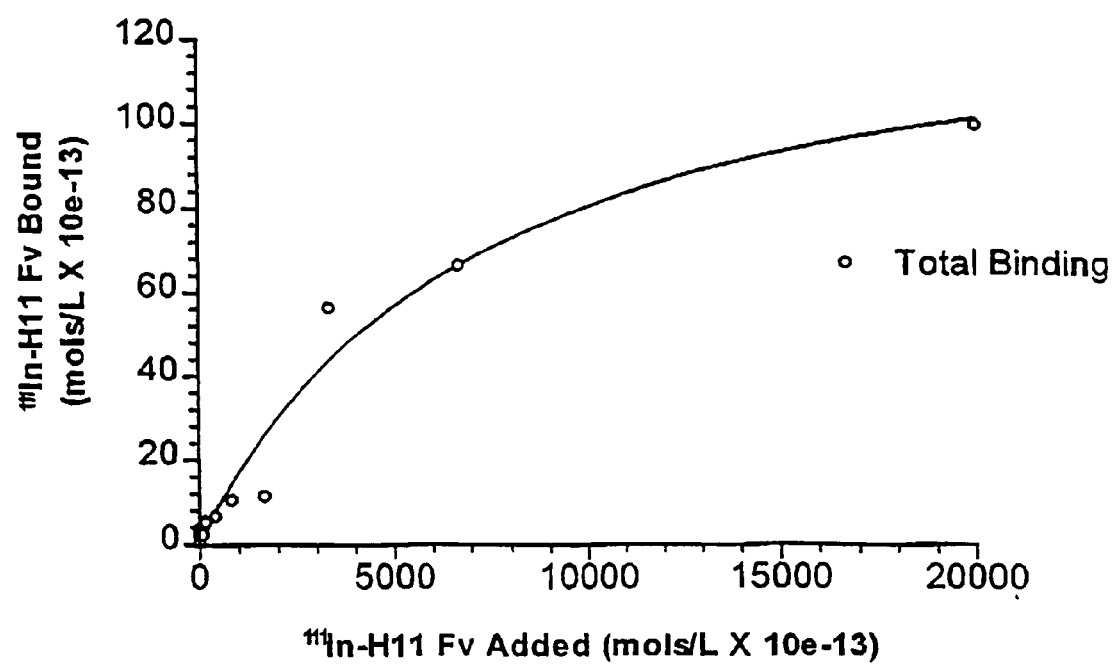
FIG. 14 depicts the binding of $^{111}$I-H11-scFv to A375.

$^{125}$I labeled H11-scFv demonstrated an affinity of binding (Ka) of $3 \times 10^8$ L/mol for LS174T cells (specific binding shown in FIG. 13). $^{111}$In-H11-scFv demonstrated an affinity of binding (Ka) of $3.6 \times 10^8$ L/mol for A-375 cells and $1.4 \times 10^9$ L/mol for SKMG1 cells. The results are depicted in FIG. 14. There were approximately 24,000 binding sites/cell for A-375 cells and approximately 5000 binding sites/cell for SKMG1.

These results indicate that purified forms of Mab H11 bind to a cell surface-associated antigen(s) expressed on breast adenocarcinoma (SK-BR-3), glioblastoma (SKMG-1), and melanoma (A-375) lymphoma cell lines.

In order to further test the reactivity of biotinylated H11-scFv to live lymphoma cells, cells from tumor cell lines were prepared and incubated with biotinylated H11-scFv at a protein concentration of either 100 µg/mL or 200 µg/mL and analyzed by flow cytometry as described above in Example 2. The mean fluorescence and % positive cells were measured by flow cytometry. The control for scFv binding was biotinylated BGA scFv. Results are shown in Table 13.

TABLE 13

| CELL LINE | SAMPLES | CONC. (µg/mL) | MEAN FLUORESCENCE | % FLUORESCENCE INCREASE | % POSITIVE CELLS |
|---|---|---|---|---|---|
| Burkitt's Lymphoma CA-46 | PBS | | 123 | | 10 |
| | BIOTIN-BGA scFv | 200 | 126 | | 9 |
| | | 100 | 133 | | 14 |
| | BIOTIN-H11-scFv | 200 | 262 | 108 | 76 |
| | | 100 | 221 | 66 | 58 |
| T cell | PBS | | 150 | | 6 |
| lymphoma H9 | BIOTIN-BGA scFv | 200 | 155 | | 8 |
| | | 100 | 149 | | 7 |
| | BIOTIN-H11-scFv | 200 | 186 | 20 | 13 |
| | | 100 | 171 | 15 | 9 |
| Acute lymphoblastoid leukemia CCRF-CEM | PBS | | 151 | | 8 |
| | BIOTIN-BGA scFv | 200 | 171 | | 14 |
| | | 100 | 159 | | 10 |
| | BIOTIN-H11-scFv | 200 | 231 | 35 | 34 |
| | | 100 | 242 | 52 | 38 |
| Burkitt's Lymphoma RAMOS | PBS | | 151 | | 10 |
| | BIOTIN-BGA scFv | 200 | 174 | | 15 |
| | | 100 | 169 | | 13 |
| | BIOTIN-H11-scFv | 200 | 423 | 143 | 95 |
| | | 100 | 316 | 87 | 67 |

EXAMPLE 9

Binding of Biotinylated H11-scFv to Human Tumor Cells Determined by Immunoperoxidase Staining In order to determine immunoreactivity of H11-scFv, the following experiment was performed. Tumor cells were grown in T-flasks and cytospins were prepared and incubated with biotinylated H11-scFv or PBS to determine binding.

The results of the immunoreactivity of H11-scFv are shown in Table 14 where reactivity is indicated as negative (−), weak positive (±), positive (+ or ++). These results indicate that, as determined by immunoperoxidase staining, the epitope recognized by Mab H11 is expressed by a number of different types of human tumor cells and cell lines.

TABLE 14

| | REACTIVITY | |
|---|---|---|
| CELL LINES/TYPE OF TUMOR | PBS | H11-scFv (50 µg/mL) |
| HUMAN GLIOBLASTOMA | | |
| SKMG 1 | -- | + |
| U-87 MG | -- | + |
| HUMAN MALIGNANT MELANOMA | | |
| A-375 | -- | + |
| SK-MEL-5 | -- | ++ |
| HUMAN COLON ADENOCARCINOMA | | |
| SK-CO-1 | -- | + |
| HT-29 | -- | + |
| 174T | -- | + |
| HUMAN BREAST ADENOCARCINOMA | | |
| SK-BR-3 | -- | + |
| BT-20 | -- | + |
| HUMAN LYMPHOMA CELL LINES | | |
| U-937 Histocytic Lymphoma | -- | ± |
| H9 T Cell Lymphoma | -- | + |
| CEM Acute Lymphoblastoid leukemia | -- | - |
| MOLT-3 Acute Lymphoblastoid leukemia | -- | ± |
| HL-60 Promyelocytic leukemia | -- | + |

TABLE 14-continued

| CELL LINES/TYPE OF TUMOR | REACTIVITY | |
|---|---|---|
| | PBS | H11-scFv (50 μg/mL) |
| KG-1 Acute myelogenous leukemia | -- | + |
| K-562 Chronic myelogenous leukemia | -- | + |
| GASTRIC CARCINOMA | | |
| KATO III | -- | ++ |
| HUMAN OSTEOGENIC SARCOMA | | |
| SAOS-2 | -- | ± |
| HUMAN OVARY ADENOCARCINOMA | | |
| SK-OV-3 | -- | ± |
| BLADDER CELL CARCINOMA | | |
| T-24 | -- | + |
| LARYNX CARCINOMA | | |
| Hep-2 | -- | + |

EXAMPLE 10

Reactivity of Recombinantly Produced H11 IgG1

H11 IgG1 was produced in Chinese Hamster Ovary (CHO) cells as follows. Several vectors containing cDNAs encoding light and heavy chain sequences of H11 were prepared. The orientation, DNA inserts and antibiotic selection criteria of these constructs are shown in Table 15 where CMV is cytomegalovirus; DHFR is dihydrofolate reductase; HC is heavy chain and LC is light chain.

TABLE 15

| vector | DNA insert | HC + LC promoter | promoter orientation | antibiotic selection | amplif. |
|---|---|---|---|---|---|
| ppNB1 | cDNA heavy and light chains | CMV* | HC- clockwise LC- anticlockwise | neomycin | DHFR |
| pNB2 | cDNA heavy and light chains | CMV | HC - clockwise LC- clockwise | zeocin | DHFR |
| pNB3 | cDNA heavy and light chains | CMV | HC - clockwise LC- anticlockwise | zeocin | DHFR |

These expression vectors have separate insertional sites for the sequences encoding the light and heavy antibody chains. A high level of constitutive expression of both the heavy and light chains is directed by the cytomegalovirus immediate-early (CMV) enhancer/promoter. A chimeric intron comprising the 5' donor site of the first intron of the human β-globin and the 3' acceptor site from the intron of an immunoglobulin gene (heavy chain variable region) is located downstream from the promoter which has frequently been shown to enhance gene expression levels. Polyadenylation of mRNAs are provided by the poladenylation signal from the simian virus 40 (SV40).

Figure 15:
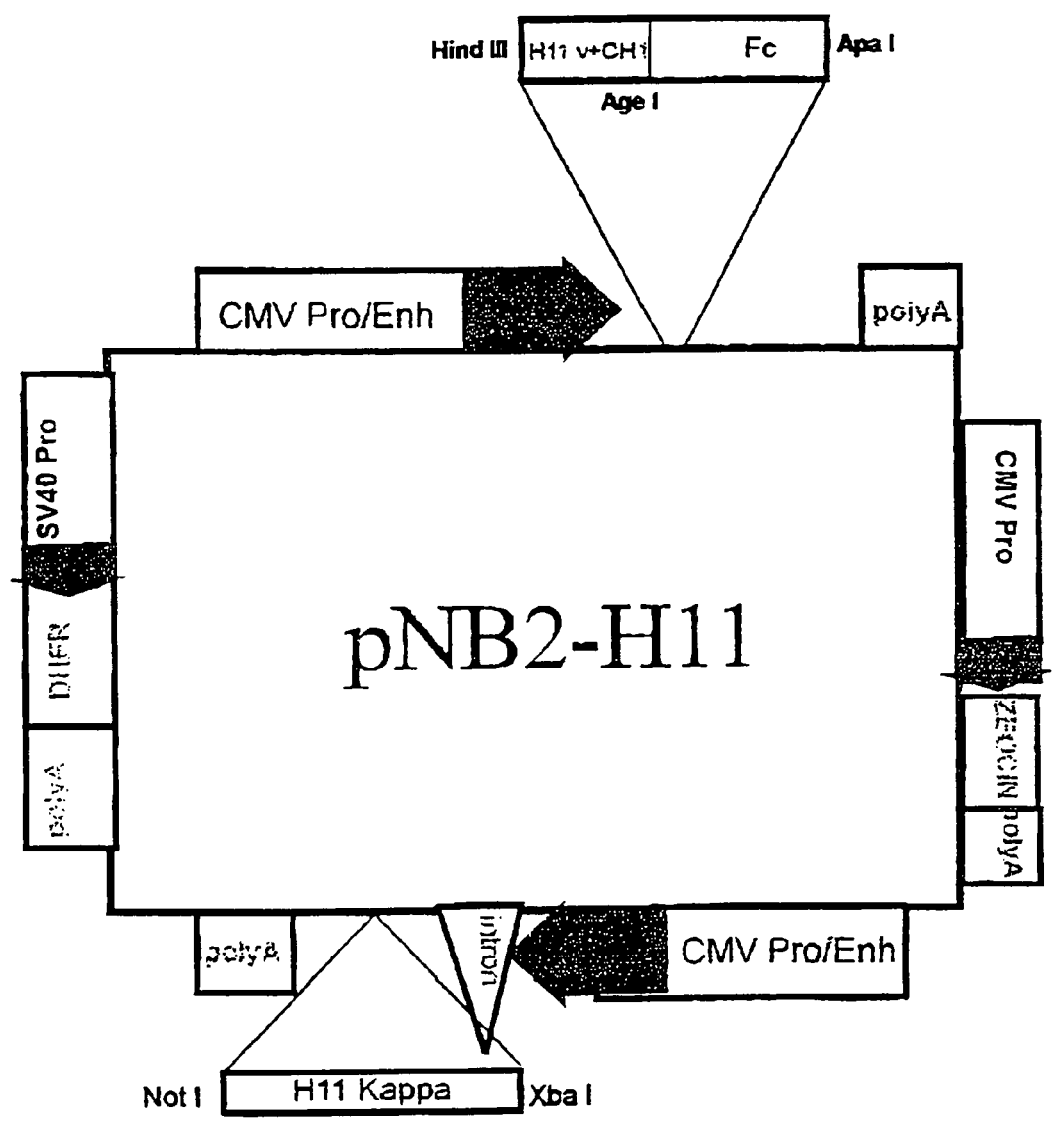
FIG. 15 depicts the mammalian expression vector pNB2 used to transfect and express recombinant H11-IgG.
Figure 16:
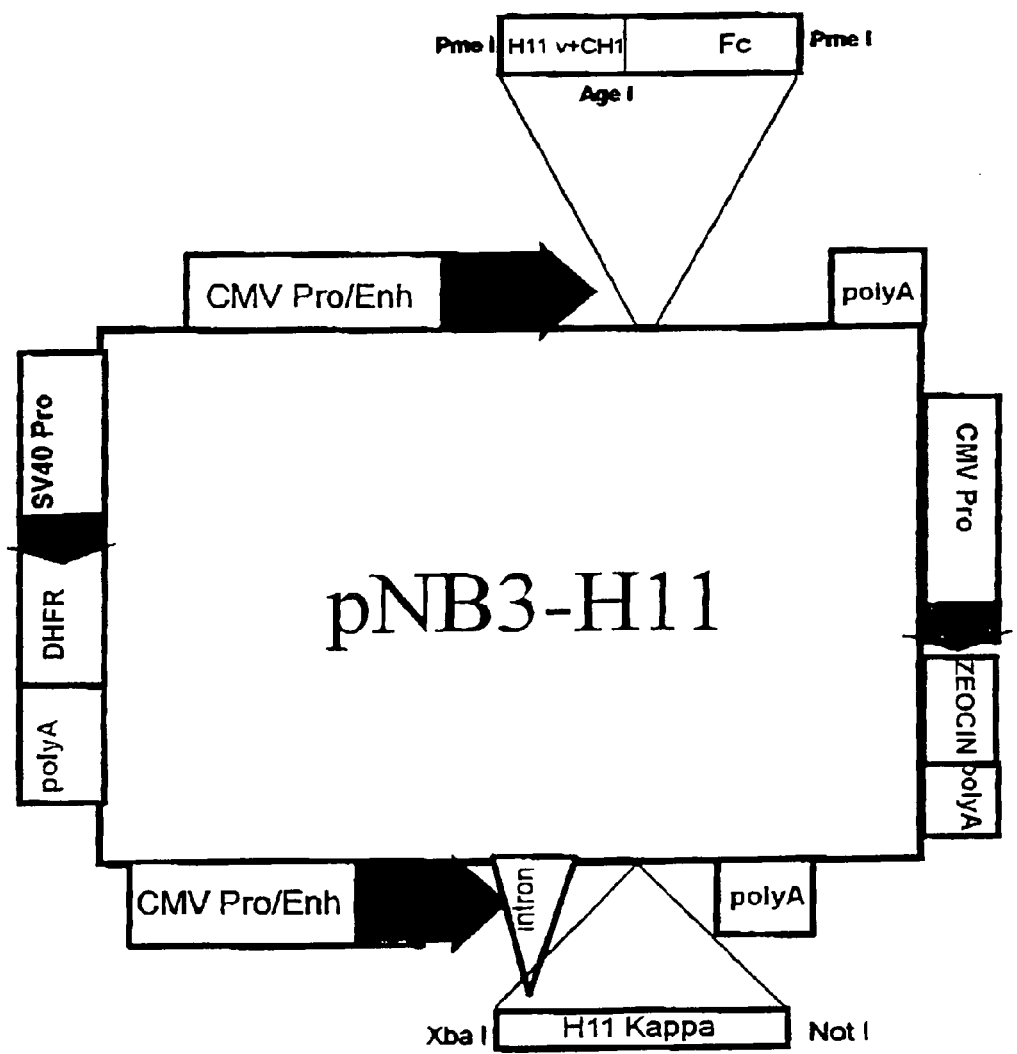
FIG. 16 depicts the mammalian expression vector pNB3 used to transfect and express recombinant H11-IgG.

The plasmids also contain the gene encoding dihydrofolate reductase (DHFR) and can thus be grown in Chinese hamster ovary (CHO) DHFR deficient cells. Amplification using methotrexate, a folate analogue and potent DHFR inhibitor, results in amplification of the DHFR gene and its flanking sequences (namely, the light and heavy chains of the antibody in the construct). A stepwise increase in methotrexate (from about 0.01 nM to about 800 nM) concentration can produce very high levels of protein from the target gene(s). The constructs also contain a gene which confers antibiotic resistance was a selectable marker, either neomycin or zeomycin is used. The vectors are shown in FIGS. 15 and 16.

Results of flow-cytometry analysis of recombinantly produced H11 IgG1 are shown in Table 16 and illustrate that H11 IgG1 which binds to an antigen on SK-BR-3 breast carcinoma cells can be produced in CHO cells.

TABLE 16

| Cell Lines/I.D. | Conc. of IgG1 in samples (mg/L) | Mean Fluorescence (MF) | % Increase of MF above IgG1 control |
|---|---|---|---|
| PBS | | 156 | |
| Control IgG1 | 5 | 169 | |
| 1129/pNB1 | 2 | 172 | 2 |
| 1233/pNB1 | 2 | 184 | 9 |
| KL-13/pNB2 | 3.3 | 192 | 14 |
| KL-14/pNB2 | 3.3 | 186 | 10 |
| Sb2/pNB3 | 4.0 | 224 | 33 |
| 3sB3/pNB3 | 3.9 | 200 | 18 |

EXAMPLE 11

H11 Binding to Cancer Cell Lines

The binding affinities of H11 IgM and H11-scFv for various human cancer cell lines were determined by labeling H11 antibodies with either radioactive iodine or radioactive indium. $^{125}$I-H11-scFv was prepared with specific activities of 7, 20 or 150 μCi/μg and $^{125}$I-H11 IgM with 0.6 μCi/μg were obtained. In addition, $^{111}$In-H11-scFv having a specific activity of 13 and 38 μCi/μg was prepared as described in Example 12. The scFv 3B 1, which does not recognize the C-antigen, was used as a control to indicate non-specific binding and was labeled with 150 μCi/μg.

Figure 17:
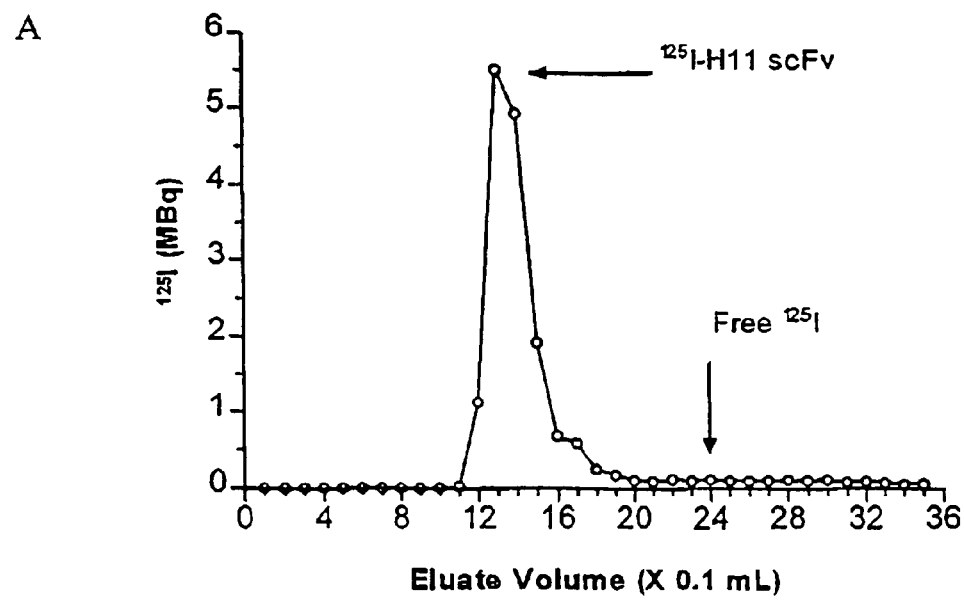
FIG. 17 depicts the purification of $^{125}$I-H11-scFv on P-2 minicolumn (A) and analysis of $^{125}$I-H11-scFv by paper chromatography in 85% methanol (B).
Figure 17:
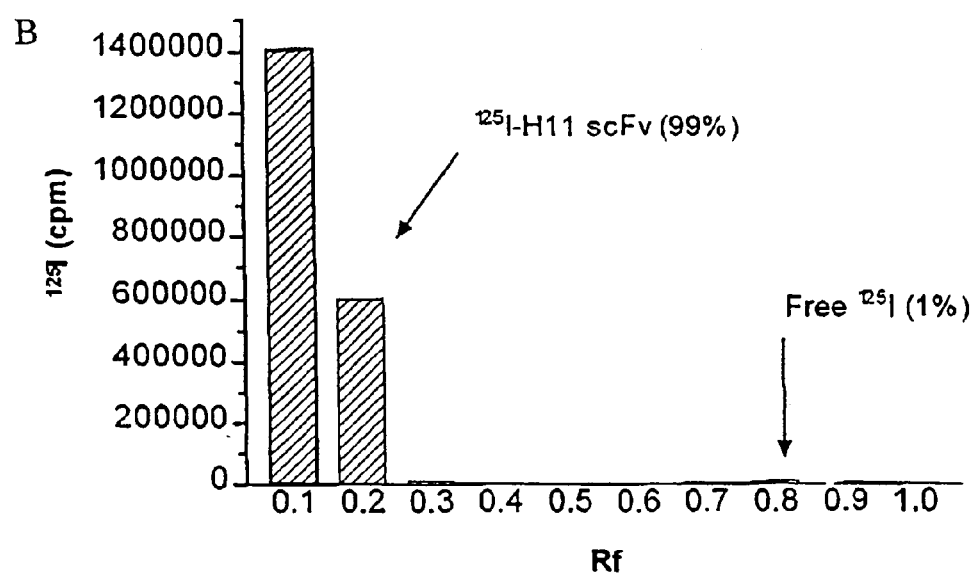
Figure 18:
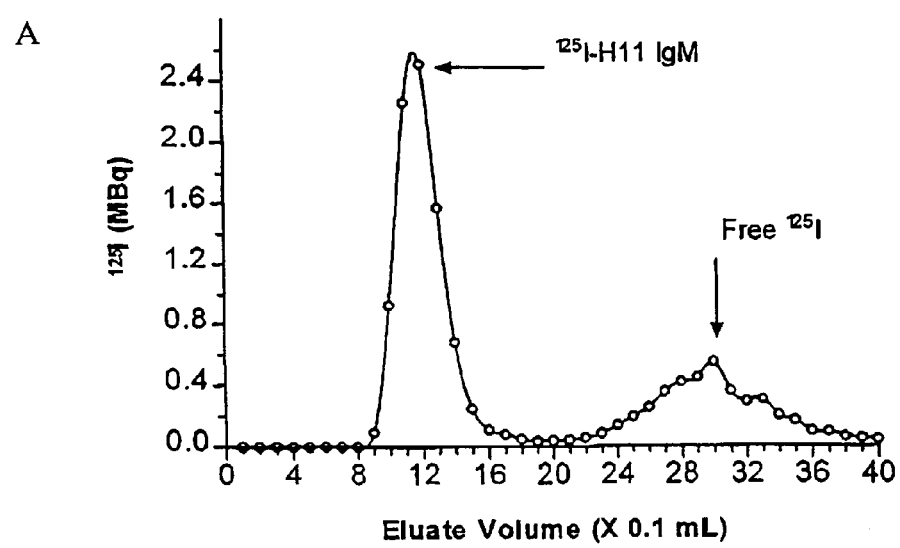
FIG. 18 depicts the purification of $^{125}$I-H11 IgM on a Sephadex G-25 minicolumn (A) and analysis of $^{125}$I-H11 IgM by paper chromatography in 85% methanol (B).
Figure 18:
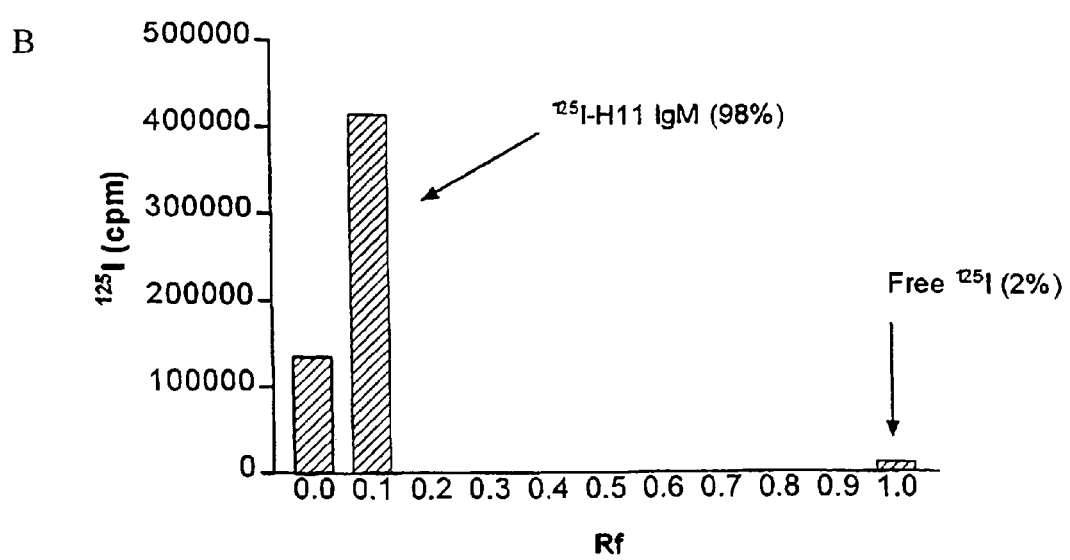
Figure 19:
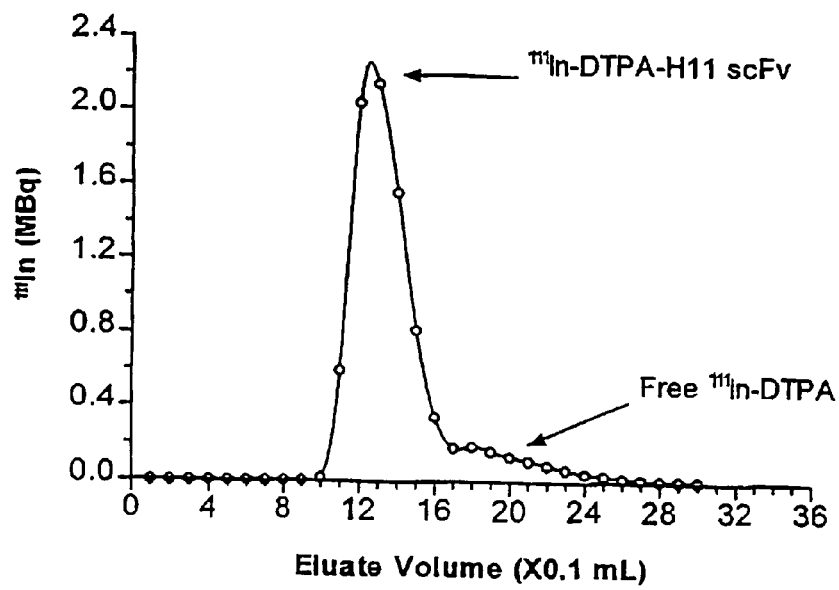
FIG. 19 depicts the purification of $^{111}$In-DTPA-H11-scFv on Sephadex G-50 minicolumn (A) and analysis of $^{111}$In-DTPA-H11-scFv by ITLC-SG/0.1M citrate (B).
Figure 19:
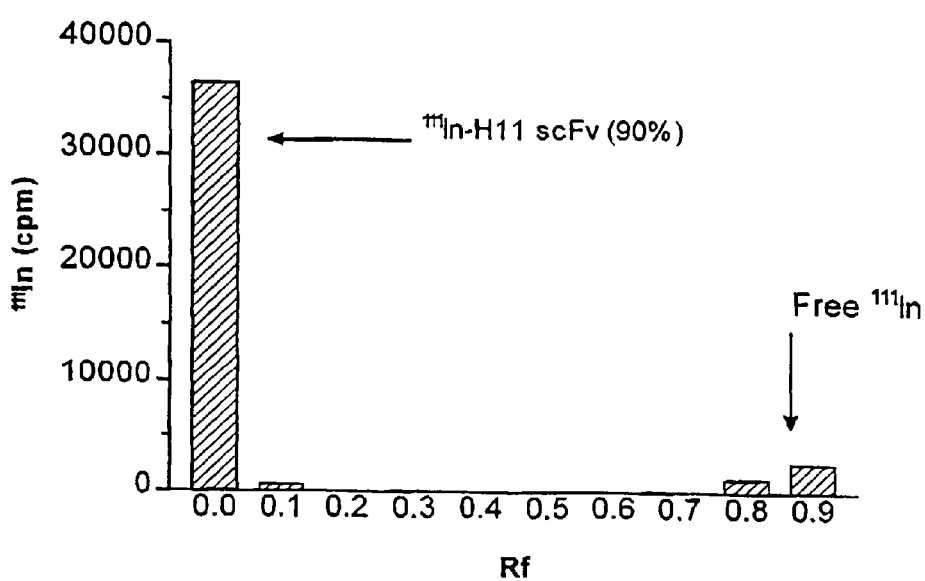

$^{125}$I-H11-scFv was purified using a P-2 minicolumn and analyzed by paper chromatography in 85% methanol as shown in FIG. 17. $^{125}$I-H11 IgM was purified using a Sephadex G-50 mini-column (Pharmacia) and analyzed by paper chromatography in 85% methanol as shown in FIG. 18. A Sephadex G-50 column was used to purify $^{111}$In-H111 scFv which was then analyzed by ITLC-SG in 0.1 M Citrate as shown in FIG. 19.

Results of H11 binding are shown in FIGS. 13 and 14. FIG. 13 shows the specific binding of $^{125}$I-H11-scFv to LS174T human colon cancer cells. FIG. 14 shows the total binding of $^{111}$In-H11-scFv to A375 cells.

The results obtained indicate that H11 binds specifically to both LT174T and human melanoma cells. H11 also binds, but with lower affinity, to the breast cancer cell line.

EXAMPLE 12

Tumor Imaging with $^{111}$Indium-DTPA-H11-scFv

H11-scFv was conjugated with the bycyclic anhydride of diethylenetriaminepentaacetic acid (DTPA) at a molar ratio of 10:1 (DTPA:H11-scFv) resulting in a substitution level of 2 moles of DTPA per mole of H11-scFv. DTPA-H11-scFv was purified from excess DTPA on a Sephadex G-25 (Pharmacia) mini-column and reconcentrated to 10 mg/mL using a Centricon-30 microconcentrator (Amicon). The DTPA-H11-scFv was radiolabeled to a specific activity of 25 mCi/mg with [111]Indium acetate. Unincorporated $^{111}$In was removed using a Sephadex G-25 minicolumn. The [111]Indium acetate was prepared from [111]Indium chloride (Nordion) and 1 M acetate buffer at pH 6.0. The radiochemical purity of the final $^{111}$In-DTAP-H11-scFv was greater than 99% as measured by thin layer silica gel chromatography in 100 mM sodium citrate pH 5.0. FIG. 19 shows the purification and TLC.

A female nude mouse with an existing subcutaneous A375 melanoma xenograft on the right lateral side and a subcutaneous HT-29 human colon cancer xenograft in the mid-abdominal region was injected intravenously in the tail vein with 100 µCi of $^{111}$In-DTAP-H11-scFv. The mouse was immediately placed under the gamma camera (Siemans ZL3700) interfaced with a GE Star 4000i computer and a dynamic acquisition was obtained for 120 minutes, for a total of 480 frames of 15 seconds each. The frames were then combined into 12×10 minute images. The A375 tumor was visible on the right lateral side of the mouse as early as 30 minutes post-injection.

Figure 20:
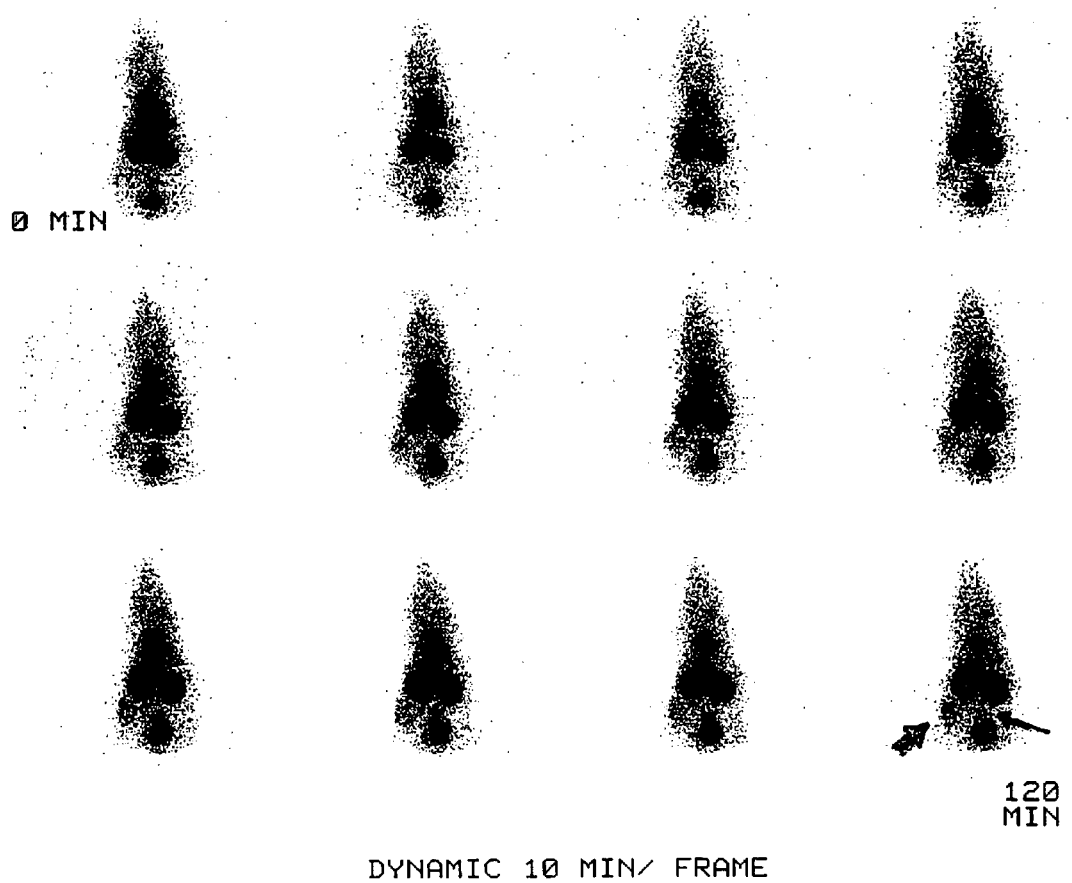
FIG. 20 depicts in vivo binding of $^{111}$In-H11-scFv to A375 xenograft tumors in nude mice.

Region-of-interest analysis of the two tumors showed that the A375 tumor accumulated radioactivity throughout the 120 minute study, whereas the HT-29 tumor accumulated radioactivity for the first hour and then the radioactivity concentration remained relatively constant. FIG. 20 shows 12 frames and the two arrows on the bottom right hand frame, taken at 120 minutes, show the accumulation of radioactivity in the two tumors. The narrow arrow points to the A375 tumor, and the broad arrow points to the HT-29 tumor. Normal tissues visible on the images include the heart, liver, kidneys and bladder. The heart is visible due to circulating amounts of radioactivity, and the kidneys and bladder are visible due to renal elimination of $^{111}$In-DTAP-H11-scFv. The small amount of liver uptake may be due to blood flow to the liver or to partial binding of $^{111}$In-DTAP-H11-scFv to the liver.

Although the foregoing invention has been described in some detail by way of illustration and example for purposes of clarity and understanding, it will be apparent to those skilled in the art that certain changes and modifications may be practiced. Therefore, the description and examples should not be construed as limiting the scope of the invention, which is delineated by the appended claims.

We claim:

1. An isolated polynucleotide comprising a sequence that encodes an antigen binding polypeptide wherein the polypeptide comprises an H chain V region and an L chain V region of the polypeptide encoded by the nucleic acid sequence as shown in SEQ ID NO:13, and wherein the antigen binding polypeptide specifically recognizes a cancer cell surface antigen and does not recognize a normal non-cancerous cell surface antigen.

2. The polynucleotide of claim 1, wherein said antigen binding polypeptide specifically recognizes any one or more of at least glioma, melanoma, breast carcinoma, lung carcinoma, ovarian carcinoma, lymphoma, gastric carcinoma, colon carcinoma or prostate carcinoma cells.

3. The polynucleotide of claim 1, wherein the polynucleotide encodes both of the amino acid sequences of the H chain V region and the L chain V region of the polypeptide as shown in SEQ ID NO:14.

4. The polynucleotide of claim 1 or 2, wherein the antigen binding polypeptide comprises a CDR region of the polypeptide as shown in SEQ ID NO:14.

5. The polynucleotide of claim 1 or 2, wherein the antigen binding polypeptide comprises at least one of the H chain CDR1, CDR2, or CDR3 of the polypeptide as shown in SEQ ID NO:14.

6. The polynucleotide of claim 5, wherein the antigen binding polypeptide comprises the H chain CDR2 of the polypeptide as shown in SEQ ID NO:14.

7. The polynucleotide of claim 5, wherein the antigen binding polypeptide comprises the H chain CDR3 of the polypeptide as shown in SEQ ID NO:14.

8. The polynucleotide of claim 5, wherein the antigen binding polypeptide comprises the H chain CDR2 and CDR3 of the polypeptide as shown in SEQ ID NO:14.

9. The polynucleotide of claim 1 or 2, wherein the antigen binding polypeptide comprises the L chain CDR3 of the polypeptide as shown in SEQ ID NO:14.

10. The polynucleotide of claim 1 or 2, comprising the polynucleotide of SEQ ID NO:13.

11. The polynucleotide of claim 1 or 2, wherein the antigen binding polypeptide comprises a variable region of the polypeptide as shown in SEQ ID NO:14.

12. The polynucleotide of claim 1 or 2, wherein the polynucleotide further encodes at least one functional moiety.

13. The polynucleotide of claim 12, wherein the at least one functional moiety is selected from the group consisting of a signal peptide, an agent that enhances immunologic reactivity, an agent that facilitate coupling to a solid support, a carrier, a bioresponse modifier, a toxin, a detectable label, and a drug.

14. The polynucleotide of claim 13, wherein the signal peptide is prokaryotic.

15. The polynucleotide of claim 13, wherein the agent that enhances immunologic reactivity is a bacterial superantigen.

16. The polynucleotide of claim 13, wherein the bioresponse modifier is a cytokine.

17. The polynucleotide of claim 13, wherein the functional moiety is a toxin selected from the group consisting of ricin, pokeweed antiviral protein, *Pseudomonas* exotoxin A, diphtheria toxin, ricin A chain, restrictocin, and phospholipase enzymes.

18. The polynucleotide of claim 1 or 2, wherein the antigen binding polypeptide is selected from the group consisting of whole native antibodies, bispecific antibodies, chimeric antibodies, Fab, F(ab')2, single chain V region fragments (scFv) and fusion polypeptides.

19. The polynucleotide of claim 1 or 2, wherein said antigen binding polypeptide is an antigen binding polypeptide of a human antibody.

20. An isolated cloning vector comprising a polynucleotide of claim 1 or 2.

21. An expression vector comprising a polynucleotide of claim 1 or 2.

22. An isolated host cell comprising a polynucleotide of claim 1 or 2.

23. A composition comprising a polynucleotide of claim 1 or 2.

24. A method for making a polynucleotide of claim 1 or 2 comprising preparing the polynucleotide using one or method selected from: chemical synthesis, nucleic acid amplification, and recombinant cloning methods.

25. A method for making an antigen binding polypeptide by expressing a polynucleotide of claim 1 in a host cell.

26. An isolated polynucleotide encoding a diabody comprising an antigen binding polypeptide according to claim 1 or 2.

27. An isolated polynucleotide encoding a dimer comprising an antigen binding polypeptide according to claim 1 or 2.

28. The polynucleotide according to claim 1 or 2 wherein the antigen binding polypeptide does not specifically recognize any one of normal non-cancerous adrenal, bladder, cervix, esophagus, eye, heart, kidney, liver, muscle, pancreas, parotid, pituitary, small intestine, spinal cord, spleen, thymus, thyroid, testis, or uterus cells.

29. The polynucleotide of claim 1 or 2, wherein the antigen binding polypeptide is a humanized antigen binding polypeptide.

30. The polynucleotide of claim 1 or 2, wherein the antigen binding polypeptide comprises a heterologous immunoglobulin constant region.

31. The polynucleotide of claim 1 or 2, wherein the polynucleotide encodes a ScFv or antibody to a cancer cell surface epitope, wherein the ScFv or antibody is comprised of the amino acid sequences of the H chain V region and the L chain V region of the polypeptide as shown in SEQ ID NO:14, and wherein the antigen binding polypeptide specifically recognizes a cancer cell surface antigen and does not recognize a normal non-cancerous cell surface antigen.

32. The polynucleotide of claim 1 or 2, wherein the antigen binding polypeptide is a polypeptide derivative or a functionally equivalent fragment of the ScFv or antibody.

33. The polynucleotide of claim 1 or 2, wherein said antigen binding polypeptide comprises a H and L chain CDR1, CDR2, or CDR3 which consists of the amino acid sequence of the corresponding CDR of a scFv or antibody or with exception of one or more deletions, additions or substitutions relative to the amino acid sequence, while having substantially the same specificity of the scFv or antibody.

34. The polynucleotide of claim 1 or 2, wherein the antigen binding polypeptide comprises at least a portion of a variable region of a scFv or antibody as shown in SEQ ID NO:14 such that said antigen binding polypeptide retains the specificity of the scFv or antibody.

35. The polynucleotide of claim 1 or 2, wherein the antigen binding polypeptide comprises an amino acid sequence for at least one CDR which plays a role in the specificity of the antibody as shown in SEQ ID NO:14.

36. An isolated polynucleotide comprising a sequence that encodes an antigen binding polypeptide, wherein said polypeptide comprises an H chain CDR3 that is encoded by the nucleic acid sequence as shown in SEQ ID NO:13, and wherein the antigen binding polypeptide specifically recognizes a cancer cell surface antigen and does not recognize a normal non-cancerous cell surface antigen.

37. An isolated polynucleotide comprising a sequence that encodes an antigen binding polypeptide, wherein said polypeptide comprises an L chain CDR3 that is encoded by the nucleic acid sequence as shown in SEQ ID NO:13, and wherein the antigen binding polypeptide specifically recognizes a cancer cell surface antigen and does not recognize a normal non-cancerous cell surface antigen.

38. The isolated polynucleotide of claim 36 or 37, wherein said antigen binding polypeptide specifically recognizes any one or more of at least glioma, melanoma, breast carcinoma, lung carcinoma, ovarian carcinoma, lymphoma, gastric carcinoma, colon carcinoma or prostate carcinoma cells.

39. The isolated polynucleotide of claim 36 or 37, wherein said antigen binding polypeptide is selected from the group consisting of whole native antibodies, bispecific antibodies, chimeric antibodies, Fab, F(ab')2, single chain V region fragments (scFv) and fusion polypeptides.

40. The isolated polynucleotide of claim 36 or 37, wherein the polynucleotide further encodes at least one functional moiety.

41. The isolated polynucleotide of claim 40, wherein the at least one functional moiety is selected from the group consisting of a signal peptide, an agent that enhances immunologic reactivity, an agent that facilitates coupling to a solid support, a carrier, a bioresponse modifier, a toxin, a detectable label, and a drug.

42. The isolated polynucleotide of claim 41, wherein the signal peptide is prokaryotic.

43. The isolated polynucleotide of claim 41, wherein the agent that enhances immunologic reactivity is a bacterial superantigen.

44. The isolated polynucleotide of claim 41, wherein the bioresponse modifier is a cytokine.

45. The polynucleotide of claim 40, wherein the functional moiety is a toxin selected from the group consisting of ricin, pokeweed antiviral protein, *Pseudomonas* exotoxin A, diphtheria toxin, ricin A chain, restrictocin, and phospholipase enzymes.

46. An isolated vector comprising a polynucleotide of claim 1, 10, 36 or 37.

47. An isolated host cell comprising a polynucleotide of claim 10, 36 or 37.

48. A composition comprising a polynucleotide of claim 10, 36 or 37.

49. An isolated polynucleotide comprising a sequence that encodes a polypeptide comprising an H chain V region or an L chain V region of the polypeptide encoded by the nucleic acid sequence as shown in SEQ ID NO:13.

\* \* \* \* \*